US010364437B2

(12) United States Patent
Schnable et al.

(10) Patent No.: US 10,364,437 B2
(45) Date of Patent: Jul. 30, 2019

(54) PLANT GENES INVOLVED IN NITRATE UPTAKE AND METABOLISM

(71) Applicant: Iowa State University Research Foundation, Inc., Ames, IA (US)

(72) Inventors: Patrick S. Schnable, Ames, IA (US); Sudhansu Dash, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 40 days.

(21) Appl. No.: 15/348,425

(22) Filed: Nov. 10, 2016

(65) Prior Publication Data

US 2017/0058287 A1 Mar. 2, 2017

Related U.S. Application Data

(60) Division of application No. 14/462,017, filed on Aug. 18, 2014, now Pat. No. 9,523,099, which is a continuation of application No. 11/876,534, filed on Oct. 22, 2007, now abandoned.

(60) Provisional application No. 60/869,290, filed on Dec. 8, 2006.

(51) Int. Cl.
*A01H 1/00* (2006.01)
*C12N 15/82* (2006.01)
*C07K 14/415* (2006.01)

(52) U.S. Cl.
CPC ........... *C12N 15/8261* (2013.01); *A01H 1/00* (2013.01); *C07K 14/415* (2013.01); *C12N 15/8222* (2013.01); *C12N 15/8238* (2013.01)

(58) Field of Classification Search
None
See application file for complete search history.

(56) References Cited

U.S. PATENT DOCUMENTS

| | | | |
|---|---|---|---|
| 5,391,725 | A | 2/1995 | Coruzzi et al. |
| 5,608,144 | A | 3/1997 | Baden et al. |
| 5,633,441 | A | 5/1997 | De Greef et al. |
| 5,998,700 | A | 12/1999 | Lightfoot et al. |
| 6,084,153 | A | 7/2000 | Good et al. |
| 6,107,547 | A | 8/2000 | Coruzzi et al. |
| 6,342,581 | B1 | 1/2002 | Rosen et al. |
| 6,506,963 | B1 | 1/2003 | De Both et al. |
| 6,852,519 | B2 | 2/2005 | Wei et al. |
| 6,936,693 | B2 | 8/2005 | Hresko et al. |
| 6,939,701 | B2 | 9/2005 | Yaver et al. |
| 6,942,973 | B2 | 9/2005 | Yaver et al. |
| 7,038,030 | B2 | 5/2006 | Litman et al. |
| 7,193,033 | B2 | 3/2007 | Mori et al. |
| 7,195,901 | B1 | 3/2007 | McKeon et al. |
| 7,214,786 | B2 | 5/2007 | Kovalic et al. |
| 7,247,440 | B2 | 7/2007 | Mori et al. |
| 7,285,265 | B2 | 10/2007 | Vogels et al. |
| 7,348,142 | B2 | 3/2008 | Wang |
| 7,375,074 | B2 | 5/2008 | Hirokazu et al. |
| H2220 | H | 7/2008 | Wang |
| 7,396,979 | B2 | 7/2008 | Alexandrov et al. |
| 7,399,587 | B2 | 7/2008 | Tenmizu et al. |
| 7,427,399 | B2 | 9/2008 | Jakobovits et al. |
| 7,429,382 | B2 | 9/2008 | Albone et al. |
| 7,435,168 | B2 | 10/2008 | Fatland-Bloom et al. |
| 7,439,067 | B2 | 10/2008 | Lasure et al. |
| 7,442,533 | B2 | 10/2008 | Williams et al. |
| 7,473,526 | B2 | 1/2009 | Wang |
| 7,507,875 | B2 | 3/2009 | Bloksberg et al. |
| 7,511,190 | B2 | 3/2009 | Creelman et al. |
| 7,514,597 | B2 | 4/2009 | Nakamura et al. |
| 7,521,230 | B2 | 4/2009 | Ikezu |
| 7,525,016 | B1 | 4/2009 | Peters et al. |
| 7,538,204 | B2 | 5/2009 | Ramli et al. |
| 7,569,389 | B2 | 8/2009 | Feldmann et al. |
| 7,611,705 | B2 | 11/2009 | Chang |
| 7,659,446 | B2 | 2/2010 | Sherman et al. |
| 7,700,852 | B2 | 4/2010 | Demmer et al. |
| 7,709,611 | B2 | 5/2010 | Li et al. |
| 7,745,391 | B2 | 6/2010 | Mintz et al. |
| 7,750,207 | B2 | 7/2010 | Wu et al. |
| 7,750,209 | B2 | 7/2010 | Tanaka et al. |
| 7,786,272 | B2 | 8/2010 | Goddard et al. |
| 7,790,958 | B2 | 9/2010 | Boukharov et al. |
| 7,834,146 | B2 | 11/2010 | Kovalic et al. |
| 7,838,278 | B2 | 11/2010 | Fatland-Bloom et al. |
| 7,855,321 | B2 | 12/2010 | Renz et al. |
| 7,863,001 | B2 | 1/2011 | Dai et al. |
| 7,867,749 | B2 | 1/2011 | Williams et al. |
| 7,868,149 | B2 | 1/2011 | Boukharov et al. |
| 7,892,730 | B2 | 2/2011 | Morris et al. |
| 7,910,800 | B2 | 3/2011 | Karchi et al. |

(Continued)

FOREIGN PATENT DOCUMENTS

| | | | |
|---|---|---|---|
| WO | WO 2006/030445 | A2 | 3/2006 |
| WO | WO 2008/051608 | A2 | 5/2008 |

OTHER PUBLICATIONS

Brazilian Office Action for corresponding Brazilian Patent Application No. PI0720219-9, 16 pages (dated Jan. 19, 2017).

(Continued)

*Primary Examiner* — Phuong T Bui
(74) *Attorney, Agent, or Firm* — Pepper Hamilton LLP

(57) ABSTRACT

The present invention relates nucleic acid molecules that are modulated (e.g., upregulated) by nitrogen in corn, to proteins or polypeptides encoded by these nucleic acid molecules, and promoters of these nucleic acid molecules. The present invention relates to a nucleic acid construct having a nucleic acid molecule that is modulated by nitrogen in corn, as well as to expression systems, host cells, plants, and plant seeds having the nucleic acid construct. The present invention also relates to a method of expressing the nucleic acid molecule that is modulated by nitrogen in a plant by growing a transgenic plant or a plant grown from a transgenic seed transformed with the construct. The present invention further relates to an isolated DNA promoter that can be used to direct nitrogen-regulated expression of an isolated nucleic acid in plants.

10 Claims, No Drawings

Specification includes a Sequence Listing.

(56) References Cited

U.S. PATENT DOCUMENTS

| | | | |
|---|---|---|---|
| 7,956,242 | B2 | 6/2011 | Zhang et al. |
| 7,960,612 | B2 | 6/2011 | Zhang et al. |
| 7,968,689 | B2 | 6/2011 | Rosen et al. |
| 7,985,571 | B1 | 7/2011 | Ryan |
| 7,989,676 | B2 | 8/2011 | Troukhan et al. |
| 8,014,957 | B2 | 9/2011 | Radich et al. |
| 8,030,290 | B2 | 10/2011 | Rossi et al. |
| 8,030,546 | B2 | 10/2011 | Reuber et al. |
| 8,063,186 | B2 | 11/2011 | Goddard et al. |
| 8,106,174 | B2 | 1/2012 | Kovalic et al. |
| 8,110,725 | B2 | 2/2012 | Riechmann et al. |
| 9,416,367 | B2 | 8/2016 | McClaren et al. |
| 2001/0000266 | A1 | 4/2001 | Schmidt et al. |
| 2001/0003848 | A1 | 6/2001 | Frommer et al. |
| 2002/0069430 | A1 | 6/2002 | Kisaka et al. |
| 2003/0022305 | A1 | 1/2003 | Coruzzi et al. |
| 2004/0031072 | A1 | 2/2004 | La Rosa et al. |
| 2004/0034888 | A1 | 2/2004 | Liu et al. |
| 2004/0123343 | A1 | 6/2004 | La Rosa et al. |
| 2004/0214272 | A1 | 10/2004 | La Rosa et al. |
| 2005/0044585 | A1 | 2/2005 | Good et al. |
| 2005/0158323 | A1 | 7/2005 | Evans et al. |
| 2006/0048240 | A1 | 3/2006 | Alexandrov et al. |
| 2006/0107345 | A1 | 5/2006 | Alexandrov et al. |
| 2006/0123505 | A1 | 6/2006 | Kikuchi et al. |
| 2006/0150283 | A1 | 7/2006 | Alexandrov et al. |
| 2007/0016974 | A1 | 1/2007 | Byrum et al. |
| 2007/0020621 | A1 | 1/2007 | Boukharov et al. |
| 2007/0061916 | A1 | 3/2007 | Kovalic et al. |
| 2007/0067865 | A1 | 3/2007 | Kovalic et al. |
| 2007/0143875 | A1 | 6/2007 | Conner et al. |
| 2007/0150978 | A1 | 6/2007 | Byrum |
| 2007/0224595 | A1 | 9/2007 | Andersen et al. |
| 2007/0277269 | A1 | 11/2007 | Alexandrov et al. |
| 2008/0114160 | A1 | 5/2008 | Boukharov et al. |
| 2008/0206837 | A1 | 8/2008 | Vogels et al. |
| 2008/0227955 | A1 | 9/2008 | Hresko et al. |
| 2009/0081210 | A1 | 3/2009 | Evans et al. |
| 2009/0087878 | A9 | 4/2009 | La Rosa et al. |
| 2009/0093620 | A1 | 4/2009 | Kovalic et al. |
| 2009/0094717 | A1 | 4/2009 | Troukhan et al. |
| 2009/0123986 | A1 | 5/2009 | Williams et al. |
| 2009/0144848 | A1 | 6/2009 | Kovalic et al. |
| 2009/0208564 | A1 | 8/2009 | Li et al. |
| 2009/0229008 | A1 | 9/2009 | Bloksberg et al. |
| 2009/0238772 | A1 | 9/2009 | Vaishnaw et al. |
| 2010/0011463 | A1 | 1/2010 | Wiig |
| 2010/0017910 | A1 | 1/2010 | Ascenzi |
| 2010/0037352 | A1 | 2/2010 | Alexandrov et al. |
| 2010/0037355 | A1 | 2/2010 | Alexandrov et al. |
| 2010/0058489 | A1 | 3/2010 | Ikezu |
| 2010/0083407 | A1 | 4/2010 | Feldmann et al. |
| 2010/0162433 | A1 | 6/2010 | McLaren et al. |
| 2010/0168205 | A1 | 7/2010 | Meyers et al. |
| 2010/0286378 | A1 | 11/2010 | Li et al. |
| 2011/0008322 | A1 | 1/2011 | Zauderer et al. |
| 2011/0105347 | A1 | 5/2011 | Wu et al. |
| 2011/0126316 | A1 | 5/2011 | Yu et al. |
| 2011/0138499 | A1 | 6/2011 | Zhang et al. |
| 2011/0145946 | A1 | 6/2011 | Vinocur et al. |
| 2011/0158904 | A1 | 6/2011 | Albone et al. |
| 2011/0167514 | A1 | 7/2011 | Brover et al. |
| 2011/0177228 | A1 | 7/2011 | Alexandrov et al. |
| 2011/0179501 | A1 | 7/2011 | Croce et al. |
| 2011/0179519 | A1 | 7/2011 | Coruzzi |
| 2011/0179531 | A1 | 7/2011 | Kovalic et al. |
| 2011/0184045 | A1 | 7/2011 | Hartmann |
| 2011/0201667 | A1 | 8/2011 | Geisbert et al. |
| 2011/0209246 | A1 | 8/2011 | Kovalic et al. |
| 2011/0214205 | A1 | 9/2011 | Dietrich et al. |
| 2011/0214206 | A1 | 9/2011 | La Rosa et al. |
| 2011/0231959 | A1 | 9/2011 | Kovalic et al. |
| 2012/0017292 | A1 | 1/2012 | Kovalic et al. |
| 2012/0017338 | A1 | 1/2012 | Wu et al. |
| 2012/0023611 | A1 | 1/2012 | Cao et al. |
| 2012/0144520 | A1 | 6/2012 | McLaren et al. |
| 2015/0096077 | A1 | 4/2015 | McLaren et al. |

OTHER PUBLICATIONS

GenBank Accession No. AJ461376 (May 21, 2002).
GenBank Accession No. BM350754 (Jan. 16, 2002).
GenBank Accession No. BM351356 (Jan. 16, 2002).
GenBank Accession No. CC605134 (Jun. 18, 2003).
GenBank Accession No. CC671403 (Jun. 19, 2003).
GenBank Accession No. CC671410 (Jun. 19, 2003).
GenBank Accession No. CT854843 (Nov. 1, 2006).
GenBank Accession No. CT859984 (Nov. 1, 2006).
GenBank Accession No. CW395167 (Nov. 1, 2004).
GenBank Accession No. CW447049 (Nov. 2, 2004).
GenBank Accession No. CX111468 (Jun. 3, 2005).
GenBank Accession No. BG840928 (May 29, 2001).
GenBank Accession No. BG840889 (May 29, 2001).
GenBank Accession No. BG841093 (May 29, 2001).
GenBank Accession No. BG842208 (May 29, 2001).
GenBank Accession No. BG842452 (May 29, 2001).
GenBank Accession No. BG873755 (May 29, 2001).
GenBank Accession No. BG873856 (May 29, 2001).
GenBank Accession No. BG874013 (May 29, 2001).
GenBank Accession No. BM072886 (Nov. 13, 2001).
GenBank Accession No. BM073122 (Nov. 13, 2001).
GenBank Accession No. BM073865 (Nov. 13, 2001).
GenBank Accession No. BM073866 (Nov. 13, 2001).
GenBank Accession No. BM079064 (Nov. 14, 2001).
GenBank Accession No. BM333948 (Jan. 16, 2002).
GenBank Accession No. BM350368 (Jan. 16, 2002).

Yanagisawa et al., "Metabolic Engineering With Dof1 Transcription Factor in Plants: Improved Nitrogen Assimilation and Growth Under Low-Nitrogen Conditions," *Proc. Nat'l. Acad. Sci. U.S.A.* 101(20):7833-7838 (2004).

Martin et al., "Two Cytosolic Glutamine Synthetase Isoforms of Maize Are Specifically Involved in the Control of Grain Production," *Plant Cell* 18:3252-3274 (2006).

Osanai and Tanaka, "Keeping in Touch with PII: PII-Interacting Proteins in Unicellular Cyanobacteria," *Plant Cell Physiol.* 48(7):908-914 (2007).

Hsieh et al., "A PII-Like Protein in *Arabidopsis*: Putative Role in Nitrogen Sensing," *Proc. Nat'l. Acad. Sci. U.S.A.* 95:13965-13970 (1998).

Miller, M., Oral Presentation, "Global Transcript Profiles in Nitrate-Induced Roots of Maize Seedlings," Iowa State University Department of Biochemistry, Biophysics & Molecular Biology, Ames, Iowa (Dec. 8, 2006).

International Search Report and Written Opinion for PCT/US2007/082123 (dated Oct. 15, 2008).

Declaration of James McLaren (signed Dec. 2, 2009).

Forde, "Local and Long-Range Signaling Pathways Regulating Plant Responses to Nitrate," *Annu. Rev. Plant Biol.* 53:203-24 (2002).

Hirel et al., "Towards a Better Understanding of the Genetic and Physiological Basis for Nitrogen Use Efficiency in Maize," *Plant Physiol.* 125:1258-70 (2001).

Loudet et al., "Quantitative Trait Loci Analysis of Nitrogen Use Efficiency in *Arabidopsis*," *Plant Physiol.* 131:345-58 (2003).

Miflin et al., "The Role of Glutamine Synthetase and Glutamate Dehydrogenase in Nitrogen Assimilation and Possibilities for Improvement in the Nitrogen Utilization of Crops," *J. Exper. Bot.* 53(370):979-87 (2002).

Orsel et al., "Nitrate Transport in Plants: Which Gene and Which Control?" *J. Exper. Bot.* 53(370):825-33 (2002).

Quaggiotti et al., "Expression of a Putative High-Affinity $NO^-_3$ Transporter and of an $H^+$-ATPase in Relation to Whole Plant Nitrate Transport Physiology in Two Maize Genotypes Differently Responsive to Low Nitrogen Availability," *J. Exper. Bot.* 54(384):1023-31 (2003).

(56) References Cited

OTHER PUBLICATIONS

Thum et al., "Genome-Wide Investigation of Light and Carbon Signaling Interactions in *Arabidopsis*," *Genome Biol.* 5(2):R10.1-R10.20 (2004).
Wang et al., "Microarray Analysis of the Nitrate Response in *Arabidopsis* Roots and Shoots Reveals Over 1,000 Rapidly Responding Genes and New Linkages to Glucose, Trehalose-6-Phosphate, Iron, and Sulfate Metabolism," *Plant Physiol.* 132:556-67 (2003).
Wang et al., "Genomic Analysis of the Nitrate Response Using a Nitrate Reductase-Null Mutant of *Arabidopsis*," *Plant Physiol.* 132:2512-22 (2004).
Wullschleger et al., "Emerging Use of Gene Expression Microarrays in Plant Physiology," *Comp. Funct. Genom.* 4:216-24 (2003).
Liu et al., N_Geneseq_200812 Database, Accession No. ADX49734, US 2004/0034888, Feb. 19, 2004.
Liu et al., A_Geneseq_200812 Database, Accession No. ADY08501, US 2004/0034888, Feb. 19, 2004.
Verdoy et al., "Transgenic Medicago truncatula Plants That Accumulate Proline Display Nitrogen-Fixing Activity With Enhanced Tolerance to Osmotic Stress," Plant Cell Environ 29(10):1913-1923 (e-pub Jul. 2006).
Yanagisawa, Shuichi, "Improved Nitrogen Assimilation Using Transcription Factors," available at http://www.isb.vt.edu/articles/sep0401.htm, 5 pages (Sep. 2004).

PLANT GENES INVOLVED IN NITRATE UPTAKE AND METABOLISM

This application is a divisional of U.S. patent application Ser. No. 14/462,017, filed Aug. 18, 2014, now U.S. Pat. No. 9,523,099, which is a divisional of U.S. patent application Ser. No. 11/876,534, filed Oct. 22, 2007, now abandoned, which claims the benefit of U.S. Provisional Patent Application Ser. No. 60/869,290, filed Dec. 8, 2006, each of which is hereby incorporated by reference in its entirety.

FIELD OF THE INVENTION

The present invention relates to plant genes involved in nitrate uptake and metabolism.

BACKGROUND OF THE INVENTION

Nitrogen plays an important role in various plant functions, including metabolism, resource allocation, growth, and development (Crawford, N. M., "Nitrate: Nutrient and Signal for Plant Growth," *Plant Cell* 7:859-868 (1995); Marschner, M., *Mineral Nutrition of Higher Plants, 2d ed*., Academic Press Ltd.: London (1995); and Stiit et al., "The Molecular Physiological Basis for the Interaction Between Elevated Carbon Dioxide and Nutrients," *Plant Cell Environ.* 22:583-622 (1999)). Further, nitrogen is a major component of proteins and nucleic acids, as well as various secondary metabolites found in plants (Marschner, M., *Mineral Nutrition of Higher Plants, 2d ed*., Academic Press Ltd.: London (1995)). Therefore, nitrogen is one of the most important inorganic nutrients of plants. Inorganic nitrogen is added to many crop plants in the form of nitrogenous fertilizers (see Frink et al., "Nitrogen Fertilizer: Retrospect and Prospect," *Proc. Natl. Acad. Sci. USA* 96:1175-1180 (1999)). Nitrogen is principally added to the soil in the form of ammonia ($NH_4^+$) and nitrate ($NO_3^-$). However, estimates of nitrogen uptake efficiency have shown that between 50 and 70 percent of the applied nitrogen is lost from the plant-soil system (Peoples et al., "Minimizing Gaseous Losses of Nitrogen," In *Nitrogen Fertilizer in the Environment*, Bacon, P. E., ed., Marcel Dekker, pp. 565-606 (1995)).

The application of inorganic nutrient fertilizers is one of the major expenses incurred by producers of high-yielding crop plants (see Good et al., "Can Less Yield More? Is Reducing Nutrient Input Into the Environment Compatible with Maintaining Crop Production?" *Trends in Plant Science* 9(12):597-605 (2004)). Further, reports have indicated that nitrogen-based fertilizers may be associated with environmental damage (see Vitousek et al., "Human Alternation of the Global Nitrogen Cycle: Causes and Consequences," *Ecol. Appl.* 7:737-750 (1997)). Therefore, one important way of decreasing the amount of inorganic nitrogen that is applied to plant crops is to develop ways to improve nitrate use efficiency ("NUE") in plants.

Traditional plant breeding and marker-assisted selection are techniques that have been investigated for developing and identifying plants with increased NUE (see Good et al., "Can Less Yield More? Is Reducing Nutrient Input Into the Environment Compatible with Maintaining Crop Production?" *Trends in Plant Science* 9(12):597-605 (2004)). However, these approaches are often time-consuming and labor-intensive. An alternative approach is to use genetic engineering techniques to develop transgenic crop plants that have enhanced NUE. This approach requires the identification of genes that enhance NUE. Efforts have been reported regarding identifying genes that are regulated by nitrogen levels in *Arabidopsis* (Scheible et al., "Genome-Wide Reprogramming of Primary and Secondary Metabolism, Protein Synthesis, Cellular Growth Processes, and the Regulatory Infrastructure of *Arabidopsis* in Response to Nitrogen," *Plant Physiol.* 136:2483-2499 (2004)). However, there is a need to identify genes that are involved in nitrate uptake and metabolism in economically important crop plants such as corn.

The present invention is directed to overcoming these and other deficiencies in the art.

SUMMARY OF THE INVENTION

The present invention relates to nucleic acid molecules from corn (maize) that are modulated by nitrogen (e.g., that up-regulated by nitrogen). The present invention also relates to isolated proteins or polypeptides encoded by the nucleic acid molecules. The present invention further relates to promoters of the nucleic acid molecules of the present invention.

The present invention further relates to a nucleic acid construct having a nucleic acid molecule of the present invention (i.e., a nucleic acid molecule that is modulated, e.g., up-regulated, by nitrogen in corn). The construct also includes a 5' DNA promoter sequence and a 3' terminator sequence. The nucleic acid molecule, the DNA promoter sequence, and the terminator sequence are operatively coupled to permit transcription of the nucleic acid molecule.

The present invention also relates to an expression system, host cells, plant cells, plants, and plant seeds having a nucleic acid construct that includes a nucleic acid molecule that is modulated by nitrogen in corn.

Another aspect of the present invention is a method of expressing a nucleic acid molecule that is modulated by nitrogen in a plant. This method involves providing a transgenic plant or plant seed transformed with a nucleic acid construct having a nucleic acid molecule that is modulated by nitrogen in corn, a 5' DNA promoter sequence, and a 3' terminator sequence. The method involves growing the transgenic plant or a transgenic plant grown from the transgenic plant seed under conditions effective to express the nucleic acid molecule in the transgenic plant or the plant grown from the transgenic plant seed.

Another aspect of the present invention relates to an isolated DNA promoter from corn suitable for inducing nitrogen-regulated expression of a protein encoded by an isolated DNA molecule operably associated with the DNA promoter. The present invention further relates to a nucleic acid construct including the isolated DNA promoter, as well as expression vectors, host cells, plants, and plant seeds containing the nucleic acid construct. The present invention also relates to a method of directing nitrogen-regulated expression of an isolated nucleic acid in plants. This method involves transforming a plant cell with the nucleic acid construct described in this paragraph and regenerating a plant from the transformed plant cell. By this method, expression of the nucleic acid molecule, under control of the DNA promoter, occurs in the plant and is upregulated by nitrogen.

Nitrate use efficiency affects both grower profitability and the ecological sustainability of intensive corn production. The present invention is effective in providing a means to improve the NUE by enhancing the nitrogen uptake of crop plants such as corn. In particular, the nucleic acid constructs of the present invention can be used to develop corn germplasm using marker-assisted selection and/or transgenic approaches. Thus, the present invention is useful in increasing the nitrate absorption and usage efficiency by crop plants and thus reduce the use of nitrate supplements. The nucleic acid constructs of the present invention include nucleic acid molecules corresponding to genes of corn plants and, hence, have the most direct bearing on nitrate metabolism in corn. Therefore, such genes may be more directly relevant to corn improvement than genes from non-crop plants such as *Arabidopsis*.

DETAILED DESCRIPTION OF THE INVENTION

The present invention relates to nucleic acid molecules (e.g., genes) from corn (maize) (e.g., from B73 seedlings) that are modulated (e.g., up-regulated) by nitrogen (e.g., in the form of nitrate, calcium nitrate, etc.). These genes and their promoters are natural targets for use in corn improvement. These genes can be used to improve corn germplasm with the use of marker-assisted selection and/or transgenic approaches. The present invention provides nucleotide sequences of the full-length cDNA clones of such genes. The present invention also provides the amino acid sequences of the isolated proteins or polypeptides encoded by these genes, as well as their putative promoters (upstream of transcription start site of the genes).

A suitable nucleic acid molecule of the present invention is a gene that is up-regulated by nitrogen and contained in a full-length cDNA clone having the nucleotide sequence of SEQ ID NO:1, as follows:

CGACTGGAGCACGAGGACACTGACATGGACGGAAGGAGTAGAAAATATTG

CCTGCTCCGACGACCTTGAATATTCACTGGCCATTTAATTTCTACTTACA

AGCCTGAATGAGCTAGAGATCCATCTGCTTCTGTACGTGCTCGTCAGGTA

CGCTCGTAAAAAGAAAAGAAAAAAAAAAGAAGAGATCGAGATCGATCTGTT

GACGACGCCCCCGTCGCCGATATGGGCGACCTCTCTGTCGGCCACAGC

CGCCGCTGGTGCGGCCGTTTCGCGGCCGTCCTTTGCCTGTGCGCGGC

CTTCTGCAAGCCAGATGAACTCCCGATGGATCCACTGCCGAACTTGC

CGCCGACGAGGTCGCTGCAGTGCTTCGAGGACGAACAGGTGTACAGC

TGCTGCGAGGGCGCGTACAGGCTAAACCCATCGGGAATCATCGCCGT

TCCCGTCGGCGCGGTGGACTACTACTGCGGCGGCGCGTGCGTGGTGG

AGACGGAGGACGTGCTCAACTGCGTGGCCAGCGCCCTGGACGGCTTC

GCCTTCTACAACGGGGCCTCCGTGGAGGACGTGCGCTACGCACTCAG

GCGGGGCTGCAGCCACACCGCCAGAAGAGGCGACTTCAACGATTTGG

AGCCGCATCTGGGCGACTACCCTGACATCTATGGCGACGATGATGAG

CACAGCTTTGGCAGCAAGGTTGTTGCAGCTCCTCTGAGGTTGCTCGC

GTTTCTTGGCGGTGCGGGGCTGTTCTTCCTGGGCCCTTGA

(Underlined = GeneRacer Oligo sequence; Bold/Underlined = start codon; coding sequence in bold) (Sequence of 5' RACE product CW13E07-Full_Length cloned into pCR4-TOPO) (derived from MEST13-E07, GB_ACC# BG840928)

The predicted protein or polypeptide encoded by the full-length cDNA clone of SEQ ID NO:1 has an amino acid sequence of SEQ ID NO:2, as follows:

MGDLSVGHSRRWCGRFAAVLCLCAAFCKPDELPMDPLPNLPPTRSLQCFE

DEQVYSCCEGAYRLNPSGIIAVPVGAVDYYCGGACVVETEDVLNCVASAL

DGFAFYNGASVEDVRYALRRGCSHTARRGDFNDLEPHLGDYPDIYGDDDE

HSFGSKVVAAPLRLLAFLGGAGLFFLGP

A putative promoter (upstream of the transcription site of the gene) for the gene of the full-length cDNA clone of SEQ ID NO:1 has a nucleotide sequence of SEQ ID NO:3, as follows:

ccgcaagagggagtctttaccgagtgtcacctaatacgcttggcgaagga cctggtaaaagggcccacagggagctttttgctaagtgtctgtacagtgg acactcggcaaagagtgagcctttgccgagtgtcactccgtcaccgttac ctggtgtcgtgacgacggcttttctttgtcgagtaccgagtgacactcga caaaacctttgccgagcgtccgataaaaagtattcggcaaagaagccgtt gccgtctttgccgagtgttttccagactttgccgagtgtttcagacactc ggcaaagaacctgattccgatagtgaaggtcttacaccccgatccacccc aattcgtgcgtattggagcaagtacccaaacaaaaccgtactgggaataa ttacctccgttcgctgcagtttgcagaacagcagttcaatgctacaggac gacgcagctgcagcgaacatgcatgcatttgaactcactccgttcactga tggacaagaggcatctgggtgactaataaaagaacgacacacacggacag cttctagaagtattggtagcgcatgaacaacaatgccgctgttagcttgt actgaggcacgaaacatgaatctgacctactactgacttctactataata atagtatatagtatggccaggccaggccaactccggcgaaaacgggagta cgcatgcagatggagcggcacattagtaggctgtttggtttgaagaatgg gctagtctatcatcttctcactctccactttttttgtttggtttgtggaat gaaatgagttgattcatcatcacctcattccttatagttagttagttagt actaatatgaggaatatggtcatcccaccaaatttgaggaatggatccac gatgtaccaccacattttgcatgaagtgattcctcaaaccaaacaccccc aaatgtaaaccgagtcatgcctccgatcccaaccttcgtgtttcccacca aacacacgcgtacagaggccaagcacacgcacaaaagcaagcctcgatcg tagcccgtgcctaaccctgccgatgccgtaataaacttgtgtgctccacg caaccatgaaatgaacctagaaatcgcaggggcgggatgcgagtgaaaag gagcgggcaggtcaggtaggtttgaactctctcctataataatcctagct agcacacttgcccagattatattgcctgctccgacgaccttgaatattca ctggccatttaatttctacttacaagcctgaatgagctagagatccatct gcttctgtacgtgctcgtcaggtacgctcgtaaaaagaaaagaaaaaaaa agaagagatcgagatcgatctgttgacgacgcccccgtcgccgatatggg cgacctctctgtcggccacagccgccgctggtgcggccgtttcgcggccg tcctttgcctgtgcgcggccttctgcaagccaggtgcgtgctcaccgtca acacacgcaccattattccaccctcccaaggagcacagtacaacgcacgt acatatacctctcctcaatcgatatatagttacgtcttacgtactatcta gttaatctatcacgttgatgtctaatatagactccgcatggcatatgcat -continued gcagatgaactcccgatggatccactgccgaacttgccgccgacgaggtc gctgcagtgcttcgaggacgaacaggtaagctaacaagcaagagcgtgtt tggtttcatgctaggacagagttgcataccacgtagctatcataagccta ccacacgtagctatcacagcctgtcgatttcgttcggtcgcctgacggta aacatcgctgcccgagaggcgagctcttttgacaagcctcgacgaacca aataagccaagtcctactgtacgagggcgatcgaggcgccgaggcctgtg tgatgtgatgccgtgtgtcgtggtcacccaccagctgctgtgtacattgg tccccgtgccgcgcgtcgtaaccgcatgcggcatgccgctgcatgcaggt gtacagctgctgcgagggcgcgtacaggctaaacccatcgggaatcatcg ccgttcccgtcggcgcggtggactactactgcggcggcgcgtgcgtggtg gagacggaggacgtgctcaactgcgtggccagcgccctggacggcttcgc cttctacaacggggcctccgtggaggacgtgcgctacgcactcaggcggg gctgcagccacaccgccagaagaggtccccaagtttctcgcctactagct catctctctctacgtaccagccaagctagatcgactaccagtctccgcag cagtgcattcggaacgaccgctgacaaactgacaggctcgtgttcctgtc agcgcaggcgacttcaacgatttggagccgcatctgggcgactaccctga catctatggcgacgatgatgaacacagctttggcagcaaggttgttgcag ctcctctgaggttgctcgcgtttcttggcggtgcggggctgttcttcctg ggcccttgaacgaagatataaaagaactagcgatgtgatccgcgtaaata tatactccgtatatagcatgacatgagtatctagtttgtcttatatggta aaccatactaaattttcttgtatggcattaaaaaaaattaagactttatt tagttatttgactagttgttctctctggatcctctaatcagttcgaactc tataagctttttttattccactcctatctagaggtcgcataatatgctaag gtgagatcttgatgtctttcgtttttttaactcgataaagttgttgtgag tctctcttataaaattattttaatgctaatattagattttagtcagaga tatgcagttgaccgttttgcactaaaatatttttgaatttactatagtat tagttgtctactaatcacagctaaaaccgtttttatttttagttttttta taacagaaaaaatatctctggaaacgaaaacggcaacacagtagttcaaa aatatcgaagacaataatttaacatgaaaaatatatatgtaatgatcgga atctaaaaaacaatcactaaatataaacatatagtaacatgtactctcaa ttgacctgaaaaaagcacataacctatagatccacaaagtaacgaagatt gaagcatgaaaaatagaccatcatacattaaagggttgtgcttatttagc tctagaataacctccttaagagcaacttcatttgcaacaacattgtctag agttaaagagaatattttcttctctgtaaaccatttcaataagcatgaac tgggtctaagagacaaattcttaccgttgtgccgacccagaacatgatcg aaatttgtaattcgcttctgtatttgtgaatcatcatctacccaatgtac catgatacacatgtaccttttattctgatttgatatccacatctccatgg tagcactgaagtgacaattaagggttttaaaaaatttatacaacacatca tttttatgcaaaagagatccattacttcttttctaacaatgacatgtgac tttatagaaaatataggctttaaaggtttaatgaaatccataaagtattc atgttcaagaatgttaaatgggtactcatgaatgataatagtagtataaa -continued acttcctcaaactaattgactcgtcatatttatatggttggacaatatat agatatacctaccttatgatctttttctgatttgagctcctgctatctta gtaaaaccttatgataacgcttctaatgcaaccaaaactaagttgttcct ctatggcttttagcactacctttgtaagtcctatttttgtagctcagaaa ctttcatttggcccaaatttgctccagagatttgcaattcccctccacta caacaacatacaaatcaaaatactgccaaacatctaaagtatacttattt gctactttatggggtgctcatcaacattagattcact (>MAGI4_8075 MAGI4.contigs_w_singleton.fas 4037 bp)

A suitable nucleic acid molecule of the present invention is a gene that is up-regulated by nitrogen and contained in a full-length cDNA clone having the nucleotide sequence of SEQ ID NO:4, as follows:

GGACACTGACATGGACTGAAGGAGTAGAAAATACAGAACCCTGCAACTGC

AAGCTAAGGAGAGTGTGATCACCAACAGCTAGTGCTAGTCCCCCTTCCTT

CCATCCATCCATGGCATGCGTCAGCACCTTCCAGAGCTGCCCCATTGCCA

GAAGAGCAAAGATCAACACCAGGTCCAGGGGCAGCAGCAGTAGCGTGGCG

AAGGGGTCACCACCACCAGCCTTCCAGTTCCAGTGCAGGGCGTCGACTTT

CGCGGCGGACACCAGCCTCCGGCTCGAGCTGGACGAGAACCCCGAGGCGA

TCATCTCGGGGGCGTGGCCCGGGAACTGCTCCCTCCTCAGCTACGACGAC

CTCCGCGCCTACCTCGAGTCGCAGGAGACGGCGGCCCAGGCAGACGATCA

GCGCGGCGTGGCGCTCCTGAGCGAGACCATGTCCACACCCGTGCTGGTGG

CCACAGCAGACCAGACCCTGGAGGACGTCGAGTGCCACTTCGAGGCCGTG

TCGGGGCTTCCGGTCGTCGACAGCGGCCTCAGATGCGTCGGGGTGATCGT

CAAGAACGACCGGGCAAGAGCCTCTCATGGGTCCAAGACGAAGATATCGG

AAGTGATGACATCTCCAGCTATCACACTATCGTCTGACAAAACCGTGATG

GATGCTGCTGTTCTCATGCTCAAGAAGAAGATCCACAGATTACCAGTTGT

AAACCAGGACGAAAAAGTAATAGGTATAGTTACCCGCGCTGATGTTCTTC

GCGTGTTGGAAGGCATGTTGAAGATTTAGGAGCGCAGATACCCATGCTCG

GAAGCCACAGCCTCTTGTAAATATGTAGATGTGCCCGGGCATGGTGTTTC

TGAGTAGCAGCAAAGAGATCTACCATGTATAGGAGTTTCTCCTTGTAAAT

AATAGTAGCACGCCAGGAGACTCCATCCCAGG (Underlined = GeneRacer Oligo sequence; Bold/Underlined = start codon; coding sequence in bold) (Sequence of 5' RACE product CW13A08-Full_Length cloned into pCR4-TOPO) (derived from MEST13-A08, GB_ACC# BG840889)

The predicted protein or polypeptide encoded by the full-length cDNA clone of SEQ ID NO:4 has an amino acid sequence of SEQ ID NO:5, as follows:

MACVSTFQSCPIARRAKINTRSRGSSSSVAKGSPPPAFQFQCRASTFAAD

TSLRLELDENPEAIISGAWPGNCSLLSYDDLRAYLESQETAAQADDQRGV

ALLSETMSTPVLVATADQTLEDVECHFEAVSGLPVVDSGLRCVGVIVKND

-continued

RARASHGSKTKISEVMTSPAITLSSDKTVMDAAVLMLKKKIHRLPVVNQD

EKVIGIVTRADVLRVLEGMLKI

A putative promoter (upstream of the transcription site of the gene) for the gene of the full-length cDNA clone of SEQ ID NO:4 has a nucleotide sequence of SEQ ID NO:6, as follows:

caacgtggagtaggcaagcgttggtcttggccgaaccacgggataaacca ctgtgtcaactctgtgattgatctcttgtggtattgtgttttgttgagac tcttttctagccacttggcatttagtgtgctaacacttaacaagtttttg tggctataagtttaagttttacaggatcacctattcaccccccccccctc taggtgctctcaagttgacaggtgtctccatggtgcctaattgagccgtt cttttacgctatccattcgattggtttggtgggtatgtgtggtctggctc ttgcgatgtttgcccgctggaaacgaaacaatcgtgcatacgtgcgcatg caattaacggtggtgtttttggcctgtcttgcagcagcgggtgcagcatt ggcttggcataagcacgcaaccaaacaaagactaccttttggtcaatgca tgcgaagaatctgtacgagcgggcgtagacaaccaatgatgcgatataaa atttaaggattgaatcatattagaatcgagctttatttctattcattttc gaactaatttttaagtatcctaacttattgtgaagaaacgtaaatattt agatcccgatccattaccacctctactcatacgtgaaaccaaacacgcgg aatatccttctggttcaaatatgcagaagtcaatgagcaggacttctgct tgtttgttcagtctctcaggcagggttacaggaggcaatacaagatgttc tccaacgattccctgaatcgttcacccctctctcagtcctatgattcac tcactcacccctccccctcttctccgtatgacaggaaatcccccctagagg gggagagctctaagctcccctccactaattaatcatatttactgtgaaa ttacctatttgtagtgtaattaatagttagcaatgtgtattacgtattat aaatattgtaccaatatttaaaactcaaaaaactaatgtataaaaatcaa atagtgcacttaaagtattaagggcagagctgaataggggggattgttgga gaagtgaagaaatagggggaagaatagttgagaaggggtatttaaatatg aatagaaagtatgaatggagggaatgtttggagagagctcaagaacaagg gacactgagctgcctacaacacgtggccctttttgtccctcttctttttt ttctttcgcatctgctggctacaagaggacacgcccttctattcgccgta tagagcagtgtctgtgaagtaaaagagaactatcctccaaggcttatttt gagtgtattactcctggattcttgaatcttagctggtatggtatggtaag gagttacgttgtccaggagattccaacttacggatccacactgaaaagtt tgtattacccatttgttaggccccgtttcaatctcacgggataaacttta gcttcctgctaaactttagctatgtgaattgaagtgctaaagtttagttt taattaccaccattagctttcctgtttagattacaaatggctaaaagtag ctaaaaaaagctgctaaagtttatctcgcaagattggaacagggcctata tggtcactttagagaggcatggaggtttaatagactatgacattcgtacg tggtcacctcaacaaactttattgtttgaccgaaccatagattgaattgt gtgacattgttctttgctcgtattattattaatagaaagtaaccttcttg -continued ggtgcggcccatacggtcctgagcgcactaaatgaggcctcattggccgc ggcccattcgatcctcaacgcactggataaagccagcgtggcgtggctaa accacttcgtttggcatgggcctgtcggtgcacttgcccaaaccatgagc ttgtaccaaaactcgctagtggtagtggtattagtagtgaagaacttctg caacttcaaactcaccgattctctcgcggtcagtttggaagctaaaatat cggtggaaattagagagaatttgataagctaaaatctctttattatttaa aattgaataataaataaattttaactcctccaatcttctccgtttttatg tctcccaaactcagtgtaccagatcatattcctttcattaaaaaaaaggt gaacaaagacgccaccttatccactgccacgtgacaggggggccaggggaa tctcggcggccagtggcggcacgccacgccggccggtcgcccccgtcgct gtacaagatacccatgattggagcggggcaggtgcagagcagcaacgcca cggctgcatgagatcaagaagctgccttcacttcgccccactgcagcatgc cgtgtcgccgtcagagttgggcgcatatccagataaaaaaaacttgcctg cttgcactgcagatgcgttgtttttgctaacagcaagcaggcaagtcagc agcctaaccttctttgatatttacagagaagatgaaaaggagaactggag agcagtagtggcagtcacttcactggtcaagcattcctatccacctcggc ccacctccacctccctgacagtcattttgttatataaaacccatcaagct cccctgcaaggagatacagaaccctgcaactgcaagctaaggagagtgtg atcaccaacagctagtgctagtccccttccttccatccatccatggcat gcgtcagcaccttccagagctgccccattgccagaagagcaaagatcaac accaggtccaggggcagcagcagtagcgtggcgaaggggtcaccaccacc agccttccagttccagtgcagggcgtcgactttcgcggcggacaccagcc tccggctcgagctggacgagaaccccgaggcgatcatctcgggggcgtgg cccgggaactgctccctcctcagctacgacgacctccgcgcctacctcga gtcgcaggagacggcggcccaggcagacgatcaggtacacttcgatctcg cggcttcttcagttcttgttaccattgtttacatctcctccagctcttgc taacccggcctggacgggtctcctcctctgtggatatatacagcgcggcg tggcgctcctgagcgagaccatgtccacacccgtgctggtggccacagca gaccagaccctggaggacgtcgagtgccacttcgaggccgtgtcggggct tccggtcgtcgacagcggcctcagatgcgtcggggtgatcgtcaagaacg accgggcaagagcctctcatggggtcagcacctcgctcctctccctccac ctctttctttctcatggggccagggccatgcatgcgcatcaagctgctag tttctcatagacaggcaaataagaacgacgtacgtccgttcagtttaccg gtctgtttctacttgtgacagtccaagacgaagatatcggaagtgatgac atctccagctatcacactatcgtctgacaaaaccgtgatgggtaatcttt tttgcatcgcttttcttttcttttcttttcttttctgttcatgtgtgatt tttaacaagttgaatctaacagtgcatgcctaacgtctacagatgctgct gttctcatgctcaagaagaagatccacagattaccagttgtaaaccagga cgaaaaagtaataggtacggtgagtgagtgtcagaatgctcacaagccag cagagattaaaaaaaaaaaactgcatgccatacacttaattagtattatcc -continued ttaattatcattgacaacacagagattatatgttgcaagggctaatgggg
ttctaaacactgtcaacaggtatagttacccgcgctgatgttcttcgcgt
gttggaaggcatgttgaagatttaggagcgcagatacccatgctcggaag
ccacagcctcttgtaaatatgtagatgtgcccgggcatggtgtttctgag
tagcagcaaagagatctaccatgtataggagttctcc (>MAGI4_31359 MAGI4.contigs_w_singleton.fas/ 3987 bp)

A suitable nucleic acid molecule of the present invention is a gene that is up-regulated by nitrogen and contained in a full-length cDNA clone having the nucleotide sequence of SEQ ID NO:7, as follows:

CGACTGGAGCACGAGGACACTGACATGGACTGAAGGAGTAGAAACCCTTC
TCGCTCGGTTGCTCGGGAGCTTTCCCCTTCCTGTTCCTGAAGCTTCCGAC
ATCCGACCGCCTCCTCCTCCTCGTTCTACTCGCCGCCCCTTCTAGAATCA
TCCAGAGGCGTGCCGGTGAAGCGCGAGAGCGGTGAGGCATGGCGATGCAG
ACGGGGGTCGCGACCTCCAAGGTCCTCATCCTCGTCGGTGCAGGGATGAC
GGGCTCGATCCTGCTGCGGAATGGCCGCTTATCTGATGTGTTGGGAGAAC
TCCAGGAGATTATGAAGGGTGTAAATCAAGGAACTTCTTCGGGTCCCTAT
GACATTGCACTTATTCAAGCTCAGATTCGGAATTTAGCGCAAGAAGTCAG
AGATTTGACATTGTCAAAGCCCATTACCATACTGAATGGCAAATCTGACT
CGGGAGGCAGTTTATCATCCTACATACTGCCAGCAGCAGCAGTTGGAGCA
ATGGGTTATTGCTACATGTGGTGGAAGGGGTTGTCTCTCTCAGATGTCAT
GTTTGTCACAAAACACAACATGGCAAATGCTGTTCAGAGCATGTCAAAGC
AGTTGGAGCAAGTTTCATCAGCACTAGCTGCAACAAAAAGACATCTAACT
CAACGGCTTGAGAATTTGGATGGCAAAATGGATGAACAAGTAGAGGTCTC
CAAAGCTATTAGAAATGAGGTCAATGATGTTAAAGATGACCTGTCTCAAA
TTGGATTTGATGTCGAATCAATTCAGAAAATGGTTGCTGGATTGGAGGGA
AAGATCGAGTTACTTGAGAACAAACAGGACGTGGCTAATACTGGTATCTG
GTATCTCTGCCAAGTAGCAGGCGGTTTAAAAGATGGAATAAACACCAGGT
TTTTCCAGGAAACCAGTGAGAAGCTGAAGCTCTCACATTCAGCTCAACCT
GAAAACAAGCCAGTGAAGGGGCTTGAATTTTTTTCGGAAAGCACCATGGA
ACAGAAAGTAGCTGACTCCAAACCAATTGCGGTGACAGTCGACGCTGAGA
AGCCTGAGAAAACCGCTGCTGTAATGGGCACCACAGTGCACAGGTCTATC
AGGTTCTCATATCGGAAGGCAGGCCTTGCTTTGTGATCAAATCCTCTCCG
CTTGAGATGCACGTGGCCTTCCTGGTTG (Underlinded = GeneRacer Oligo sequence; Bold/Underlined = start codon; coding sequence in bold) (Sequence of 5' RACE product CW15E10-Full_Length cloned into pCR4-TOPO) (derived from MEST15-E10, GB_ACC# BG841093)

The predicted protein or polypeptide encoded by the full-length cDNA clone of SEQ ID NO:7 has an amino acid sequence of SEQ ID NO:8, as follows:

MAMQTGVATSKVLILVGAGMTGSILLRNGRLSDVLGELQEIMKGVNQGTS
SGPYDIALIQAQIRNLAQEVRDLTLSKPITILNGKSDSGGSLSSYILPAA
AVGAMGYCYMWWKGLSLSDVMFVTKHNMANAVQSMSKQLEQVSSALAATK
RHLTQRLENLDGKMDEQVEVSKAIRNEVNDVKDDLSQIGFDVESIQKMVA
GLEGKIELLENKQDVANTGIWYLCQVAGGLKDGINTRFFQETSEKLKLSH
SAQPENKPVKGLEFFSESTMEQKVADSKPIAVTVDAEKPEKTAAVMGTTV
HRSIRFSYRKAGLAL

A putative promoter (upstream of the transcription site of the gene) for the gene of the full-length cDNA clone of SEQ ID NO:7 has a nucleotide sequence of SEQ ID NO:9, as follows:

taactctacaagctaagaatcaacatgtatgcaattccataataatcggg
catcatctatcactcattgctaacttcagcactgaacatgatttcaagag
tttttagcagaactactatgcgggtgatctcctttcagatgtagatggtt
tagaagtgtacataagcttgcaggggcttaaggaactgtttatttaatct
tctgtgagcacgaacatccatagaagaactatctgaactgaagctaaaga
tttgcatgaaatggtaatttgtacacattaagtgcatcatgcaaacagaa
cgagtacacagtgaaacgatacagacctcccgagtcagatttgccattca
gtatggtaatgggctttgacaatgtcaaatctctgacttcttgcgctaaa
ttccgaatctaatatcaagcacgagcatgcaaagttaagtagaaatgaat
aattttaccgagatggaaagaagcaagagaaacttctaagcagatgctga
cactgagatagtgagatgtaagatgtattccatatgaggaagagcatacc
tgagcttgaataagtgcaatgtcatagggacccgaagaagttccttgatt
tacacccttcataatctcctagaaacacaaaaggtacatcattgccttaa
ataaacatttactaggaagtttcagagcataccatcaaaatctgtatgat
atgtatcaggaatcactaactagtgaagcataagttatggtacgcaaaac
ttccgagtgccaattgggcgttgatgtaattttatcacatggtgttaatc
acatccacatatagacagaatcaacgcttctagtaccccatcgccaagtc
attcaaaaaatatcaggtatcagctatctgacaacgctcaactatccaaa
ccgtatgaaagtgcgtgtaatcaaaatgaacatatttttttcggggttgg
gtgtgggggtataccgacctggagttctcccaacacatcagataagcgg
ccattccgcagcaggatcgagcccgtcatccctgcgaggacaccatttca
ccacgtaaggtgtcgaaacaacagccgattggggaaaatagcatcaaatc
cgagagagatttgatgggggcgagaggtcgatggcggtgatgagaagagg
acctgcaccgacgaggatgaggaccttggaggtcgcgacccccgtctgca
tcgccatgcctcaccgctctcgcgcttcaccggcacgcctctggatgatt
ctagaaggggcggcgagtagaacgaggaggaggaggcggtcggatgtcgg
aagcttcaggaacaggaaggggaaagctcccgagcaaccgagcgagaagg
gtgcctggacccgggaccgggacctgagaatttcgtgtgtcacaaacaaa
cagggtgaaccagttgtgaaatgggaccacgtgtcagtgaagaggtgagt
agtagtatttgtgagttgtgactcgagaaatgccgctgcgggctgcggcc -continued tagccacagccacgtcagcaatgtcgaaagtcgaaaccaaccccactcca cgtctcccccaggagaagcgaccattcaaagccgccgggagctcggcgtc accgccgcgagctcgacacctcgacacctcgtgccgccgcagcgcttgct ttcgtccccccttacgccactcccacttggccacttcagccaccatctccc tgaagctagtggctaacctcctcaccgccatgggcacccctctcctcatc ccccttctcgtcaccctccagctgttcactacctcctcccccgcggtcgc gtcgtcacacatctccgccatcatctcgcagtcgggcctcgacttcgcca aggacctgctcgtatcccatgccgttgcgaccctcacgcccatgaacgtg ccggacatcgagaggaccatgagcatacccctcgtgggcaccgtccgcat ggccgcatccgggattgtgctccacggcctcgccgtcaccaactccaccg tcgctgtgggggacgcgggtgttgtcgtggccgcctcgttggccagcgcg aacctcaccatggagtggaactactcgtatgacgcctggattgtgaccat atccgacagcgggaatgcttcggtccaggtataaatgaggggaacatata ctgtgcagtcatattagtgcaaccgtgcaattaagcaatgatgcatcgat ccaatcaaaatccaactatgattgctattttaggtggaacatggttagat gcaaaacagtcctgtttggttgatattcgatattccatcagttatgttcc ccaaggcgtggcttgctgattggtggctgttaattgaatcataagatact gcccgtttttttaatatactgagtaggagatatacgcatcttttatgcta ttaagtatagactgatcgcgcgacacttgaattttggaatatctattttc tgtcagatgtcagaagtagaatcaattatcttagaagtgggtgctaattc acacctattactatatttaaaatgggattaatataaacactctatttttc tcgaaagcgcaagagagctgcgcgaaaatatattaagaagaagtaaaagg tccaaaaggaccccaagatacagataaggccgacctacggcggccaataa caagcataaatgaaaccatccatgacaaaaacactgctaccagaacagca ctacatctatctagctaacaggtagacctgggatagggggcagtaagcaag gacagcttctttgcaccagccataacccaaagatcaatctccaaaccaac acttctaatagcaacagcaacactaggactcttattgtcaaaaacgtagc cattgcgatgtttccaaagggtccaaacaccaagaatgacaagagaatta agaccatttcttgcaatcccaggagtcttggtgatcaagtcttgccacca atccataaaaacctcttcacaggactgatgggccaagtgttgtagattta caagaagaagcagcttgaaccaaaattctctagcaaaaacgcagcccagc agcatatgatttaaggtttcctgatcctgatcacataatggacatctctc cggatgatccatacctcttctttgcaacctatcagctgtccacaccttct tgtgagcgaccaaccacatgaaaaatttagatttcggaggagcccaagtc ttccaaattatatgaaaaggctcaaactcaattgacccaataaagaaacc cctataagcttccttggaagaatattttccattggcagcaaggcgaaaga aatgcttgtcttcaacatgaggtcttagctgaaccaaatctaataaatcc cacaagaggagatactcgttgatacacccactgaa (>MAGI4_20155 MAGI4.contigs_w_singleton.fas 3385 bp)

A suitable nucleic acid molecule of the present invention is a gene that is up-regulated by nitrogen and contained in a full-length cDNA clone having the nucleotide sequence of SEQ ID NO:10, as follows:

CGACTGGAGCACGAGGACACTGACATGGACTGAAGGAGTAGAAAAACTCC

CAAATCCTTCGTTTCGTCGTCTCCACACGCAATAGCATCCGAGCAAAGAA

GCCAAAGAGCAACTGGGAGCGAGGACGGGAGGCAACAAGCGGCGGCGGCA

TGGACCGGAACCTGAGCGGGTTTCTGATCGGGTGCCTGGGCGCCGCCGTG

ACGCTGCTGGCGTACCAGCAGACGGTGGTGACCAGCACGCAGAGCGTCGC

GGCGGGCTTCGTCGTCATCCTCTTCGCCCTCTTCGTCAAGGAAGGATTCA

TTTCCCTCTGAATCTCTGGTGCGCGTCAGCCAGCCATGCATGAGGAGGCG

TCATCGCTCCGCTGCCTGTATTTCTGCTCGCTAGTTCAGTCCCGCAGCTG

CCGCTGTGCTCGTCAGGTTC (Underlined = GeneRacer Oligo sequence; Bold/Underlined = start codon; coding sequence in bold) (Sequence of 5' RACE product CW28B08-Full_Length cloned into pCR4-TOPO) (derived from MEST28-B08, GB_ACC# BG842208)

The predicted protein or polypeptide encoded by the full-length cDNA clone of SEQ ID NO:10 has an amino acid sequence of SEQ ID NO:11, as follows:

MDRNLSGFLIGCLGAAVTLLAYQQTVVTSTQSVAAGFVVILFALFVKEG

FISL

A putative promoter (upstream of the transcription site of the gene) for the gene of the full-length cDNA clone of SEQ ID NO:10 has a nucleotide sequence of SEQ ID NO:12, as follows:

gatacgactctcgctggtatataaaatctgtttcgtagataaacatgaaa ccagaatttttgatcaccatatacttgtttcagaagcaaattggggacac catatacttgttgccttcaaacgaccgtacaataagttcagactgaccat ctgaatgtcacaagagctagtttagagcagcaagaaattgtcaagtgacc tagacatcccgaaccgacgcttcccagacttagcccgaccttccgggtcc ttcataagctgactccgtggcccctcaccagaccaacgccgcagccgttg accttgcggctttttatccccatccggccatccccaacccaactcccaaa tccttcgtttcgtcgtctccacacgcaatagcatccgagcaaagaagcca aagagcaactgggagcgaggacgggaggcaacaagcggcggcggcatgga ccggaacctgagcgggtttctgatcgggtgcctgggcgccgccgtgacgc tgctggcgtaccagcagacggtggtgaccagcacgcagagcgtcgcggcg ggcttcgtcgtcatcctcttcgccctcttcgtcaaggaaggattcatttc cctctgaatctctggtgcgcgtcagccagccatgcatgaggaggcgtcat cgctccgctgcctgtatttctgctcgctagttcagtcccgcagctgccgc tgtgctcgtcaggttcttggaaaaatactgtaatagcgtagtgactttta tgtacgacacggatggttgttgctggctgaagggtctactctgtcgaaat cgatgtatcttagtttatgctacttgaagaacagcagactgcagatcagc -continued

```
agagttcttgccttcttacgctaattaataattattggtacacgaatcct
gattgtgttgagccttcttgccgttgctccttccctactaacatctcggc
ttgccaattcacctatgtatgtttgctttgtatattagtgcaggtattaa
tggccgcctgtaagtgagtttgttctcccttgttgaactaataaaattgg
catgaattcaccccaaaaagattgatgctgtttctcactagttttcagcc
tcagacgactatagatgtccaaacagtgcggaccgtccatttgaaacttg
acccgtcacgatttagtccggtccaagcatggccaagcagggttggtaa
cggcacgacctgtttagcgtgccgggtttgggcagctacagaggcccgcg
tgttttggtccgatccgacacgagcaatgggccgacacagcggcggccca
tttttcatatggcatatggtgccagcggccacacgccccccaaccaggc
cacacacccgaaccctatctctaatcccctcacccctcgggccctccgt
ccccatctctagcgattcggcgccgtcgttctcgcccgttgcatcccgtc
ggctcttgacctcgacggcggacgactctccatcgctgtcgtatgtggtg
ctccgacctgcttggacttggagttcctccgtcctccctcgtcactccct
ccgtctgcgactggggactccctaaccctaacccctccggtctccggatt
cggtggttctagctcctcagctgtgcaaggttcgtttatctcgtctaatc
ccctccagatttggtgtctagctgatgtctggtgctcgtctgtggtgtct
ggttgccgttgccggtggtcgtcacctgttgctcct
```

(>MAGI4_8905 MAGI4.contigs_w_singleton.fas 1736 bp)

A suitable nucleic acid molecule of the present invention is a gene that is up-regulated by nitrogen and contained in a full-length cDNA clone having the nucleotide sequence of SEQ ID NO:13, as follows:

CGACTGGAGCACGAGGACACTGACATGGACTGAAGGAGTAGAAATCTTGG

ATCTGGTGGTGGGTTCATCCTTGGCCCACTTCTTCTTGAGCTTGGGTGCA

TACCGCAGGTGGCAAGTGCAACAGCAACATTCGTGATGATGTTCTCCTCC

TCCCTCTCTGTGGTGGAGTTTTACTTCCTGCACAGATTCCCCCTGCCTTT

TGCTGGCTACCTCATCTTCATTTCCATATTGGCTGGATTCTGGGGCCAGT

GTTTGGTTAGGAAGATCGTGCATGTGCTCAAGAGAGCATCGCTTATTGTC

TTCATCCTCTCCTCTGTTATCTTCGTCAGTGCTCTTACGATGGGTGTCGT

TGGAACCCAGAAGAGCATTTCGATGATCAACAATCACGAATATATGGGGT

TCCTCAACTTCTGCGAGTAACTCAAACACCATCAGACTGTCGATCCGTCC

GGGAGAATCCAGGCCAATGCCTAATTGACCTCATCTCCCTCAAAATCTAG

AAGAATAAAGTCGCCGAGTATGTGCACAAGTTAGCTCCTCGCCAACATGT

GCGCATTTAGACCGACAGAGTCGCTGTAGTGAATTCAGCTCGTGTTAGCT

CCTGGCTAACGAGCTGACCATACGGCTTTAGTTTTGTGAAGTGGGCGCGA

TTTCGTCATGTCATGCATGTGTTAGCTCCTGGCTAACCTGCAAATGCGTG

TGTTGGTGCAGGTTTTTGTCACGTCTGCGTCAGCTCCTGGCTGACCAGCA

GTTGTTTGTCGTTCATTCTCTGCGTCAGCTCCTGGCTGACC (Underlined = GeneRacer Oligo sequence; Bold/Underlined = start codon; coding -continued sequence in bold) (Sequence of 5' RACE product CW31A10-Full_Length cloned into pCR4-TOPO) (derived from MEST31-A10, GB_ACC# BG842452)

The predicted protein or polypeptide encoded by the full-length cDNA clone of SEQ ID NO:13 has an amino acid sequence of SEQ ID NO:14, as follows:

```
MMFSSSLSVVEFYFLHRFPLPFAGYLIFISILAGFWGQCLVRKIVHVLKR
ASLIVFILSSVIFVSALTMGVVGTQKSISMINNHEYMGFLNFCE
```

A putative promoter (upstream of the transcription site of the gene) for the gene of the full-length cDNA clone of SEQ ID NO:13 has a nucleotide sequence of SEQ ID NO:15, as follows:

```
cttgggcggtagagctttttattagcttttcaaaaagttcaaggtcatca
aggtcagagtttaaatctaaaagctatgcctaaaatataaaatgggtcat
actgagcacccatacatatgatgatcttgtccagtaccacatctgataca
cacagagcattacggtgacccatgttccatatcttaaggtaacgaaggtt
tgtcctaagttaaagttttgaaactttgacaacaatatctacaaaaataa
ttatttttacttaaagaaattatatattgtgctagatgttttaataata
aatataatagttttatttttatttagtcaatgtttatgaatattttgtta
ttaatgataaaagtttcaaaattttgacttagtataaactttcgtgatct
taagatagggaagagagggagtgagtaggtatcaattgcacccaggtaat
gatcattttcaacggtcaaattactaaaaatagccgttaccaaaaactca
acagtgtacatgatgtggagcgatccgggggagacacccacttacgttc
aatgaaaatgctagtccacgaaggagacggaagcccaccctggcctctct
ttgaggcgaagccacgttccggccaatcgtctcacagcctctatgcaggc
tggaatgtcacccatgctgcacctcacctcaaccatcgtaaatcttaagg
accattcttcttaattaactcatttgcaagggtttgtagcgccgctttac
cttagtacatgtgttacagtaaacaaacaattgccagtgctttatatgat
ttcgatccatcatattttaggtccaaaacagcatcttcactcaaagagac
agattaaagctgtttggactgctttagctataataaaaatactgtagaaa
aaacagaagtcggtggaagccgcagcgaacatgttctgattttcacggaa
atacggcttgaaacgcactcggcttgcacaaacagaatgggaattgactg
atatttacaatgttccatgcaacaaatatttgcagttttgcagcctagcc
tggtgctagcgcaagaatgaacaacaaataactgctggtcagccaggagc
tgacgcagagaatgaacgacaaacaactgctggtcagccaggagctgacg
cagacgtgacaaaaacctgcaccaacacacgcatttgcaggttagccagg
agctaacacatgcatgacatgacgaaatcgcgcccacttcacaaaactaa
agccgtatggtcagctcgttagccaggagctaacacgagctgaattcact
acagcgactctgtcggtctaaatgcgcacatgttggcgaggagctaactt
gtgcacatactcggcgactttattcttctagattttgagggagatgaggt
caattaggcattggcctggattctcccggacggatcgacagtctgatggt
gtttgagttactcgcagaagttgaggaaccccatatattcgtgattgttg
```

-continued atcatcgaaatgctcttctgggttccaacgacacctgaaactcaccgaaa caagaggccattaggagagaagttaaaaatcaaactagattgatttagac gaaacaagtaaaagagctaatataatgctacatccgttctcgaatatttg tcgtccgttagttcatttttaaaatgaactaaaacgtgacaaataaaaa agaacggagaatggagtgagtattccttaagattatttttctcaaggatg catgctataattgcaaaatcaatttaagcaacaccggtacgtttagttca atttaagcaacaccggtacgtttagttcaattcaacttggagcggtatca ggttagcaatttgccaagtttaaagctaagtagcaagtcaatgagttatc aataggttcatacccatcgtaagagcactgacgaagataacagaggagag gatgaagacaataagcgatgctctcttgagcacatgcacgatcttcctaa ccaaacactggccccagaatccagccaatatggaaatgaagatgaggtag ccagctgcagatagagaaacagtgcaagttattaactcgttaccatataa caatcacacttatgaaaacgtctacattttgaggaattggaatctaacta atagagtaggttatttctttagaacgtgacatttcataa (>MAGI4_154269 MAGI4.contigs_w_singleton.fas 2189 bp)

A suitable nucleic acid molecule of the present invention is a gene that is up-regulated by nitrogen and contained in a full-length cDNA clone having the nucleotide sequence of SEQ ID NO:16, as follows:

CGACTGGAGCACGAGGACACTGACATGGACTGAAGGAGTAGAAAAAAGTG

CTCCCGGAAGACTCCAAGCTGCAGCTACCGGCCTTCCTCTCCCCCATTCC

AATTCCGAGAACAGGGGCGGCGGAGTCAACCAGGTACGATGTGCTCGGTA

GCGAGGCTGGCGTTTGTGCTTGCACTGGCCATAGCCGCCTCGTCAATTGA

GGTTGCGGAGAGCAGAGATTTTAATATCTTTGCTCAGGGCAGCTTGCCTG

ATGCAACCAAGGGATCGTCTGGTCTAGCTGCAACCAGTGGAAAGTTGTGT

CAGTTATGCGAGCAGTACTCATCCGAGGCGCTCCTCTATCTCACACAAAA

CGAGACCCAGACTGAGATTCTTAGCATTCTACACCATGAATGTGCCAGCC

TTGCCCCTCTCAAACAGCAGTGCATCACGCTGGTTGACTACTACGTACCC

CTTTTCTTCTTGGAGGTCTCCATGGTTACCCCTGAGAAGTTCTGCGAGTC

GATGCATCTCTGCAAGAAGGGGATGAAGATTAGCCTACCCACCCGGGAGG

GTACTTGTGGTTTGTGCCACCATGTTGTTGTTGAAATTCTTATCATGCTT

AAAGACCCCAACATGCAGCTGGAAGTAATCGACCTACTCACCAAAACATG

CAGCAAGGCGCAGAACTATGAACAGTAGTGCAAGCGGCTGGTCCTCAAGT

ATATTCCACTTATTCTGGTGAAGGGCCAGAAATTCCTTGAGACAACGGAT

GTCTGCTCTGTGATACATGCATGCAAAGCAGGCACACAAGCATCAATGGA

AGCCATGCCTCTGTCTGCCATGTTGTGAAGGTGATGCGA (Underlined = GeneRacer Oligo sequence; Bold/Underlined = start codon; coding sequence in bold) (Sequence of 5' RACE product CW42B12-Full_Length cloned into pCR4-TOPO) (derived from MEST42-B12, GB_ACC# BG873755)

The predicted protein or polypeptide encoded by the full-length cDNA clone of SEQ ID NO:16 has an amino acid sequence of SEQ ID NO:17, as follows:

MCSVARLAFVLALAIAASSIEVAESRDFNIFAQGSLPDATKGSSGLAATS

GKLCQLCEQYSSEALLYLTQNETQTEILSILHHECASLAPLKQQCITLVD

YYVPLFFLEVSMVTPEKFCESMHLCKKGMKISLPTREGTCGLCHHVVVEI

LIMLKDPNMQLEVIDLLTKTCSKAQNYEQ

A putative promoter (upstream of the transcription site of the gene) for the gene of the full-length cDNA clone of SEQ ID NO:16 has a nucleotide sequence of SEQ ID NO:18, as follows:

gcactcatagcacatctgaggttccctttcttgaacttagctcacctact gttcatagttctgcgccttgctgcatgttttggtgagtaggtcgattact tccagctgcaagcttgcagcaaacaaagaaaggcattacagtatgtacag agtacagagcagtacaacacagaagaatgttggtgacagatagtgaaaat atggttattacctgcatgttggggtctttaagcatgataagaatttcaac aacaacatggtggcacaaacccacaagtaccctcccgggtgggtaggctaa tcttcatccccttcttgcagagatgcatcgactcgcagaacttctcaggg gtaaccatggagacctccaagaagaaaaggggtacgtagtagtcaaccag cgtgatgcactgcagcagggtgaatcatcaacacaacatttaacacagct gaaaacgtggtaccaatggaaggatcacaagttacctatacctgctgttt gagaggggcaaggctggcacattcatggtgtagaatgctaagaatctcag tctgggtctcgttttgtgtgagatagaggagcgcctcggatgagtactgc tcgcataactgacacaactttccactggttgcagctagaccagacgatcc cttggttgcatcaggcaagctgccctgagctgaattgaagacagaagaaa ggattggccagaaatgcaaaacttcagaaaaacttgagttcctgtgagga atagcagctaagctgaagctacgccctctacattgagtagaactgatggc ttagacgtaattgctttctttaacatgtcaccggactaaatgaagatacg aacttgtcaaacaaagaaggaatttagataaactaattgaaactatcacg agatctccatcgaaaagaaactatcactagacctgataattcactgctat ggatcaacattcaacaaagaataaagagagtaaggagcaaaaatcagtag attgaaagcttaccaaagatattaaaatctctgctctccgcaacctcaat tgacgaggcggctatggccagtgcaagcacaaacgccagcctcgctaccg agcacatcgtacctgcttaccactaccagttggtcagttgacaggaacaa aactactgcttgaagaaaactatcgcagtgaaatcagctgtggctgatgg acgcagaaaagctggcttgctcaaagcttctccataaagccaaaaggtaa ccaaaaaaaaaagagaaaggaaatgtatcctagggccctctctctacgtc atgtaacggatcagtagaagtttcagattcattcagcccgacgtaactga agaattcagttcgcttcaagatgtagccatcagattcacgtatttggagt caagccaagatagtaccaattggtccgcatccacattccaggcaacagat tcacgagattcagctcgctccacgccagcagagctgctactattctggca ccactccaaatacgcctttgcagcagattagcaaagcattttacgctcgc -continued ttttgcgctttattttgcccctcgtttcctttccaggtagcttccggttc cgaagaatcggaggtccttggattcagggacaaggggtcgaactgggcag caaatcaagaaccgaggggagacggtagtacagagagcccaggagaagct aacatatgaatggggaattaaagacgcatctcacctggttgactccgccg cccctgttctcggaattggaatgggagagaggaaggccggtatctgcatc ttggactcttccgggagcactttgttttcttaaagcttcgtgttacatta agaagatgcatgagcatgtagaacagtgtgtgtggccgtgtgtgtgagaa cctgagatattttgcttctttggtggccaagatgtgttagaaaggcata atcttttctta
(>MAGI4_114997 MAGI4.contigs_w_singleton.fas 1961 bp)

A suitable nucleic acid molecule of the present invention is a gene that is up-regulated by nitrogen and contained in a full-length cDNA clone having the nucleotide sequence of SEQ ID NO:19, as follows:

CGACTGGAGCACGAGGACACTGACATGGACTGAAGGAGTAGAAATATAGC

CAGAACTCTTGCATCCTGGTGATGGTAAACTGCCGTGCCAGTATAAACGC

GAAGGCAGGTCACACATACTCACAAGTCCGTCCCATCTCAGGTCATCCAT

CCATCCATCCCTGCAGCAATGGCGTCTGCAGTGACCAGCAGCGACAAGGA

GCAGGCCGTCCCTACCATCGACGCTGACGAAGCGCACGCGCTGCTGAGCT

CCGGCCATGGCTACGTGGATGTCAGGATGCGGGGGGACTTCCACAAGGCG

CATGCGCCCGGTGCTCGGAACGTTCCCTACTACCTGTCCGTCACGCCGCA

AGGGAAGGAGAAGAACCCACACTTTGTAGAGGAAGTGGCTGCCTTCTGTG

GGAAGGATGATGTCTTCATTGTGGGTTGCAACACGGGGAACAGATCCAGG

TTCGCGACGGCAGACCTTCTGAACGCGGGGTTCAAGAACGTGAGGAACCT

GCAAGGTGGTTACCGCTCCTTTCAGCAGCGAGCTCAACAGCAGTAGACAT

CACGTCCTGAAGGTATGCCAGGGATGCTGCAGTTGAACG
(Underlined = GeneRacer Oligo sequence; Bold/Underlined = start codon; coding sequence in bold)
(Sequence of 5' RACE product CW43D12-Full_Length cloned into pCR4-TOPO) (derived from MEST43-D12, GB_ACC# BG873856)

The predicted protein or polypeptide encoded by the full-length cDNA clone of SEQ ID NO:19 has an amino acid sequence of SEQ ID NO:20, as follows:

MASAVTSSDKEQAVPTIDADEAHALLSSGHGYVDVRMRGDFHKAHAPGAR

NVPYYLSVTPQGKEKNPHFVEEVAAFCGKDDVFIVGCNTGNRSRFATADL

LNAGFKNVRNLQGGYRSFQQRAQQQ

A putative promoter (upstream of the transcription site of the gene) for the gene of the full-length cDNA clone of SEQ ID NO:19 has a nucleotide sequence of SEQ ID NO:21, as follows:

cgcactaagaaggcagggaattgtgtggcaaatataggtacatgctacac gtgtgatatttcccgatttgtcaatctgggacatgaagttaacatcgcaa -continued attataatgttacaggaaccaggtatggtgctagcttgcgtaagcaaatc aagaagatggaggtatctcagcattccaagtacttttgcgagttctgtgg gaaggtacatttctgttagttaccctgtttctgcatccaagttttctaat ctttgatctattgaactgcgagctgtctttatgttgtactcgttatcatc accactgctgttatgaaatgtaggctgcagtcagattgattttgagcaca tgaaatcaattagttttcgatatatctgtttgtcacaagcacatgaaatc aattagtcttcgatatatctgtttgtcacatttgaatgatttataagatg tctgggcatgtccatcaatgtgtttctaagatacatttgaagacagacag catttgttccgaatccaacctttgctgtgctgtgtttccagtttgctgtg aagaggaaagcagttggaatttgggggtgcaaggactgtgggaaggtgaa ggctggtggtgcttacaccatgaagtaagtaattcttcgcctgtccgaaa accacaatttgttagccacggctaaattctgttaatgtgtttgcagcact gctagtgcggtcaccgtcaggagcacgatccgccgcctgagggagcagac tgaagcatgatatagctctttatattattggggtttcctgtagttgctct tgtcaggcatgttgtgggggccttatctagtggaaatgtggaatcactgt actggctgttttgccgagacaatgctccttatatttggtttatgctctag gatctcaaagttgtgttaagatttgcccttggttaccgttctgaatctga caagtgatatttcatcctatgccatcttgacgtcgaatttggttgtggtt ttctatgcgcttggctgtgtcaatggtttgctattctgttcttgaaattc tacagatactgctgcgtctctgctggttgagtctggtttagatagcaacc agtccttattattggtctttcaagttcaagtcaactaaaatgcgacaaat aaaaaaaagaatggagggagtatataactgttcaagtcaaccaatcctta ttacgcctgcacttgtgtccaaaaagaaatgccccggagctattattggt ctgttgccagataagcagtgacgacgcagcatcgaaggtcagagacgact tttttgcgagaacgagcatcaagctgacggaatggagcattattccgata aaaaaaaggtatagccagaactcttgcatcctggtgatggtaaactgccg tgccagtataaacgcgaaggcaggtcacacatactcacaagtccgtccca tctcaggtcatccatccatccatccctgcagcaatggcgtctgcagtgac cagcaggtaaacatagcttctgagtgcatctgatgttgcttacagtaaca ttacatgcatagagcagaagatcggatgcatctggattaaccagagtcag tcttgtcttggtgtgcactgcagcgacaaggagcaggccgtccctaccat cgacgctgacgaagcgcacgcgctgctgagctccggccatggctacgtgg atgtcaggtgcgtagagctcagccagtcagggacgcgcctatgcgtgtgc tggagcttccagacgaactgacgctgacggggacgaggtggttctccttc gtgcaggatgcgggggggacttccacaaggcgcatgcgcccggtgctcgga acgttccctactacctgtccgtcacgccgcaaggtcagtttcttgctcgc tggcgttggcgctggcactggcattggggttattgatttgagctgcctct gtccccgtgtagggaaggagaagaacccacactttgtagaggaagtggct gccttctgtgggaaggatgatgtcttcattgtggtagctattcactcata taaataaataaataaatgtactagtactctataaatagatagatacgcct gtaatcaaggagttgtcgtgtagggttgcaacacggggaacagatccagg -continued ttcgcgacggcagaccttctgaacgcggtaaacacagcccatccgagctt tagcatcaatccagttagctgtatgtgtgtgtgtgtgtgtgtgtgtttaa ctgagggtcacactagtctgctcgcat
(>MAGI4_143540 MAGI4.contigs_w_singleton.fas 2277
bp)

A suitable nucleic acid molecule of the present invention is a gene that is up-regulated by nitrogen and contained in a full-length cDNA clone having the nucleotide sequence of SEQ ID NO:22, as follows

AAGATAGCTGCAAAACAAGCGAGTTACTTACAACCAAACAGAAGGGTAGA

AACCACCTGAAGCCATGTGCATTGCTGCATGGATTTGGCAGGCTCACCCT

GTGCACCAACTCCTCCTGCTTCTCAACAGAGATGAGTTCCACAGCAGGCC

TACAAAAGCAGTAGGATGGTGGGGTGAAGGCTCAAAGAAGATCCTTGGTG

GCAGGGATGTGCTTGGTGGAGGAACATGGATGGGGTGCACCAAGGATGGA

AGGCTTGCCTTCCTGACCAATGTGCTTGAACCAGATGCCATGCCCGGTGC

ACGGACTAGGGGAGATCTGCCTCTCAAATTCCTGCAGAGCAACAAGAGCC

CACTCGAAGTTGCAACTGAAGTGGCAGAAGAAGCTGATGAATACAATGGC

TTCAACCTCATACTAGCTGATCTAACAACAAATATCATGGTTTATGTGTC

AAACCGGCCTAAGGGTCAGCCTGCAACAATTCAACTCGTGTCACCAGGAC

TCCATGTGCTGTCCAATGCAAGGCTAGATAGCCCTTGGCAGAAGGCAATT

CTCCTCGGTAAAAACTTCAGGGAGCTTCTTAGGGAGCATGGTGCTGATGA

GGTTGAAGTGAAGGATATAGTTGAGAGGCTAATGACTGACACCACAAAGG

CTGACAAAGATAGACTGCCAAACACTGGTTGTGATCCCAACTGGGAGCAT

GGTCTGAGCTCCATCTTCATTGAGGTGCAAACTGACCAAGGGCCCTATGG

GACACGGAGCACAGCCGTTTTATCAGTGAACTATGATGGCGAAGCTAGCT

TGTACGAGAAGTATCTTGAGAGTGGTATATGGAAGGATCACACAGTGAGT

TACCAGATAGAGTAGTAGGCATTGCACAGGAAAAGTTGGCGACCTCA
(Underlined = start and stop codons; coding
sequence in bold) (Sequence of 5' RACE product
AM45C08-1T3 Full_Length cloned into pCR4-TOPO)

The predicted protein or polypeptide encoded by the full-length cDNA clone of SEQ ID NO:22 has an amino acid sequence of SEQ ID NO:23, as follows:

MCIAAWIWQAHPVHQLLLLLNRDEFHSRPTKAVGWWGEGSKKILGGRDVL

GGGTWMGCTKDGRLAFLTNVLEPDAMPGARTRGDLPLKFLQSNKSPLEVA

TEVAEEADEYNGFNLILADLTTNIMVYVSNRPKGQPATIQLVSPGLHVLS

NARLDSPWQKAILLGKNFRELLREHGADEVEVKDIVERLMTDTTKADKDR

LPNTGCDPNWEHGLSSIFIEVQTDQGPYGTRSTAVLSVNYDGEASLYEKY

LESGIWKDHTVSYQIE (The above sequences are presented after trimming GeneRacer Oligo sequence. Cloned in pCR4-TOPO wctor at the "TOPO Cloning site".)

A suitable nucleic acid molecule of the present invention is a gene that is up-regulated by nitrogen and contained in a full-length cDNA clone having the nucleotide sequence of SEQ ID NO:24, as follows:

CGACTGGAGCACGAGGACACTGACATGGACTGAAGGAGTAGAAAATCAGC

CGCAGTCGCGTCGCGTCGCGTCGCGTCCAGTCCAATCCTCGGAGCCTCAC

ACGGGCGGACGAGCGGGAGCTTCTCCCAATCTCCCCTGCCCTGCCCTGCC

CTGCCGCCGCGCTTAGCTTCGCATCTTCCCCTCCTCCTCCTCCTCCTTCC

TCGGCCAAGCGAGGAGCGAGGCGCGGGCGCGAGCGCGTCGTTGAGATGGA

TTCGGAGGCGGTGCAGCACGGCCTTCTCCCTCTGTCTGCCTGTCCTCCTA

CCGCCAACAGCTGCGCGCATTACAGCCGTGGGTGCAGCGTCGTGGCGCCC

TGCTGCGGCCAGGCCTTCGGCTGCCGCCATTGCCACAACGACGCCAAGAA

CTCGCTGGAGGTCGACCCGCGCGACCGGCACGAGATCCCCCGCCACGAAA

TAAAGAAGGTGATCTGTTCTCTCTGCTCCAAGGAACAGGACGTGCAACAG

AACTGCTCCAGCTGTGGGGCCTGCATGGGCAAGTACTTCTGTAAAGTATG

CAAGTTCTTCGATGATGATGCCTCAAAGGGCCAGTACCACTGTGACGGAT

GTGGAATATGTAGAACCGGCGGCGTGGAGAACTTTTTCCACTGTGATAAA

TGTGGGTGTTGCTACAGCAATGTCTTGAAGGATTCCCACCACTGCGTCGA

AAGAGCAATGCATCACAACTGCCCCGTCTGCTTTGAGTATCTGTTCGACT

CCACGAAGGACATCAGCGTGCTGCAATGTGGGCATACCATCCATTTGGAG

TGCATGAACGAGATGAGAGCACACCATCACTTCTCATGCCCAGTGTGCTC

GAGGTCCGCCTGCGACATGTCGGCCACATGGCGGAAGCTCGACGAGGAGG

TCGCGGCCACGCCGATGCCTGACATCTACCAGAAGCACATGGTGTGGATC

CTGTGCAACGACTGCAGCGCGACCTCGAGCGTGCGGTTCCACGTGCTGGG

GCACAAGTGCCCCGCGTGCAGCTCGTACAACACCCGGGAGACGAGGGCTG

CGTGCCCCAGGATCTGAGGCGAACCAGAGGCCATGTCACAAAATGCCAGG

GAGATGCCGTCCAACGACCATCTGTCTGCAGGACGTTGCTGCGCTTAAGG

TTAAAGGCTAGCGCGAGACCAGGCCTGGTAGTCCAGTCTTGAGTTTGGTG

CTGGAGCATTTGTAATGTTCCGGTAAAATGTAATGCGTCCATGAGTGCTG

TCCAGGCAGTAAGCACACCTGTGGATCGGGGCCGGCGCAAGGTCCCTAGG

CAAGCTGCAGGATTAGTGGGGCTATTCATGTTTAGGGCGCGAATGCAA

CGA
(Underlined = GeneRacer Oligo sequence; Bold/
Underlined = start codon; coding sequence in bold)
(Sequence of 5' RACE product CW55C10-Full_Length
cloned into pCR4-TOPO) (derived from MEST55-C10,
GB_ACC# BM072886)

The predicted protein or polypeptide encoded by the full-length cDNA clone of SEQ ID NO:24 has an amino acid sequence of SEQ ID NO:25, as follows:

MDSEAVQHGLLPLSACPPTANSCAHYSRGCSVVAPCCGQAFGCRHCHNDA

KNSLEVDPRDRHEIPRHEIKKVICSLCSKEQDVQQNCSSCGACMGKYFCK

VCKFFDDDASKGQYHCDGCGICRTGGVENFFHCDKCGCCYSNVLKDSHHC

VERAMHHNCPVCFEYLFDSTKDISVLQCGHTIHLECMNEMRAHHHFSCPV

CSRSACDMSATWRKLDEEVAATPMPDIYQKHMVWILCNDCSATSSVRFHV

LGHKCPACSSYNTRETRAACPRI

A putative promoter (upstream of the transcription site of the gene) for the gene of the full-length cDNA clone of SEQ ID NO:24 has a nucleotide sequence of SEQ ID NO:26, as follows:

```
ccttacaggttatcacttaccgcctccgttttcgaatatttatcgttcgc
tagttaatcttaatttaaacttaaatgaggcaaataaacgtttaaactat
tctcttgatcgtgtgtctgattgtcttgttgtttaaaatgcctcctagat
cgatcgtcgtagtgcaggttgttttagacaaagttgaactgcgatcagac
cgagaccggacaaccattgagcagttattttcctattcatcgtggactaa
ctggaagatattttctgagctccaaaaaatatccaaaggaagggagaacg
tgaaggacgaggtcggaccggacacgcctcccctcgctaatcattgaggc
ggaggcggcggaggcgattttgggaacactcgcaggtagattttgcgtga
acttggacgagggtcattttcgctttggatgaatccacgaggtggtgtca
ctgcacgcgcacggggccctcaaaccgtttgaaaaccaaaccgaaggcaa
caaaacgagactctcatctcatctgactctacggccagctcaagtgatct
gctgctggtggccgacctggcggcgtgatctcgctcccgtgcccgtctcc
tccatccgacgcgtacatggcccgccatcctcatccatccgccctccaga
ggaccagtccagaccaataataaaagggaaggtcgacgacgggctcgctc
caatccggcgaaccgcgtccccgtcagcctgtcatcccgtgggcgcgcgg
ctgtcgacctgcgcatcagcttctatgattagccaggagcaataatttat
tactcctatttgccaggcgacgttcgtccaattcgacccggcaggcagca
ggcagcagctgtgctcctgtgggtgggtgggtcatgggtgaccacatgca
tcgatggagccagggccgccgtgtgcgcagccaactctacctatccccgc
ccccgggatgggcgatggcaactatcctatcgcaacaatatcctggggtg
ggggctataaaacggagcggcccgcgtggggcgcgcctccatcagccgca
gtcgcgtcgcgtcgcgtcgcgtccagtccaatcctcggagcctcacacgg
gcggacgagcgggagcttctcccaatctcccctgccctgccctgccctgc
cgccgcgcttagcttcgcatcttcccctcctcctcctccttcctcgg
ccaagcgaggagcgaggcgcgggcgcgagcgcgtcgttgagatggattcg
gaggcggtgcagcacgggtaagcaagcaaagcaatccatggatcgatcca
ggacacagggaggagctaggaagaggaacaatctcatgatctcattcatc
tgacacagccttctccctctgtctgcctgtcctcctaccgccaacagctg
cgcgcattacagccgtgggtgcagcgtcgtggcgccctgctgcggccagg
ccttcggctgccgccattgccacaacgacgccaaggttcggtggtttccc
tccttccgttttcgcttcggctccggttcagcagatgttctgaaacaacc
ctgtcccgtgccccggcagaactcgctggaggtcgacccgcgcgaccggc
acgagatcccccgccacgaaataaagaaggtcagcgttccctccctctgc
tcaaagagcaatctcctgcctgtttcaaccattgcctatctcgtgttcgt
ctttgttattaccgtgagcaaagaaaggaagaaacaaacaagagcgccgc
cttctctcttctccttctccatgtaatggagcatttgttccgccgcgtag
tcgagtgcaagcagcggttttcctcttttggaaacccacccccacgcacg
gttccgttccaatctcgcccttccaattgaccaacacaaacctttcctaa
```

-continued

```
gatttcttgtcctccttacccttctacagacaagtacgaaacgcaatcgc
acaaggttatactactactagcttttagtgttctagcgaccttagatttt
tttttttggttaggcatccctgatttttctcacacttaaaagcttcttca
gataaggccatatcagctcagctcagtgctctgggagccgttctgcactt
cacttgcgtgtcactaaaaacttgactgctttccgcgatgtgctccgcac
caagtggccggcactgcgtggtccacaggatttttcaagagaaagccggg
gtcacgggtgccacttgaagccaaggacaggcgtctgggattggagaata
tatgagaaagggataccgtcagaggcacatctcaccgtcaaactgaacag
ggtctaactgcttccagctgatttgattgagtttgagtgctgcatagttg
aggacctggatatagtgacgtgtcctgacaggtgtctttggacctattag
cagtgaatctgacgtcgatcggctaaagcaatcatgttcgattcttatcc
ttttttttttgagagtatatgcctgattcgataaacgttcctatcctgtt
tcctgatgatgcatatatgttgtttcgattcatatagaatcataccatcc
atctattttgtttaaaaaaaaaatttctgggtggccatgggcacagcatg
cctgttcttaagataacgattccagtaactgttcccttctgtcactgaac
tcatatgaatcgagacttaactggagctgttgcgcaggtgatctgttctc
tctgctccaaggaacaggacgtaagttgtctaccaaaacgtactcctaca
acagtttttcaggagcacgcatcttttggctgtactactactgctaactg
catggaaactgctcattcccatcggcaggtgcaacagaactgctccagct
gtggggcctgcatgggcaagtacttctgtaaagtatgcaagttcttcgat
gatgatgtaagcgtactcgaatcccagacgatgaacaaagaaactgaact
cgatgcgttgtttactgcgtttctttttttccccccttcttcttcacgtaca
tactgtactgctcttggtccaggtctcaaagggccagtaccactgtgacg
gatgtggaatatgtaggtaagcaccaccacgctgatggctacgtctaaag
acttgacgcgcagaagtgtaaaacttctgtcagccgttcaaaactgataa
attcgggttcctcgtcttcttgttgtttatgcagaaccggcggcgtggag
aactttttccactgtgataaatgtggtgagtttctgcgcggacttctttc
tgctaagattctgtaaccatgctatgcagcaaagatttcactcgcgccct
tattggtgtccttgttgccgtccgacagggtgttgctacagcaatgtctt
gaaggattcccaccactgcgtcgaaagagcaatgcatcacaactgccccg
tctgctttgaggtgagagacctccgtttcaacggaacattcactctgaat
gttccaatctcttgatattgagaaggtttccctctgtttttttttcacagt
atctgttcgactccacgaaggacatcagcgtgctgcaatgtgggcatacc
atccatttggagtgcatgaacgagatgagagcacaccatcagtaagcata
tataccgttctcttcggagctgagaaacggtgccacctcacaacatcctc
ttttagtcgcagtgaccttacagtctcagccctgtttggtctttggcagc
ttctcatgcccagtgtgctcgaggtccgcctgcgacatgtcggccacatg
gcggaagctcgacgaggaggtcgcggccacgccgatgcctgacatctacc
agaagcacatggtaagaagccgaccgcccactcgttcgtcgtcccgttac
atcttttccacagccatggctcgctgtttgacgagctctgaacctgtccg
```

-continued gggtgccgattgctggaactgaacggcaaatgaacgctgtggtgtgagtg
caggtgtggatcctgtgcaacgactgcagcgcgacctcgagcgtgcggtt
ccacgtgctggggcacaagtgccccgcgtgcagctcgtacaacacccggg
agacgagggctgcgtgccccaggatctgaggcgaaccagaggccatgtca
caaaatgccagggagatgccgtccaacgatcatctgtctgcaggacgttg
ctgcgcttaaggttaaaggctagcgcgagaccaggcctggtagtccagtc
ttgagtttggtgctggagcatttgtaatgttccggtaaaatgtaatgcgt
ccatgagtgctgtccaggcagtaagcacacctgtggatcggggccggcgc
aaggtccctaggcaagctgcaggattagtggggctattcatgtttagggc
gcgaatgcaacgaaattacccgtgggccgtgggctcggtatgtaacagaa
ccgattatttctattacaataataacatgcagttctattgggccgagcct
aatcaggcaccacgaatgtgaataattgcacatggcgcatatatggcggg
cagtagatacatataaaatggagaaaatccgtttattgccatcaaaactt
atactgatcactacaataccatctaaaatgatgtgctcccttcaaaacca
ttggtttatattttctatcctttcattgccattgccgttacataatggcg
catgtggcatatatgggcggcgtatgtaggttcaggatggtcacacgaca
tatgacgagactacagagacatggtcaagagaagttcagtggattgtgac
attctgatctaagacttcttaaaattggagttaataagatcgataatact
cgtaccaataatgcacatcttgcttttttagaagcctgttttgaaataacc
ccaggattaagcatgtttggcccaaagaaatttttgtgatggtggtcgac
cgagaagttttcttgactgcatgccagtgaggacaaaaaaacacatatga
aagaatcgtgttggtctgtgagaatagatcaggaagttttctcgactgcg
cgaccatggatggttggggtgtttcatcaaggatccgctttaaacacata
cctttttgccttggtgatggataaggacataccggacataaaggggataa
cccttggtgtgtgtttttttgcagacaatgtaatgctagttgatgaaagt
cgggcatgagtaaatggaaaactagagttgtggcaagaaactttataatc
aaaaggttttagacttagtagaactaaaatagaatatattggatgcgatt
tcagcactacatatgaggaatgagatcttagtttagaaggtctaggaagg
acacctttagatatttagtatcagcctatagagagaccgggatattaatg
aagatgctagccataaaatcaaagtagagtcagtgaagtggagtcaagca
tctggcattttatatgacaaagtgggaattgcaaaagctaaaaagaaagt
tttaggacaacgattagaccttctatattatatggaacataattttagcc
tacaaaaagatgatatgtttagcagataaatgttgcggtaatacatatgt
tacgttggatttgtgaacatacaaaaagggatcgagtttagaatgatgat
atacatgatagactaggggtagcaccagtcgatcgatatggtttgaatat
atccaacggagacctatagaggtgtcaatatgtcttaggacctgtttgaa
agcatccagtttttaagaaattggtttatagaaattaaagtggttccaaa
catacaagtttatgccccagtttatataaactggattatcaatttcttaa
aaaccaagaagctagtctttgctagctaaaaccaacttttgcttgtttaa
ttacataatgcccttgttggttgcatggaatttacatctattgtcgtcgc
ttttaagatagaggaagggtatgttagtaattgtgtatcaaaaaatagaa
aatttgtttcttagaactaagttccaaacaccctcacctaactttttat
aaactagtttctataaactggagatagaaattggtttttaataaaccggt
atgctttcaaacaataccttaggattctaagatgtgataccaatgagaaa
aggaagaggaagactgaagttggtatgggaggtgataataaaatgagtct
tgaaaaaatgagatatatctaaagatttagccttgaatagaaatgcatga
aaataactatccatatgtttgaaccttgactttgagttttgttgaatttt
taactctagcctacgccaatttgtttgggactaaaaggttatgttgttgt
tattgccgctataaatggtgttcaacactttcttcaagattatgatattt
tgttttctacaccaacaatattactgttggggtctccttctctgccgaag
gtcctcaggatgaagaaactgtctttggttcatcttggtaagatacgtca
aaaggaccgaatgccgaagctgtgacagacatgcagggaatatagcagag
cttcgataagagttaaagcttcggcttaagatgattatgaaggtcataca
agaaaccaagccaccaatgaaaagacctgtttatccttaaaatttgtatt
agaacaatgtatagatatcagggtcataaatgtacttttgcttgggcggc
gtcccgtgcctataaatagatgaactgtaccccccgtactgttgacacttt
cattgaaagtcattctcgcactctctccttcaagcaagacgaaggtacta
atgtaatataatgtttgtaatggttcattagaatgttatccaaactatgt
cattactttgatatagaaaataaagtgaattcataagataataccacatt
gtgatattatctccatgagaaatgaagatccgctcttcttcaccttcgcc
caaaaaccattatctttgagagaagataattgaaaggaaattgggttaac
catttcctataactaattttggtgggtgatgatcaacacaaacccatgga
ctaactagtttgtctagaattcatggattacaggtgcataaggttcaaca
caaaccaagaaagaaatccggttagggacacaattaaaaatggagcaaag
acttga
(>MAGI4_73717 MAGI4.contigs_w_singleton.fas 7106 bp)

A suitable nucleic acid molecule of the present invention is a gene that is up-regulated by nitrogen and contained in a full-length cDNA clone having the nucleotide sequence of SEQ ID NO:27, as follows:

CGACTGGAGCACGAGGACACTGACATGGACTGAAGGAGTAGAAAGCTGCT
ATTTTCTTCTTACATTGTCCACTGCGCTAGCTAGCTCGCATCTACCTGGA
AAGCTGAAAGCTAGCCAGAGCGCTAGCTAGCTTCGTTCCTCGTCGCCGCG
CGCCGGCCAGATGACTGCTCACCAGACTTGCTGCGATGATGCCGTTGCCG
CCGGCACTGCACCGGCTGCCAGGAGGAGGCGCCTCAAATTGACGAGGCCG
TCGGCCTCGCTCTTGATGGCGAGGAAGCTAAGGAAGAAGGCTGCCGGCAG
CAAACGCCCAAGGGCGGCAGCGTCGAGGAAGCGCGCGATGGCGATCAGGA
GGAAGATGGAAGCGCTGAGGCTGCTCGTGCCACTCTGCGGCCGAGACAAC
GGCTCGGTGACCGGTGGGGCGGTCGAACGACTGGACGAGCTCCTCATGCA
CGCCGCCGGGTACATCCTGCGCCTCCAGATGCAGGTCAGAGTGATGCAGC
TTATGGTCCATGCACTAAATGACCGGCCCGAGGATTAATCTTCTTCCCAA

-continued

GACCATGTGATCTTCCTTCTTTAATTTCTTCTTCATCTTCTTCGCGTGCC

TGTGTTGCACGAGGCAGCTGTGCGTCGGTGTCTGGGTGCAAATCA
(Underlined = GeneRacer Oligo sequence; Bold/ Underlined = start codon; coding sequence in bold) (Sequence of 5' RACE product CW61A10-Full_Length cloned into pCR4-TOPO) (derived from MEST61-A10, GB_ACC# BM073122):

The predicted protein or polypeptide encoded by the full-length cDNA clone of SEQ ID NO:27 has an amino acid sequence of SEQ ID NO:28, as follows:

MTAHQTCCDDAVAAGTAPAARRRRLKLTRPSASLLMARKLRKKAAGSKRP

RAAASRKRAMAIRRKMEALRLLVPLCGRDNGSVTGGAVERLDELLMHAAG

YILRLQMQVRVMQLMVHALNDRPED

A putative promoter (upstream of the transcription site of the gene) for the gene of the full-length cDNA clone of SEQ ID NO:27 has a nucleotide sequence of SEQ ID NO:29, as follows:

taaatctgacctccaaaatgtctctaatgaaagtgtctgcgagaaacagt attgctcgaccgaggaagaaaggtatttataacacacccatcacaaatgg ttggcttaattaaccgcaagtgcagaatagatttgcactgttggttcact taataaaactgcaagtgaaaatatactttttctactatcggttttgttaa gtgaacctaccgattttgcactggtgattatttaagccaacctcatgtga taatatgaatgatttgcacgtggttttattaagcgaactaacaatgtaaa tgtgtttccaatggtggtttttaagtcgggaccgtcattttactttaact ggcgcgcaccgtgctgttttatacttgactgatgaaccttcgtggtgagt ggaagcggtgtggagcgagggctagctcatgcggccagccggcgacattt ctcttgttccgatcccccggccggccaaccactcaattaagtaggtgatc gattggcatgcatgcatggatgcatatcagcaaatgcatatcatatgcct cgctagctggctagtatatatagtggatgtggatcggatcatgtgacggc cgggcggtggctgcattgcattggccctgcatatatgcacggtgacacaa caacggggcccaaataaaggacacgtcgaaggtgcgcgccccagtggcgt ccgacagcgcgttttgacgaggaaaagagggtgcgggcacgcgcgcacgc atatgctcgcggcatgcagcctcagtggccgatgacgagtggcgtgtggt gtggccggcggccggccggccgggtgcctgcgtggtgcatgttgcttgcc atgcctgcgtgaaatgagccgtcagcgagcgagctgagggcgggcatgtg gctgcatgtggccactagtttggagaacatgcggcatatgccccggacct tcctgggcgctcaagcaaacaccgctctcgtgctcgctctcttgggaaat cgcagatgcatgctacccaacgtgacctggatctcttttacgtacgcaca ccctagcgtgctgctctcctgtgtccccgcctcctgctagctgttcacaa tatccacgcgatttaacaaacagatatgtgtgcatgctactgcttgtttt cctattcaatatagtaatctgctttatttagagtaccgtacctgtgccgt cagtgcccccaaccccaacgtaactacgcacgcacatggcatctaatcta tataagcatcagaccttgctcccttaatctcgcgctgctatttcttctt -continued acattgtccactgcgctagctagctcgcatctacctggaaagctgaaagc tagccagagcgctagctagcttcgttcctcgtcgccgcgcgccggccaga tgactgctcaccagacttgctgcgatgatgccgttgccgccggcactgca ccggctgccaggaggaggcgcctcaaattgacgaggccgtcggcctcgct cttgatggcgaggaagctaaggaagaaggctgccggcagcaaacgcccaa gggcggcagcgtcgaggaagcgcgcgatggcgatcaggaggaagatggaa gcgctgaggctgctcgtgccactctgcggccgagacaacggctcggtgac cggtggggcggtcgaacgactggacgagctcctcatgcacgccgccgggt acatcctgcgcctccagatgcaggtcagagtgatgcagcttatggtccat gcactaaatgaccggcccgaggattaatcttcttcccaagaccatgtgat cttccttctttaatttcttcttcatcttcttcgcgtgcctgtgttgcacg aggcagctgtgcgtcggtgtctgggtgcaaatcattggctgagtgtgtta ttggtgatattatttgttcgtatatacagaatatatactcatgcatgcat actgtatgagatgatagagtaaatctagacatatatagttcaaggaaacc tacagccaacagttgtatgcatgtgaggggggttccttgtctgtatgtac gcaattgtctattgtgtgacggttgaaattgaaatttcgtcaatcatcat ttcttcgtctagataacgtgtgtacaaacggcgagtgtttaaatgaacta gagctaataattagtggctaaaattagctggagacatccaaacaccctaa ctaataatttaactattagttattttagtaaattagtcaatacttagct agctatttgttagctagctaattctactagcatttttagctaactagct attagctctagtacattcaaacacccttttagggactaatttttagtctc tccattttatttcattttagtcactaaattaccaaatacgaaaattaaag ctctattttagtttccggtatttgacaatttag
(>MAGI4_145622 MAGI4.contigs_w_singleton.fas 2433 bp)

A suitable nucleic acid molecule of the present invention is a gene that is up-regulated by nitrogen and contained in a full-length cDNA clone having the nucleotide sequence of SEQ ID NO:30, as follows:

GGACACTGACATGGACTGAAGGAGTAGAAAATCCATCCATTCCCCTCGCC

AAGCCGCCACGGCCTGACTTTCCCTCCCGCACACCCGCGACCATACAGGC

AAGTCAGGCATACACCAACAACGCTCGTCGTGCACCTCGCGCCTCAGGTC

ACCCCACCAAATTCCTCTTGATACGCCGAATTTCTTTTGCTAATTCTGCT

ACCTCCTGTCGCTAAGCCACCATATTCAGTCTAACCCCTGCTCTGAGCTC

ACCTGATTGGCGGCTCCGTTCGGCCTCTGGGCCTGGGTGTACCGACTACC

GAGGGCTCTTTCGAAATGTCAATTGGGTCGAGTTTGGTGGGCTACGTGAA

GCATGGATGAATTTCCCGGCTGGAAGCGGGAGGCGGCAGCAGCATCCGGG

GCCGGAGCACCTGTCGCCGATGACGCCGCTCCCGCTGGCGCGGTAGGGGT

CGGTCTACTCGCTCACGTTCGACGAGTTCCAGAGCTCGCTCGGTGGGGCC

ACCAAGGACTTCGGATCCATGAACATGGACGAGCTCCTCCGCAACATCTG

GTCGGCGGAGGAGACACACAGCGTCACAGCTGCGGACCATGCCGCGCGGG

CGCCGTACGTCCAGTGCCAGGGCTCGCTCACCCTCCCCTGCACGCTCAGC

CAGAAGACCGTCGACGAGGTCTAGCGTGACCTCGTGTGCAACGGTGGAGG

-continued

ACCCTCCGACGAGGCTGTGGCGCCGCCCCACCGGCCCAACGGCAGCCGAC

GCTCGGGGAGATCATGCTGGAGGAGTTCCTCGTCCGCGCCGGCGTGGTGA

GGGAGGACATGATGGCGGCGGCGCCCGTACCACCAGCGCCGGGTTGCCCA

CCACCTCATCTGCAACCGCCAATGCTGTTTCCACATGGCAATGTGTTTGC

TCCCTTAGTGCCTCCGCTCCAATTCGGGAATGGGTTTGTGTCGGGGGCTC

TCAGTCAGCAGCAGGGAGGTGTTCTTGAGGCCCCGGCGGTATCGCCGCGG

CCGGTGACGGCAAGCGGGTTCGGGAAGATGGAAGGAGACGACTTGTCGCA

TCTGTCGCCATCACCGGTGTCGTACGTTTTTTTGTGCTGGTTTGAGGGGA

AGGAAGCCACCAGCTGTGGACAAGGTGGTTGAGAGGAGGCAACGCC (Underlined = GeneRacer Oligo sequence; Bold/ Underlined = start codon; coding sequence in bold) (Sequence of 5' RACE product CW76H12-Full_Length cloned into pCR4-TOPO) (derived from MEST76-H12, GB_ACC# BM073865)

A predicted protein or polypeptide encoded by the full-length cDNA clone of SEQ ID NO:30 has an amino acid sequence of SEQ ID NO:31, as follows:

MDEFPGWKREAAAASGAGAPVADDAAPAGAVGVGLLAHVRRVPELARWGH

QGLRIHEHGRAPPQHLVGGGDTQRHSCGPCRAGAVRPVPGLAHPPLHAQP

EDRRRGLA

Another predicted protein or polypeptide encoded by the full-length cDNA clone of SEQ ID NO:30 has an amino acid sequence of SEQ ID NO:32, as follows:

MLEEFLVRAGVVREDMMAAAPVPPAPGCPPPHLQPPMLFPHGNVFAPLVP

PLQFGNGFVSGALSQQQGGVLEAPAVSPRPVTASGFGKMEGDDLSHLSPS

PVSYVFLCWFEGKEATSCGQGG

A putative promoter (upstream of the transcription site of the gene) for the gene of the full-length cDNA clone of SEQ ID NO:30 has a nucleotide sequence of SEQ ID NO:33, as follows:

tagaatagccagcatcgacaaattacttacaaatagaaacattacctgtt tcctcccacgcgacctcgcggccaactcccggttcttgatcatccggcgt tgcctcctctcaaccaccttctccacagctggtggcttccttcccctcaa accagcacaaaaaaacgtacgacaccggtgatggcgacagatgcgacaag tcgtctccttccatcttcccgaacccgcttgccgtcaccggccgcggcga taccgccggggcctcaagaacacctccctgctgctgactgagagcccccg acacaaacccattcccgaattggagcggaggcactaagggagcaaacaca ttgccatgtggaaacagcattggcggttgcagatgaggtggtgggcaacc cggcgctggtggtacgggcgccgccgccatcatgtcctccctcaccacgc cggcgcggacgaggaactcctccagcatgatctccccgagcgtcggctgc cgttgggccggtggggcggcgccacagcctcgtcggagggtcctccaccg ttgcacacgaggtcacgctagacctcgtcgacggtcttctggctgagcgt gcaggggagggtgagcgagccctggcactggacgtacggcgcccgcgcgg catggtccgcagctgtgacgctgtgtgtctcctccgccgaccagatgttg -continued cggaggagctcgtccatgttcatggatccgaagtccttggtggccccacc gagcgagctctggaactcgtcgaacgtgagcgagtagaccgacccctacc gcgccagcgggagcggcgtcatcggcgacaggtgctccggccccggatgc tgctgccgcctcccgcttccagccgggaaattcatccatgcttcacgtag cccaccaaactcgacccaattgacatttcgaaagagccctcggtagtcgg tacacccaggcccagaggccgaacggagccgccaatcaggtgagctcaga gcaggggttagactgaatatggtggcttagcgacaggaggtagcagaatt agcaaaagaaattcggcgtatcaagaggaatttggtggggtgacctgagg cgcgaggtgcacgacgagcgttgttggtgtatgcctgacttgcctgtatg gtcgcgggtgtgcgggagggaaagtcaggccgtggcggcttggcgagggg aatggatggatatgtgtcgccaccaaggagtcgtgtgggggagtttaaaa cgtcgccaggctcgaggtcgcacatggtgttgggtttgggtgcgtgctgg gtcataaaagctgaaagggaattaggcttacacctatttcctaaatgatt ttggtggttgaattgtccaacacaaa (>MAGI4_7232 MAGI4.contigs_w_singleton.fas 1376 bp)

A suitable nucleic acid molecule of the present invention is a gene that is up-regulated by nitrogen and contained in a full-length cDNA clone having the nucleotide sequence of SEQ ID NO:34, as follows:

ATTCCCGTCTTACCTAGCGCTAGGGTTAGTACGCGTCCACGGCGACGACC

TCTGCGCGGAGTGTGCTCCGATTGGCTGGCCTCCTCGATCCTCCTTCCCG

CGAACGCACGCGCGCGCGAGGGAGAGGTTGAGACTTGAGAGATAGACGAA

AGACGAAACAAGGGAAGGAGACGCCGTGCTCGCCTATTGGCCGCCGCCTC

CGCTCCTTCGCGCCCAATGGCTTCTGCAGCATATCAATATCATGCAGCAT

AGCAGTACTCAGACCCTTACTACGCAGGCGTTGTTGCTCCCTATGGAAGT

CAAGATGTGTGTCCGAGGAGCCTGTCTATGTGAACGCCAAGCAGTACCGC

GGCATTCTAAGACGGCGGCAGTCACGTGCCAAGGCCGAGCTTGAGAGAAA

GCGCTGGTCAAGCAAGAAAGCCGTATCTTCACGAGTCCCCGTCATCAGCA

CGCGATGACGAGGAGGGCGAGAGGGAACGGTGGACGCTTCCTAAACACGA

AGAAGAGTGACCGTGTCCCTCCTGATGACTTGATACAGCTACGACGACAC

AACGAGGCTTGAAGAGGTAGCGGTCTGGCTGGCATCCTAGAGCAGCGGTT

TCTGTCCACAGGCACGTGCATCTGAGACCGGATCCGTAGCTCCACTCCAC

AGCATATGCGCAGCCCATCCATCTCGTGCACACTTG (Underlined = start and stop codons; coding sequence in bold) (Sequence of 5' RACE product AM77A01-5T3 Full_Length cloned into pCR4-TOPO)

The predicted protein or polypeptide encoded by the full-length cDNA clone of SEQ ID NO:34 has an amino acid sequence of SEQ ID NO:35, as follows:

MQHSSTQTLTTQALLLPMEVKMCVRGACLCERQAVPRHSKTAAVTCQGRA (The above sequences are presented after trimming GeneRacer Oligo sequence. Cloned in pCR4-TOPO vector at the "TOPO Cloning site".)

A suitable nucleic acid molecule of the present invention is a gene that is up-regulated by nitrogen and contained in a full-length cDNA clone having the nucleotide sequence of SEQ ID NO:36, as follows:

CGACTGGAGCACGAGGACACTGACATGGACTGAAGGAGTAGAAAAAAAAC

CCAAATCAAATTTCGCCTTCGTCGTCGTCTTATCGTCTCAGATTTGACTC

CATGTCGGCGGCGCTCGCGGTGACGGACGAGGTGGCCCTGCCGATCCGGG

CGGTGGGGGATCTAGCGGCCGCCGCCGAGGTCTCGCGGGAGGAGGTCGCC

GTCATCACCCAGTGCGCGGCGCTCGGTGGGAAGTTGCCTTTTGAAGATGC

ATCAGTTGGTGCGGTTCTTGCAGTCATTAAAAACGTGGAAAGCTTGAGGG

AGCAATTGGTTGCTGAAATCAGGCGGGTGCTGAAAGCTGGTGGAAGAGTA

TTGGTGCAGAGCCCTGCACCCTCATCCAGTCAGAAGCCGAACACTGATAT

TGAGCGCAAGTTACTGATGGGTGGATTTGCTGAAGTGCAATCTTCTGCTG

CAAGCTCGCAGGATAGCGTGCAATCTGTTACAGTTAAGGCAAAGAAGGCT

AGCTGGAGCATGGGCTCTTCTTTTCCCCTTAAGAAAACAACAAAAGCCCT

TCCCAAGATTCAAATTGACGACGACTCTGATCTGATTGATGAAGACAGTC

TCTTGACTGAGGAGGACCTGAAGAAACCACAACTTCCAGTTGTTGGGGAC

TGTGAGGTGGGGGCAGCAAAGAAAGCATGCAAGAACTGTACTTGTGGCAG

GGCTGAGGCCGAGGAGAAGGTTGGGAAGCTGGAGCTCACTGCGGAGCAGA

TCAATAACCCTCAGTCAGCTTGTGGCAGTTGTGGGTTGGGTGATGCCTTC

CGCTGTGGAACCTGTCCCTACAGAGGTCTTCCACCATTCAAGCCTGGCGA

GAAGGTTTCCTTGTCTGGCAACTTCCTTGCTGCTGACATATGATGGCATC

GCCAACATCGGCAAAACAAGGA (Underlined = GeneRacer Oligo sequence; Bold/Underlined = start codon; coding sequence in bold) (Sequence of 5' RACE product CW88H03-Full_Length cloned into pCR4-TOPO) (Derived from MEST88-H03, GB_ACC# BM079064)

The predicted protein or polypeptide encoded by the full-length cDNA clone of SEQ ID NO:36 has an amino acid sequence of SEQ ID NO:37, as follows:

MSAALAVTDEVALPIRAVGDLAAAAEVSREEVAVITQCAALGGKLPFEDA

SVGAVLAVIKNVESLREQLVAEIRRVLKAGGRVLVQSPAPSSSQKPNTDI

ERKLLMGGFAEVQSSAASSQDSVQSVTVKAKKASWSMGSSFPLKKTTKAL

PKIQIDDDSDLIDEDSLLTEEDLKKPQLPVVGDCEVGAAKKACKNCTCGR

AEAEEKVGKLELTAEQINNPQSACGSCGLGDAFRCGTCPYRGLPPFKPGE

KVSLSGNFLAADI]

A putative promoter (upstream of the transcription site of the gene) for the gene of the full-length cDNA clone of SEQ ID NO:36 has a nucleotide sequence of SEQ ID NO:38, as follows:

gctgtaccagttgaggtactccttgacgtcctcgtacatggtgggcgcca gcgggtgccagatgccggagtcgaggtagagcacggggtcgtcgtacttg atgccggcgcccctaagcaccggcaagtaggatccggcgatcatcttgag -continued gaagttctggaggttgtccgccgagccgccgagccagaactggaggctga ggatgtacagccaggcgtcctgcgccttgtcggagggcaggtacttgagc accttgggcagcgtgcgcacgagcttgagcatgctgtcggcgaagttgct ggagttggacttgctgcgcttgaagagctggaagaaggggctcttggact gccccagctgcgacatgctgaaggagccgagcttgttgaggcgcatgacc tcgggcatggaggggaagacaaggacggcgtccatgcggtcgcgctcctt ctcggccgcggccttgaccttgagcgccagctcctcgacgaagatgaggg agccgatgaagacgttgacgtcggcgaggtcggcgcggaaggtagcccac gacctcgaacgacgcggcgcggcgcgggtcagcgttgagctgctgcacgg cggccgtgacggacgactggtactgcgcctccagcacgacgtagacgacc ttgacccgaggcaggccccgcgggtcggccggcaccacgcgccgcacctc gggcttggtctgcgtgaacaagccgttgccgccggcgaccgcgcaccgga tggcgccggcgcgccgcggctgctggcgacggctgctcaggaggaacgag tgcagcggcacgggcgccgccaggagctgcttctgcgccgcggcggcgaa tggggtggacactagcgacgacgacatggcgcctgctcacaggacggagc cggcgggcggagaaacgcgcgcctggacactgacgcgacgctcgagcgca gtaagtaaaaaaaaatctacactagactactagagtaaggcgcctgttct tggctcgtggctggacaattgttcttggcggccgccgtccctcggaaaca gagcagggaaaggagaagaagcgagcaggggagcgcgggaggcgggaaaa tgtataggttgtccgtgtccacgtccttcgtctcaattaagaagaggcat ccaggctcacaaaatcaatctgaaaacacatgcactgatgcacacttgtg tttgtgtagaggcgcttatatatcatccaaaagacaagtcactcacacgc aaattcgcattggctaacagaagctatttggaatgcagttcagtcgacta acaacgtaggtaccccccgtctccttgttttgccgatgttggcgatgccat catatgtcagcagcaaggaagttgccagacaaggaaacctgccaatcgga gaagcagcagcagtgaacgttcaagatccagagtacaatcgacagacata ttttgatctcctcgagaattctatcaggggaggagacgagtagaactgtt ttaccttctcgccaggcttgaatggtggaagacctctgtagggacaggtt ccacagcggaaggcatcacccaacccacactgcaaagaaaaatcaaggat catttacagatatcaccagacgtgataggtaacctagtccgagtgaacgt atgaaatttcacgagggggcacaagtgccacctgtaagcaatacttacac tgccacaagctgactgagggttattgatctgctccgcagtgagctccagc ttcccaaccttctcctcggcctcagccctgccacaagtacagttcttgca tgctttctttgctgcccccacctcacagtccccaactggtgaaaacatca gtgaaaacatcacttaactgtttaggatccaaacctaaactggctattgc ttacggagttgaactaagttgacgggttttgttgctctaccaactggaag ttgtggtttcttcaggtcctcctcagtcaagagactgtcttcatcaatca gatcagagtcgtcgtcaatttgaatcttgggaagggcttttgttgttttc ttaaggggaaaagaagagcccatgctccagctagccttctttgccttaac ctacaagtggttcaaattagcacaaaaactaaagcctgcacagcaaaact aacatactataacacatgatcttagaccactcactgtaacagattgcacg -continued

```
ctatcctgcgagcttgcagcagaagattgcacttcagcaaatccacccat
cagtaacttgcgctcaatatcagtgttcggctaacggagacaatcataaa
aaaattaagaactttaaatcgacattgcaagagaaacgagacaacaaaga
cagattctgataagttaataccttctgactggatgagggtgcagggctct
gcaccaatactcttccaccagctttcagcacccgcctgatttcagcaacc
aattgctccctcaagctttccacgtttttaatgactgcaagaaccgcacc
aactgatgcatcttcaaaaggcaacttcccacctgatgcatggcagaaca
atagtttggtcacggttttgtgataacacacacacacacacacacacaca
cacacacacacacacacacacacacggcatagcactagcaaagcataa
cacaaattaaaaatcgaacattattgtttaatagaggctcccaaaatcag
gaatgctagcacttggcttattcataaacacacacatccataatcaggaa
gcatacattactgaaccattaaatttaataataaaaattcagatgttgaa
tccatggctgaaattttctgttccttttgaaagtataatcctaactttca
tctccggctgacctggtaatatcttctagctccttttaccttatattttt
ttcagttgcttgagaaatagcggtaggaaaattgacacatgtcattcgta
aatccatgggacttagagcaactccaagagcttcctaagaaattgttccc
caaaacatcatataggggggctgctgaaaaaaatccactaagagcaactcc
aaatgagtgctagaaaatttccccaaaaaatgattattggggatatgtta
aaaaattttaggggtgaattatcatgtatactccaacgattccgttaaac
aaatgcgactcaatctcagccacagtctgagtcttacagacacacacaaa
acctaacatgccggtggcagccacattatcacacaccggaacaaataact
ttgaggcaaaaacacattatgcaagcagagaaacaccagaacagactccc
agctgttgaagtgcaaatgtgttttctatatttgagttacttgctggtaa
atcccgatcgggaatgtaataatcggggagttgcattagcacttttgcag
caagctaagccaactggttgggaatgtcaagcattcttgagcaggagtac
tagtcaagttaacaggcttcagatcccatccaatcattgtcacatttgaa
tataacttgagcgggtagaaaaaaatatcataacaaaggcatcatggactg
aatcctaaacatcataacgaaggcatcatggactgaatagcgatcatcat
aacaacggcaggaaacagactcccaactgaatcatggttaacatggactg
aattgtggtggcactgcatgcagtgcgagatgcatcatatccaggtcaat
tcaggttagcaaatgcaaggccacaggagttgccgccagggaggaggctc
taggcgaggtcacgggagttgcggtggaagttgctgcggattggggaaga
cctttgctcgccaatatttgagggagagtggagctcggatgcgggacgct
gataatttggggggaaggaaaggggaactattgggtggagaatttttttgtt
tttcaccccaaaacatgtttttgggttggttttagcgttcttctggagat
gctcttaagcaactagcacatgagacatggcatagatatcaagaactgca
aggagaggttcaagttcaaatctgaagaagtctgcaagggcatgtccaca
gattcagcggttttggagttgggaaataacttcagctttcttttcttttt
gttgttgagacgttcttttctttttcttttttttttgttgttgttgaggc
gtcagctcgacgttttcattctacacattagaaagtggcagtagcgcaag
```

-continued

```
agataccacagggccaaaactactagtggtactgaaagttttcattcgaa
gaatcagtaagtggcactatcacaggaagaaacattgcaaggccaaactt
ggcgtccactgactgcgcttcaatattacttgagcaacttgctagcctcc
cgatcccggaaggatggtttgataaactaattctctaattgaagtgggaa
cccttaagaaccaaacgtccactactccaaatttgattgcaaaagaaaaa
agaatctagcccattccgcggaatcacgccagaaggctcgctaattgaag
catgcaagcaaggcagcaaagagaacagcacgcatcgacgggttcctgca
tccacaagcacgaacttggcaacttgccatggtcgcctcgagggaaagaa
atagaagaaaaaatggaaagagggcaagacgggggcgaaaccagctaagc
tcaccgagcgccgcgcactgggtgatgacggcgacctcctcccgcgagac
ctcggcggcggccgctagatcccccaccgcccggatcggcagggccacct
cgtccgtcaccgcgagcgccgccgacatggagtcaaatctgcacacgagc
acacgccgagaaccagaagagactcggtgaaaggagtatccccgaagaga
aaaggaattagggttaatcgagggagggttttatctgcacgcccccggat
tcatcacgcgactgctacctgagacgataagacgacgacgaaggcgaaat
ttgatttgggttttgcctggcctcctctcctctcgaagcttcacaacacg
ccgagttatttgatattgtaacaatctcgtcgcgcggcttcaccagttat
tactccgtagttatacttcgctagtttagtatt
(>MAGI4_101388 MAGI4.contigs_w_singleton.fas
5083 bp)
```

A suitable nucleic acid molecule that is modulated (e.g., up-regulated) by nitrogen is the non-symbiotic hemoglobin gene (MEST129-C09.T3Seq) from corn having the nucleotide sequence of SEQ ID NO:39, as follows:

```
catccatccatccatccatttccaatcccaatcccaatcccaccagtgtc
cagtgctcggggaaccgacacagctcctcagcagagtagccagcacgaca
agcccgatcagcagacagcaggcatggcactcgcggaggccgacgacggc
gcggtggtcttcggcgaggagcaggaggcgctggtgctcaagtcgtgggc
cgtcatgaagaaggacgccgccaacctgggcctccgcttctttctcaagg
tcttcgagatcgcgccgtcggcgaagcagatgttctcgttcctgcgcgac
tccgacgtgccgctggagaagaaccccaagctcaagacgcacgccatgtc
cgtcttcgtcatgacctgcgaggcggcggcgcagcttcgcaaggccggga
aggtcaccgtgagggagaccacgctcaagaggctgggcgccacgcacttg
aggtacggcgtcgcagatggacacttcgaggtgacggggttcgcgctgct
tgagacgatcaaggaggcgctccccgctgacatgtggagcctcgagatga
agaaagcctgggccgaggcctacagccagctggtggcggccatcaagcgg
gagatgaagcccgatgcctagtagtggcgattgcgaccagtgtttaaccc
atgacgcagcgccgtcacagatgtcccgtgtggtcttgcgctttagcaat
ttctctctggagggagcgtgtattgttatcttgtgatcgagagcctgtgt
gctgcctttgcttcttgtgattatatagctactgaataaagatgtagcgt
tcttcaaaaaaaaaaaaaa
```

The predicted protein or polypeptide encoded by the full-length cDNA clone of SEQ ID NO:39 has an amino acid sequence of SEQ ID NO:40, as follows:

MALAEADDGAVVFGEEQEALVLKSWAVMKKDAANLGLRFFLKVFEIAPSA

KQMFSFLRDSDVPLEKNPKLKTHAMSVFVMTCEAAAQLRKAGKVTVRETT

LKRLGATHLRYGVADGHFEVTGFALLETIKEALPADMWSLEMKKAWAEAY

SQLVAAIKREMKPDA

A suitable nucleic acid molecule of the present invention is a gene that is up-regulated by nitrogen and contained in a full-length cDNA clone having the nucleotide sequence of SEQ ID NO:42, as follows:

TCGACTGGAGCACGAGGACACTGACATGGACTGAAGGAGTAGAAAATCAC

CTAGCTAGAAAGGAGAGCACCGAGCGCTGCACCACTACTGCTGATATGAG

CACCTGAACCTTCTGGGCAACCACATCCGGTCCCTGCCCCTGATCATCCG

CAGCAGCCATGGCGCAGCAGCAGGAGAAGAAGCAGCAGCAGAGGGGGAAG

CTGCAGAGGGTGCTAAGGGAGCAGAAGGCTCGGCTCTACATCATCCGCCG

ATGCGTCGTCATGCTCCTCTGCTGGAGTGACTGATCCATCTCAAGCATGC

ATGATAAACCTGTGCTCTTTTTTTTTCCTTCTGTTTTTTCCCCTCTTTTT

CCCATCCTTTTCACCTTGCCACTTTGGTGGGCGA (Underlined = GeneRacer Oligo sequence; Bold/Underlined = start and stop codons; coding sequence in bold) (Sequence of 5' RACE product MEST213-C11-Full_Length cloned into pCR4-TOPO)

The predicted protein or polypeptide encoded by the full-length cDNA clone of SEQ ID NO:42 has an amino acid sequence of SEQ ID NO:43, as follows:

MAQQQEKKQQQRGKLQRVLREQKARLYIIRRCVVMLLCWSD (The above sequence is presented after trimming. Cloned in pCR4-TOPO vector at the "TOPO Cloning site".)

A suitable nucleic acid molecule of the present invention is a gene that is up-regulated by nitrogen and contained in a full-length cDNA clone having the nucleotide sequence of SEQ ID NO:44, as follows:

CGACTGGAGCACGAGGACACTGACATGGACTGAAGGAGTAGAAAAACTAA

CACTTCACGTGCCCCCATCCTTTTCCGCCTCAAGTCAAGTGTTCACGGTC

CATCCTCTCGAGAGTCTAGGCCCTTCTCCCGAAGCCGCAGACGCAGAAAA

CGGCTCTGCATATGGAGGCGAAGAAGAAGCCGTCGGCCCCCGCCGCCGTC

GGAGCCGCGCCGCCGCCGCCGGGTAACGGGTACTTCAGCACCGTCTTCTC

CGCGCCGACTGCGGGAAGCGCAAGTGACGCAAAGCATGCGGACTTGTACA

CGATGCTGAACAAGCAGAGCTCCAGAGGGCAGAATGGCAGAGATGGCAAA

TCCCACAGCCGCCCTACTTACAAGGATGGCAAACATGCTCATCCAAATGA

GCCATCAGAATCTCCTTACTTTGGCTCATCCGTGCATTACGGTGGTCGGG

AGTTCTACAGCAGCGTTTTACGGAAGCAACCAGCCAATGAACCCCATACG

GATTACAAGGGGGACAACCCGGATGGCTCTGCTACCAGAGGTGATTGGTG

GCAAGGTTCACTTTATTACTGAATAATCTGCTGGGACCTCTCCCTTTTGT

GAACAAGGAATAAAAGGGGTAGAGCTGAGAATGGTTTGTTGTAGTGTTGG

AAGTGTTGACGCGAGCCGTCAAGCATCGATCAATAGTAATAGTTGTAATA

-continued

GTTGAAAGCTGCGTCGTGACTACAAGCATCCTGTTGGTGGAGGCAGTATT

TTAGATCCATCATCACGCCTGGACAGATGTGGGTGTCC (Underlined = GeneRacer Oligo sequence; Bold/Underlined = start codon; coding sequence in bold) (Sequence of 5' RACE product CW264H08-Full_Length cloned into pCR4-TOPO) (derived from MEST264-H08, GB_ACC# BM350368)

The predicted protein or polypeptide encoded by the full-length cDNA clone of SEQ ID NO:44 has an amino acid sequence of SEQ ID NO:45, as follows:

MEAKKKPSAPAAVGAAPPPPGNGYFSTVFSAPTAGSASDAKHADLYTMLN

KQSSRGQNGRDGKSHSRPTYKDGKHAHPNEPSESPYFGSSVHYGGREFYS

SVLRKQPANEPHTDYKGDNPDGSATRGDWWQGSLYY

A putative promoter (upstream of the transcription site of the gene) for the gene of the full-length cDNA clone of SEQ ID NO:44 has a nucleotide sequence of SEQ ID NO:46, as follows:

aaagcttacacttcataagagattcatagttttatcttacagccatcgtt gtcaacctcaactaccatgcaatccgtttgggattcaactagcaagtaag gggatgtttgtttgggtttataatctgtctggattatataatctaacaac ttttgaactaacacttagttcaagaattgttggattatataatctaggca gattataatcccaaacaaacacttcctaagtcttgtacaggctatagaga ttatttttccagaatggaggagggataatgacaagacctaaaagaaagtt atgtttatggaaaacaaaaaaatggagccaggataatgacacaaaagaaa ggtatgttttctggaataaaaaaaattaaatatatattttgaacttccta agactggaacatgatacctaagctggacagatgatcaaggacagttttac ccctggagacagaaaaacttataagacttagctttctacatcatatcctg ttttgtatgtctcataattaggttccttgtattaagacgaccaacctatc atttgttatacaaaattcgaacgactgctgaagtctcgaagtatatagtc taggctgattaaaatgtaagtatgggttaaagtgctgctggtaacaaact aaatacaactgtatgatgttgttgacaacaagacataactcaaaatggga gcaccaacaaagtgactggcaccggtgatgcaagcataacctaaacacaa ctaatggaaaacgcgaattggaaactatgaaagtgtcccatatatggtat accttgttcacaaaagggagaggtcccagcagattattcagtaataaagt gaacctgaaagtgaagtctagcaagtcagtgtatgagcgtccatgtatat actgaagataatacacaaattgatgcaatgataccttgccaccaatcacc tctggtagcagagccatccgggttgtccccttgtactggatttaaaatt caaaataaacattagacttaagcgctccaaatgatctgtactacgtatat ataaaaaggttctacgtacatccgtatggggttcattggctggttgcttc cgtaaaacgctgctgtagaactcccgaccaccgtaatgcacggatgagcc aaagtaaggagattctgatggctcatttggatgagcatgtttgccatcct tgtaagtagggcggctgtgggatttgccatctgagcacgaatttaaactt ccatagttaaaatcagtgctccagattaattctaagctaagatggtgaga -continued aaaggttttaagtatcgttgtgcttatgaacgcgacctaaatcgaagaga aacgtcaaattgacaagagtacccagaactacctctgccattctgccctc tggagctctgcttgttcagcatcgtgtacaagtccgcatgctttgcgtca cttgcgcttcccttgaatgcaaaacaaagtcaaaatgtcaacgtcatatc caaatagattttgcataatcctataggtcctctattatcaaaatcacccc tcatcagaattaaattgggaaaccgttgaagtccctccacaaatcgcaac atagtaacggactctttcatcaaatcgcaccagctcactaatcatgcaaa aaaattactaagaccccaggaatctgagagcaaaatatcagaacgatggc gtgaagagacggcccgtaccgcagtcggcgcggagaagacggtgctgaag tacccgttacccggcggcggcggcgcggctccgacggcggcgggggccga cggcttcttcttcgcctccatatgcagagccgttttctgcgtctgcggct tcgggagaagggcctagactctcgagaggatggaccgtgaacacttgact tgaggcggaaaaggatgggggcacgtgaagtgttagttgtaggcggcggc ggccggcggggaaggaagcagttggttgttcgcctcgtggcgtcctgctt cggccaacatctgtgccggcatttaaaggcctcgacggagcgactcggtt tcgctatttcggagatcttaaggggctgaatggagaaaattgtgtttagc tttcatccacatccatccaacctgcagtgagacttgcagagtgcagactc ccgtattacagggacggtcctgaataagttagtagttttatttcagagat tcaacgatgttagtatacgaattatttagacacgtttggaatcatccagt tttttagcaatctgatttataaaaagtcaagtgcttccaaacatatcaga ttatgcttcggttcttaaaaatcggactgcctcttccataactaaaatta gtttttaacttggtagaaattagtgattgtaaccgctcttaggtctatgc atgtgattccctcgatgtctttatcccatttgaatatttaattattattt aaaaatttagattaaaaatattaattcaatctatatttaaaattggcaa caaagaaaaacaaagagaataatagaatcaattacttttggaatagagta aggattgaatttgtctttgtgtataacaaagctagaagttggtttccaag aactagcctctaacacgcacacctatttttt
(>MAGI4_139395 MAGI4.contigs_w_singleton.fas
2631 bp)

The present invention relates to a nucleic acid construct having a nucleic acid molecule that is modulated by nitrogen in corn. The construct also includes a 5' DNA promoter sequence and a 3' terminator sequence. The nucleic acid molecule, the DNA promoter sequence, and the terminator sequence are operatively coupled to permit transcription of the nucleic acid molecule.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y.: Cold Spring Harbor Press (1989), and Ausubel et al., *Current Protocols in Molecular Biology*, New York, N.Y.: John Wiley & Sons (1989), which are hereby incorporated by reference in their entirety.

In preparing a nucleic acid vector for expression, the various nucleic acid molecule sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter from *Agrobacterium tumefaciens* (U.S. Pat. No. 5,034,322 to Rogers et al., which is hereby incorporated by reference in its entirety), the cauliflower mosaic virus ("CaMV") 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a nutrient (e.g., nitrogen, including nitrogen in the form of nitrate), a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (see Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the *Chrysanthemum* UEP1 Promoter and Comparative Expression in Florets and Leaves of *Dendranthema grandiflora," Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci.* USA 99:1092-1097 (2002), which is hereby incorporated by reference in its entirety), and tuber/storage organ-specific (Visser et al., "Expression of a Chimaeric Granule-Bound Starch Synthase-GUS gene in transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

A suitable promoter can also be one that is gene-specific, in that it regulates transcription of a nucleic acid molecule of the present invention. A suitable gene-specific promoter gene-specific promoter (derived from MAGI93503) has a nucleotide sequence of SEQ ID NO:41 as follows:

CGTTGTCGGAACGTCCCGTCGATGTTCGGAAACGAGCACGACCCGTCGAC

TCCTGCTTCTTGGCGGAGAAGAAAGGGGACGACGAGCGAGCGTTTTGACT

TTGATTTCCTCGCTAAAACCGGCCGCTGTTTTTGCTTTCCGCGCGAGCCG

CCCACGTTATTGACTGACGCTGGTGCGAGAGCGCTGCTGCCTCTGCGGTT

GCCGTCTGCGCTCCAGTGGTAGCCGAGAATATTGTTAGGTCCGTAGGATC

AGATTTGCTACGTACTAAAAAAATTCCTTAAACTTTAATTGTGTATTTTT

TTTAAAAAAAATTATAGCATTTATCAGCAACAAAACTCTAAAAACATGTT

TAGTTCGCTGCTTAATTTATCACATATTGTCTAAATTTTATATATAAATT

ATTTAATTCGAACGACTAACCAGAACCCAGACCTACAATAAATTTGCCCC

CGCTGCTGCGCTCCCCAGCTCCCCAAGTCCCTAACCCGCCCTCGCTTTGT

CGCCGCGGCACACGGTTTTGGCCGTGGACAGGACAGTTGCACCCTAGCCC

CATTGGCCGATTCCGAGCTAGGAAGGAGTATATGCGTATCGGTAGTAACC

GAGGAGCAACGCAACATGTCCACAGCCCGCGCGCTGGTAACGGGTCCATG

CGTCTTGGCTCATCAGGTGCCCCAAGGGACGCCCTCGCCCGGTCTGACCC

ACCTATATAAACTTAAAACTTGTGCCCCAACATCATCAGTTCGTATCACA

-continued

```
CCCAACCTCCCACTGTAAAAAAGAGCAGCGGAACGTGCGTGCATCCATCC

ATCCATCCATTTCCAATCCCAATCCCAATCCCACCAGTGTCCAGTGCTCG

GGGAACCGACACAGCTCCTCAGCAGAGTAGCCAGCACGACAAGCCCGATC

AGCAGACAGCAGGCATG
```

This gene-specific promoter is a fragment of genomic DNA of maize that is likely to include promoter elements that allow the gene of SEQ ID NO:39 to exhibit nitrogen-regulated expression. Other suitable promoters include those having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46.

The nucleic acid construct of the present invention also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants. Exemplary 3' regulatory regions include, without limitation, the nopaline synthase (NOS) 3' regulatory region (Fraley et al., "Expression of Bacterial Genes in Plant Cells," *Proc. Nat'l Acad. Sci.* USA 80:4803-4807 (1983), which is hereby incorporated by reference in its entirety) and the cauliflower mosaic virus (CaMV) 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would be suitable for use in conjunction with the present invention.

The different components described above can be ligated together to produce expression systems which contain the nucleic acid constructs of the present invention, using well known molecular cloning techniques as described in Sambrook et al., *Molecular Cloning: A Laboratory Manual*, Second Edition Cold Spring Harbor, N.Y.: Cold Spring Harbor Press (1989), and Ausubel et al. *Current Protocols in Molecular Biology*, New York, N.Y.: John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacterial cells, viruses, yeast cells, mammalian cells, insect cells, plant cells, and the like. Preferably the host is either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used. Further, particle bombardment transformation can be used to stably introduce the nucleic acid construct into plant cells.

Another appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., *Proc. Natl. Acad. Sci. USA* 79:1859-63 (1982), which is hereby incorporated by reference in its entirety). The nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention. Transformation can also be achieved using the "whisker" method, as is well known in the art.

After transformation, the transformed plant cells must be regenerated. Plant regeneration from cultured protoplasts is described in Evans et al., *Handbook of Plant Cell Cultures, Vol.* 1, New York, N.Y.: MacMillan Publishing Co. (1983); Vasil, ed., *Cell Culture and Somatic Cell Genetics of Plants*, Vol. I (1984) and Vol. III (1986), Orlando: Acad. Press, which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferase II ("nptII") gene which confers kanamycin resistance (Fraley et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y.: Cold Spring Harbor Press (1989), which is hereby incorporated by reference in its entirety).

After the fusion gene containing a nucleic acid construct of the present invention is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants. The component parts and fruit of such plants are encompassed by the present invention.

The present invention can be utilized in conjunction with a wide variety of plants or their seeds. Suitable plants can include dicots and monocots. More particular, suitable plants can include the following: rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca*, and *zinnia*.

Another aspect of the present invention is a method of expressing a nucleic acid molecule that is modulated by nitrogen in a plant. This method involves providing a transgenic plant or plant seed transformed with a nucleic acid construct having a nucleic acid molecule that is modulated by nitrogen in corn, a 5' DNA promoter sequence, and a 3' terminator sequence. The nucleic acid molecule, the DNA promoter sequence, and the terminator sequence are operatively coupled to permit transcription of the nucleic acid molecule. The method also involves growing the transgenic plant or a transgenic plant grown from the transgenic plant seed under conditions effective to express the nucleic acid molecule in the transgenic plant or the plant grown from the transgenic plant seed. In one embodiment, the transgenic plant or plant seed is provided by transforming a non-transgenic plant or a non-transgenic plant seed with the nucleic acid construct of the present invention to yield said transgenic plant or plant seed. In one aspect, the growing step is effective in reducing nitrogen uptake of the transgenic plant or the plant grown from the transgenic plant seed. In another aspect, the growing step is effective in increasing nitrogen uptake of the transgenic plant or the plant grown from the transgenic plant seed. In yet another aspect, the growing step is effective in increasing efficiency of nitrogen utilization of the transgenic plant or the plant grown from the transgenic plant seed. Transformation of the transgenic plant or plant seed can be achieved using *Agrobacterium*-mediated transformation, the whisker method, vacuum infiltration, biolistic transformation, electroporation, micro-injection, polyethylene-mediated transformation, or laser-beam transformation.

The present invention also relates to an isolated DNA promoter from corn suitable for inducing nitrogen-regulated expression of a protein encoded by an isolated DNA molecule operably associated with the DNA promoter. A suitable DNA promoter for use in this method can be any one of the promoters described herein, including, for example, the promoters having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46. The isolated DNA promoter can be used to prepare nucleic acid constructs as previously described. In a particular nucleic acid construct, the isolated DNA promoter can be operably linked to an isolated nucleic acid that either has a nucleotide sequence (or encoding portion thereof) of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:34, SEQ ID NO:36, SEQ ID NO:39, SEQ ID NO:42, and/or SEQ ID NO:44, or encodes a polypeptide having an amino acid sequence of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:25, SEQ ID NO:28, SEQ ID NO:31, SEQ ID NO:32, SEQ ID NO:35, SEQ ID NO:37, SEQ ID NO:40, SEQ ID NO:43, and/or SEQ ID NO:45. Other suitable genes from corn that can be regulated by the DNA promoter of the present invention include, for example, nitrate reductase, nitrite reductase, Uroporphyrin-III methyl transferase. Expression vectors can be prepared by inserting the nucleic acid construct in an appropriate vector (as described in more detail supra), and transgenic host cells and plants (including their component parts such as fruits and seeds) can be produced by transforming them with the nucleic acid construct containing the DNA promoter.

The present invention also relates to a method of directing nitrogen-regulated expression of an isolated nucleic acid in plants. This methods involves transforming a plant cell with the nucleic acid construct that includes an isolated DNA promoter suitable for inducing nitrogen-regulated expression of a protein encoded by an isolated DNA molecule operably associated with the DNA promoter. This method also involves regenerating a plant from the transformed plant cell. By this method, expression of the nucleic acid molecule, under control of the DNA promoter, occurs in the plant and is upregulated by nitrogen. A suitable DNA promoter for use in this method can be any one of the promoters described herein, including, for example, the promoters having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46.

Although preferred embodiments have been depicted and described in detail herein, it will be apparent to those skilled in the relevant art that various modifications, additions, substitutions, and the like can be made without departing from the spirit of the invention and these are, therefore, considered to be within the scope of the invention as defined in the claims which follow.

What is claimed is:

1. A method of expressing a nucleic acid molecule up-regulated by nitrogen in a plant, said method comprising:

providing a transgenic plant or plant cell transformed with a nucleic acid construct, wherein the nucleic acid construct comprises:

a nucleic acid molecule that is up-regulated in corn by nitrogen;

a 5' DNA promoter sequence, wherein the DNA promoter sequence is a nitrogen inducible plant promoter; and a 3' terminator sequence, wherein the nucleic acid molecule, the DNA promoter sequence, and the terminator sequence are operatively linked to permit transcription of the nucleic acid molecule, and wherein the nucleic acid molecule:

(a) encodes a polypeptide having the amino acid sequence of SEQ ID NO:43; or (b) comprises the nucleotide sequence of SEQ ID NO:42; or (c) comprises the coding portion of the nucleotide sequence of SEQ ID NO:42; and growing the transgenic plant or a plant grown from the transgenic plant cell under conditions effective to express the nucleic acid molecule in said transgenic plant or said plant grown from the transgenic plant cell.

2. The method according to claim 1, wherein said growing is effective in increasing nitrogen uptake of said transgenic plant or said plant grown from the transgenic plant cell.

3. The method according to claim 1, wherein said growing is effective in increasing efficiency of nitrogen utilization of said transgenic plant or said plant grown from the transgenic plant cell.

4. The method according to claim 1, wherein a transgenic plant is provided.

5. The method according to claim 1, wherein a transgenic plant cell is provided.

6. The method according to claim 1, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia*, petunia, pelargonium, poinsettia, chrysanthemum, carnation, crocus, marigold, daffodil, pine, *Medicago truncatula, Sandersonia aurantiaca*, and zinnia.

7. The method according to claim 1, wherein said providing comprises transforming a non-transgenic plant or a non-transgenic plant cell with the nucleic acid construct to yield said transgenic plant or plant cell.

8. The method according to claim 7, wherein said transforming comprises *Agrobacterium*-mediated transformation, whisker method transformation, vacuum infiltration, biolistic transformation, electroporation, micro-injection, polyethylene-mediated transformation, or laser-beam transformation.

9. The method according to claim 1, wherein a transgenic plant seed comprising the transgenic plant cell is provided.

10. The method according to claim 1, wherein the nitrogen inducible plant promoter comprises a nucleotide sequence selected from the group consisting of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and SEQ ID NO:46.

* * * * *

SEQUENCE LISTING

```
<160> NUMBER OF SEQ ID NOS: 46

<210> SEQ ID NO 1
<211> LENGTH: 758
<212> TYPE: DNA
<213> ORGANISM: maize

<400> SEQUENCE: 1

cgactggagc acgaggacac tgacatggac ggaaggagta gaaaatattg cctgctccga     60

cgaccttgaa tattcactgg ccatttaatt tctacttaca agcctgaatg agctagagat    120

ccatctgctt ctgtacgtgc tcgtcaggta cgctcgtaaa aagaaaagaa aaaaaaagaa    180

gagatcgaga tcgatctgtt gacgacgccc ccgtcgccga tatgggcgac ctctctgtcg    240

gccacagccg ccgctggtgc ggccgtttcg cggccgtcct ttgcctgtgc gcggccttct    300

gcaagccaga tgaactcccg atggatccac tgccgaactt gccgccgacg aggtcgctgc    360

agtgcttcga ggacgaacag gtgtacagct gctgcgaggg cgcgtacagg ctaaacccat    420

cgggaatcat cgccgttccc gtcggcgcgg tggactacta ctgcggcggc gcgtgcgtgg    480

tggagacgga ggacgtgctc aactgcgtgg ccagcgccct ggacggcttc gccttctaca    540

acggggcctc cgtggaggac gtgcgctacg cactcaggcg gggctgcagc cacaccgcca    600

gaagaggcga cttcaacgat ttggagccgc atctgggcga ctaccctgac atctatggcg    660

acgatgatga gcacagcttt ggcagcaagg ttgttgcagc tcctctgagg ttgctcgcgt    720

ttcttggcgg tgcggggctg ttcttcctgg gcccttga                            758

<210> SEQ ID NO 2
<211> LENGTH: 178
<212> TYPE: PRT
<213> ORGANISM: maize

<400> SEQUENCE: 2

Met Gly Asp Leu Ser Val Gly His Ser Arg Arg Trp Cys Gly Arg Phe
1               5                   10                  15
```

-continued

```
Ala Ala Val Leu Cys Leu Cys Ala Ala Phe Cys Lys Pro Asp Glu Leu
            20                  25                  30

Pro Met Asp Pro Leu Pro Asn Leu Pro Pro Thr Arg Ser Leu Gln Cys
        35                  40                  45

Phe Glu Asp Glu Gln Val Tyr Ser Cys Cys Glu Gly Ala Tyr Arg Leu
    50                  55                  60

Asn Pro Ser Gly Ile Ile Ala Val Pro Val Gly Ala Val Asp Tyr Tyr
65                  70                  75                  80

Cys Gly Gly Ala Cys Val Val Glu Thr Glu Asp Val Leu Asn Cys Val
                85                  90                  95

Ala Ser Ala Leu Asp Gly Phe Ala Phe Tyr Asn Gly Ala Ser Val Glu
            100                 105                 110

Asp Val Arg Tyr Ala Leu Arg Arg Gly Cys Ser His Thr Ala Arg Arg
        115                 120                 125

Gly Asp Phe Asn Asp Leu Glu Pro His Leu Gly Asp Tyr Pro Asp Ile
    130                 135                 140

Tyr Gly Asp Asp Asp Glu His Ser Phe Gly Ser Lys Val Val Ala Ala
145                 150                 155                 160

Pro Leu Arg Leu Leu Ala Phe Leu Gly Gly Ala Gly Leu Phe Phe Leu
                165                 170                 175

Gly Pro
```

<210> SEQ ID NO 3
<211> LENGTH: 4037
<212> TYPE: DNA
<213> ORGANISM: maize

<400> SEQUENCE: 3

```
ccgcaagagg gagtctttac cgagtgtcac ctaatacgct tggcgaagga cctggtaaaa     60

gggcccacag ggagcttttt gctaagtgtc tgtacagtgg acactcggca aagagtgagc    120

ctttgccgag tgtcactccg tcaccgttac ctggtgtcgt gacgacggct tttctttgtc    180

gagtaccgag tgacactcga caaaaccttt gccgagcgtc cgataaaaag tattcggcaa    240

agaagccgtt gccgtctttg ccgagtgttt tccagacttt gccgagtgtt tcagacactc    300

ggcaaagaac ctgattccga tagtgaaggt cttacacccc gatccacccc aattcgtgcg    360

tattggagca agtacccaaa caaaaccgta ctgggaataa ttacctccgt tcgctgcagt    420

ttgcagaaca gcagttcaat gctacaggac gacgcagctg cagcgaacat gcatgcattt    480

gaactcactc cgttcactga tggacaagag gcatctgggt gactaataaa agaacgacac    540

acacggacag cttctagaag tattggtagc gcatgaacaa caatgccgct gttagcttgt    600

actgaggcac gaaacatgaa tctgacctac tactgacttc tactataata atagtatata    660

gtatggccag gccaggccaa ctccggcgaa aacgggagta cgcatgcaga tggagcggca    720

cattagtagg ctgtttggtt tgaagaatgg gctagtctat catcttctca ctctccactt    780

ttttgtttgg tttgtggaat gaaatgagtt gattcatcat cacctcattc cttatagtta    840

gttagttagt actaatatga ggaatatggt catcccacca aatttgagga atggatccac    900

gatgtaccac cacattttgc atgaagtgat tcctcaaacc aaacaccccc aaatgtaaac    960

cgagtcatgc ctccgatccc aaccttcgtg tttcccacca aacacacgcg tacagaggcc   1020

aagcacacgc acaaaagcaa gcctcgatcg tagcccgtgc ctaaccctgc cgatgccgta   1080

ataaacttgt gtgctccacg caaccatgaa atgaacctag aaatcgcagg ggcgggatgc   1140

gagtgaaaag gagcgggcag gtcaggtagg tttgaactct ctcctataat aatcctagct   1200
```

```
agcacacttg cccagattat attgcctgct ccgacgacct tgaatattca ctggccattt   1260
aatttctact tacaagcctg aatgagctag agatccatct gcttctgtac gtgctcgtca   1320
ggtacgctcg taaaaagaaa agaaaaaaaa agaagagatc gagatcgatc tgttgacgac   1380
gcccccgtcg ccgatatggg cgacctctct gtcggccaca gccgccgctg gtgcggccgt   1440
ttcgcggccg tcctttgcct gtgcgcggcc ttctgcaagc caggtgcgtg ctcaccgtca   1500
acacacgcac cattattcca ccctcccaag gagcacagta caacgcacgt acatatacct   1560
ctcctcaatc gatatatagt tacgtcttac gtactatcta gttaatctat cacgttgatg   1620
tctaatatag actccgcatg gcatatgcat gcagatgaac tcccgatgga tccactgccg   1680
aacttgccgc cgacgaggtc gctgcagtgc ttcgaggacg aacaggtaag ctaacaagca   1740
agagcgtgtt tggtttcatg ctaggacaga gttgcatacc acgtagctat cataagccta   1800
ccacacgtag ctatcacagc ctgtcgattt cgttcggtcg cctgacggta aacatcgctg   1860
cccgagaggc gagctctttt tgacaagcct cgacgaacca aataagccaa gtcctactgt   1920
acgagggcga tcgaggcgcc gaggcctgtg tgatgtgatg ccgtgtgtcg tggtcaccca   1980
ccagctgctg tgtacattgg tccccgtgcc gcgcgtcgta accgcatgcg gcatgccgct   2040
gcatgcaggt gtacagctgc tgcgagggcg cgtacaggct aaacccatcg ggaatcatcg   2100
ccgttcccgt cggcgcggtg gactactact gcggcggcgc gtgcgtggtg gagacggagg   2160
acgtgctcaa ctgcgtggcc agcgccctgg acggcttcgc cttctacaac ggggcctccg   2220
tggaggacgt gcgctacgca ctcaggcggg gctgcagcca caccgccaga agaggtcccc   2280
aagtttctcg cctactagct catctctctc tacgtaccag ccaagctaga tcgactacca   2340
gtctccgcag cagtgcattc ggaacgaccg ctgacaaact gacaggctcg tgttcctgtc   2400
agcgcaggcg acttcaacga tttggagccg catctgggcg actaccctga catctatggc   2460
gacgatgatg aacacagctt tggcagcaag gttgttgcag ctcctctgag gttgctcgcg   2520
tttcttggcg gtgcggggct gttcttcctg ggcccttgaa cgaagatata aaagaactag   2580
cgatgtgatc cgcgtaaata tatactccgt atatagcatg acatgagtat ctagtttgtc   2640
ttatatggta aaccatacta aattttcttg tatggcatta aaaaaaatta agactttatt   2700
tagttatttg actagttgtt ctctctggat cctctaatca gttcgaactc tataagcttt   2760
tttattccac tcctatctag aggtcgcata atatgctaag gtgagatctt gatgtctttc   2820
gttttttaa ctcgataaag ttgttgtgag tctctcttat aaaattattt ttaatgctaa   2880
tattagattt tagtcagaga tatgcagttg accgttttgc actaaaatat ttttgaattt   2940
actatagtat tagttgtcta ctaatcacag ctaaaaccgt ttttattttt agttttttta   3000
taacagaaaa aatatctctg gaaacgaaaa cggcaacaca gtagttcaaa aatatcgaag   3060
acaataattt aacatgaaaa atatatatgt aatgatcgga atctaaaaaa caatcactaa   3120
atataaacat atagtaacat gtactctcaa ttgacctgaa aaaagcacat aacctataga   3180
tccacaaagt aacgaagatt gaagcatgaa aaatagacca tcatacatta aagggttgtg   3240
cttatttagc tctagaataa cctccttaag agcaacttca tttgcaacaa cattgtctag   3300
agttaaagag aatattttct tctctgtaaa ccatttcaat aagcatgaac tgggtctaag   3360
agacaaattc ttaccgttgt gccgacccag aacatgatcg aaatttgtaa ttcgcttctg   3420
tatttgtgaa tcatcatcta cccaatgtac catgatacac atgtaccttt tattctgatt   3480
tgatatccac atctccatgg tagcactgaa gtgacaatta agggttttaa aaaatttata   3540
```

```
caacacatca tttttatgca aaagagatcc attacttctt ttctaacaat gacatgtgac   3600

tttatagaaa atataggctt taaaggttta atgaaatcca taaagtattc atgttcaaga   3660

atgttaaatg ggtactcatg aatgataata gtagtataaa acttcctcaa actaattgac   3720

tcgtcatatt tatatggttg gacaatatat agatatacct accttatgat ctttttctga   3780

tttgagctcc tgctatctta gtaaaacctt atgataacgc ttctaatgca accaaaacta   3840

agttgttcct ctatggcttt tagcactacc tttgtaagtc ctatttttgt agctcagaaa   3900

ctttcatttg gcccaaattt gctccagaga tttgcaattc ccctccacta caacaacata   3960

caaatcaaaa tactgccaaa catctaaagt atacttattt gctactttat ggggtgctca   4020

tcaacattag attcact                                                  4037


<210> SEQ ID NO 4
<211> LENGTH: 932
<212> TYPE: DNA
<213> ORGANISM: maize

<400> SEQUENCE: 4

ggacactgac atggactgaa ggagtagaaa atacagaacc ctgcaactgc aagctaagga     60

gagtgtgatc accaacagct agtgctagtc ccccttcctt ccatccatcc atggcatgcg    120

tcagcacctt ccagagctgc cccattgcca gaagagcaaa gatcaacacc aggtccaggg    180

gcagcagcag tagcgtggcg aaggggtcac caccaccagc cttccagttc cagtgcaggg    240

cgtcgacttt cgcggcggac accagcctcc ggctcgagct ggacgagaac cccgaggcga    300

tcatctcggg ggcgtggccc gggaactgct ccctcctcag ctacgacgac ctccgcgcct    360

acctcgagtc gcaggagacg gcggcccagg cagacgatca gcgcggcgtg gcgctcctga    420

gcgagaccat gtccacaccc gtgctggtgg ccacagcaga ccagaccctg gaggacgtcg    480

agtgccactt cgaggccgtg tcggggcttc cggtcgtcga cagcggcctc agatgcgtcg    540

gggtgatcgt caagaacgac cgggcaagag cctctcatgg gtccaagacg aagatatcgg    600

aagtgatgac atctccagct atcacactat cgtctgacaa aaccgtgatg gatgctgctg    660

ttctcatgct caagaagaag atccacagat taccagttgt aaaccaggac gaaaaagtaa    720

taggtatagt tacccgcgct gatgttcttc gcgtgttgga aggcatgttg aagatttagg    780

agcgcagata cccatgctcg gaagccacag cctcttgtaa atatgtagat gtgcccgggc    840

atggtgtttc tgagtagcag caaagagatc taccatgtat aggagtttct ccttgtaaat    900

aatagtagca cgccaggaga ctccatccca gg                                  932


<210> SEQ ID NO 5
<211> LENGTH: 222
<212> TYPE: PRT
<213> ORGANISM: maize

<400> SEQUENCE: 5

Met Ala Cys Val Ser Thr Phe Gln Ser Cys Pro Ile Ala Arg Arg Ala
1               5                   10                  15

Lys Ile Asn Thr Arg Ser Arg Gly Ser Ser Ser Ser Val Ala Lys Gly
            20                  25                  30

Ser Pro Pro Pro Ala Phe Gln Phe Gln Cys Arg Ala Ser Thr Phe Ala
        35                  40                  45

Ala Asp Thr Ser Leu Arg Leu Glu Leu Asp Glu Asn Pro Glu Ala Ile
    50                  55                  60

Ile Ser Gly Ala Trp Pro Gly Asn Cys Ser Leu Leu Ser Tyr Asp Asp
```

-continued

```
65                  70                  75                  80

Leu Arg Ala Tyr Leu Glu Ser Gln Glu Thr Ala Ala Gln Ala Asp Asp
                85                  90                  95

Gln Arg Gly Val Ala Leu Leu Ser Glu Thr Met Ser Thr Pro Val Leu
            100                 105                 110

Val Ala Thr Ala Asp Gln Thr Leu Glu Asp Val Glu Cys His Phe Glu
        115                 120                 125

Ala Val Ser Gly Leu Pro Val Val Asp Ser Gly Leu Arg Cys Val Gly
    130                 135                 140

Val Ile Val Lys Asn Asp Arg Ala Arg Ala Ser His Gly Ser Lys Thr
145                 150                 155                 160

Lys Ile Ser Glu Val Met Thr Ser Pro Ala Ile Thr Leu Ser Ser Asp
                165                 170                 175

Lys Thr Val Met Asp Ala Ala Val Leu Met Leu Lys Lys Lys Ile His
            180                 185                 190

Arg Leu Pro Val Val Asn Gln Asp Glu Lys Val Ile Gly Ile Val Thr
        195                 200                 205

Arg Ala Asp Val Leu Arg Val Leu Glu Gly Met Leu Lys Ile
    210                 215                 220


<210> SEQ ID NO 6
<211> LENGTH: 3987
<212> TYPE: DNA
<213> ORGANISM: maize

<400> SEQUENCE: 6

caacgtggag taggcaagcg ttggtcttgg ccgaaccacg ggataaacca ctgtgtcaac     60

tctgtgattg atctcttgtg gtattgtgtt ttgttgagac tcttttctag ccacttggca    120

tttagtgtgc taacacttaa caagtttttg tggctataag tttaagtttt acaggatcac    180

ctattcaccc ccccccccctc taggtgctct caagttgaca ggtgtctcca tggtgcctaa    240

ttgagccgtt cttttacgct atccattcga ttggtttggt gggtatgtgt ggtctggctc    300

ttgcgatgtt tgcccgctgg aaacgaaaca atcgtgcata cgtgcgcatg caattaacgg    360

tggtgttttt ggcctgtctt gcagcagcgg gtgcagcatt ggcttggcat aagcacgcaa    420

ccaaacaaag actacctttt ggtcaatgca tgcgaagaat ctgtacgagc gggcgtagac    480

aaccaatgat gcgatataaa atttaaggat tgaatcatat tagaatcgag ctttatttct    540

attcattttc gaactaattt tttaagtatc ctaacttatt gtgaagaaac gtaaatattt    600

agatcccgat ccattaccac ctctactcat acgtgaaacc aaacacgcgg aatatccttc    660

tggttcaaat atgcagaagt caatgagcag gacttctgct tgtttgttca gtctctcagg    720

cagggttaca ggaggcaata caagatgttc tccaacgatt ccctgaatcg ttcacccccct   780

ctctcagtcc tatgattcac tcactcaccc ctccccctct tctccgtatg acaggaaatc    840

cccctagagg gggagagctc taagctcccc ctccactaat taatcatatt tactgtgaaa    900

ttacctattt gtagtgtaat taatagttag caatgtgtat tacgtattat aaatattgta    960

ccaatattta aaactcaaaa aactaatgta taaaaatcaa atagtgcact taaagtatta   1020

agggcagagc tgaatagggg gattgttgga gaagtgaaga aataggggga agaatagttg   1080

agaaggggta tttaaatatg aatagaaagt atgaatggag ggaatgtttg gagagagctc   1140

aagaacaagg gacactgagc tgcctacaac acgtggccct ttttgtccct cttcttttttt  1200

ttctttcgca tctgctggct acaagaggac acgcccttct attcgccgta tagagcagtg   1260
```

-continued

```
tctgtgaagt aaaagagaac tatcctccaa ggcttatttt gagtgtatta ctcctggatt   1320
cttgaatctt agctggtatg gtatggtaag gagttacgtt gtccaggaga ttccaactta   1380
cggatccaca ctgaaaagtt tgtattaccc atttgttagg ccccgtttca atctcacggg   1440
ataaacttta gcttcctgct aaactttagc tatgtgaatt gaagtgctaa agtttagttt   1500
taattaccac cattagcttt cctgtttaga ttacaaatgg ctaaaagtag ctaaaaaaag   1560
ctgctaaagt ttatctcgca agattggaac agggcctata tggtcacttt agagaggcat   1620
ggaggtttaa tagactatga cattcgtacg tggtcacctc aacaaacttt attgtttgac   1680
cgaaccatag attgaattgt gtgacattgt tctttgctcg tattattatt aatagaaagt   1740
aaccttcttg ggtgcggccc atacggtcct gagcgcacta aatgaggcct cattggccgc   1800
ggcccattcg atcctcaacg cactggataa agccagcgtg gcgtggctaa accacttcgt   1860
ttggcatggg cctgtcggtg cacttgccca aaccatgagc ttgtaccaaa actcgctagt   1920
ggtagtggta ttagtagtga agaacttctg caacttcaaa ctcaccgatt ctctcgcggt   1980
cagtttggaa gctaaaatat cggtggaaat tagagagaat ttgataagct aaaatctctt   2040
tattatttaa aattgaataa taaataaatt ttaactcctc caatcttctc cgtttttatg   2100
tctcccaaac tcagtgtacc agatcatatt cctttcatta aaaaaaaggt gaacaaagac   2160
gccaccttat ccactgccac gtgacagggg gccaggggaa tctcggcggc cagtggcggc   2220
acgccacgcc ggccggtcgc ccccgtcgct gtacaagata cccatgattg gagcggggca   2280
ggtgcagagc agcaacgcca cggctgcatg agatcaagaa gctgccttca cttcgcccac   2340
tgcagcatgc cgtgtcgccg tcagagttgg gcgcatatcc agataaaaaa aacttgcctg   2400
cttgcactgc agatgcgttg tttttgctaa cagcaagcag gcaagtcagc agcctaacct   2460
tctttgatat ttacagagaa gatgaaaagg agaactggag agcagtagtg gcagtcactt   2520
cactggtcaa gcattcctat ccacctcggc ccacctccac ctccctgaca gtcattttgt   2580
tatataaaac ccatcaagct cccctgcaag gagatacaga accctgcaac tgcaagctaa   2640
ggagagtgtg atcaccaaca gctagtgcta gtccccccttc cttccatcca tccatggcat   2700
gcgtcagcac cttccagagc tgccccattg ccagaagagc aaagatcaac accaggtcca   2760
ggggcagcag cagtagcgtg gcgaaggggt caccaccacc agccttccag ttccagtgca   2820
gggcgtcgac tttcgcggcg gacaccagcc tccggctcga gctggacgag aaccccgagg   2880
cgatcatctc gggggcgtgg cccgggaact gctccctcct cagctacgac gacctccgcg   2940
cctacctcga gtcgcaggag acggcggccc aggcagacga tcaggtacac ttcgatctcg   3000
cggcttcttc agttcttgtt accattgttt acatctcctc cagctcttgc taacccggcc   3060
tggacgggtc tcctcctctg tggatatata cagcgcggcg tggcgctcct gagcgagacc   3120
atgtccacac ccgtgctggt ggccacagca gaccagaccc tggaggacgt cgagtgccac   3180
ttcgaggccg tgtcggggct tccggtcgtc gacagcggcc tcagatgcgt cggggtgatc   3240
gtcaagaacg accgggcaag agcctctcat ggggtcagca cctcgctcct ctccctccac   3300
ctctttcttt ctcatggggc cagggccatg catgcgcatc aagctgctag tttctcatag   3360
acaggcaaat aagaacgacg tacgtccgtt cagtttaccg gtctgtttct acttgtgaca   3420
gtccaagacg aagatatcgg aagtgatgac atctccagct atcacactat cgtctgacaa   3480
aaccgtgatg ggtaatcttt tttgcatcgc ttttcttttc ttttcttttc ttttctgttc   3540
atgtgtgatt tttaacaagt tgaatctaac agtgcatgcc taacgtctac agatgctgct   3600
gttctcatgc tcaagaagaa gatccacaga ttaccagttg taaaccagga cgaaaaagta   3660
```

```
ataggtacgg tgagtgagtg tcagaatgct cacaagccag cagagattaa aaaaaaaaac   3720

tgcatgccat acacttaatt agtattatcc ttaattatca ttgacaacac agagattata   3780

tgttgcaagg gctaatgggg ttctaaacac tgtcaacagg tatagttacc cgcgctgatg   3840

ttcttcgcgt gttggaaggc atgttgaaga tttaggagcg cagataccca tgctcggaag   3900

ccacagcctc ttgtaaatat gtagatgtgc ccgggcatgg tgtttctgag tagcagcaaa   3960

gagatctacc atgtatagga gttctcc                                       3987
```

```
<210> SEQ ID NO 7
<211> LENGTH: 1178
<212> TYPE: DNA
<213> ORGANISM: maize

<400> SEQUENCE: 7

cgactggagc acgaggacac tgacatggac tgaaggagta gaaacccttc tcgctcggtt     60

gctcgggagc tttccccttc ctgttcctga agcttccgac atccgaccgc ctcctcctcc    120

tcgttctact cgccgcccct tctagaatca tccagaggcg tgccggtgaa gcgcgagagc    180

ggtgaggcat ggcgatgcag acgggggtcg cgacctccaa ggtcctcatc ctcgtcggtg    240

cagggatgac gggctcgatc ctgctgcgga atggccgctt atctgatgtg ttgggagaac    300

tccaggagat tatgaagggt gtaaatcaag gaacttcttc gggtccctat gacattgcac    360

ttattcaagc tcagattcgg aatttagcgc aagaagtcag agatttgaca ttgtcaaagc    420

ccattaccat actgaatggc aaatctgact cgggaggcag tttatcatcc tacatactgc    480

cagcagcagc agttggagca atgggttatt gctacatgtg gtggaagggg ttgtctctct    540

cagatgtcat gtttgtcaca aaacacaaca tggcaaatgc tgttcagagc atgtcaaagc    600

agttggagca agtttcatca gcactagctg caacaaaaag acatctaact caacggcttg    660

agaatttgga tggcaaaatg gatgaacaag tagaggtctc caaagctatt agaaatgagg    720

tcaatgatgt taaagatgac ctgtctcaaa ttggatttga tgtcgaatca attcagaaaa    780

tggttgctgg attggaggga aagatcgagt tacttgagaa caaacaggac gtggctaata    840

ctggtatctg gtatctctgc caagtagcag gcggtttaaa agatggaata aacaccaggt    900

tttccagga aaccagtgag aagctgaagc tctcacattc agctcaacct gaaaacaagc    960

cagtgaaggg gcttgaattt ttttcggaaa gcaccatgga acagaaagta gctgactcca   1020

aaccaattgc ggtgacagtc gacgctgaga agcctgagaa aaccgctgct gtaatgggca   1080

ccacagtgca caggtctatc aggttctcat atcggaaggc aggccttgct ttgtgatcaa   1140

atcctctccg cttgagatgc acgtggcctt cctggttg                           1178

<210> SEQ ID NO 8
<211> LENGTH: 315
<212> TYPE: PRT
<213> ORGANISM: maize

<400> SEQUENCE: 8

Met Ala Met Gln Thr Gly Val Ala Thr Ser Lys Val Leu Ile Leu Val
1               5                   10                  15

Gly Ala Gly Met Thr Gly Ser Ile Leu Leu Arg Asn Gly Arg Leu Ser
            20                  25                  30

Asp Val Leu Gly Glu Leu Gln Glu Ile Met Lys Gly Val Asn Gln Gly
        35                  40                  45

Thr Ser Ser Gly Pro Tyr Asp Ile Ala Leu Ile Gln Ala Gln Ile Arg
```

```
    50                  55                  60

Asn Leu Ala Gln Glu Val Arg Asp Leu Thr Leu Ser Lys Pro Ile Thr
65                  70                  75                  80

Ile Leu Asn Gly Lys Ser Asp Ser Gly Gly Ser Leu Ser Ser Tyr Ile
                85                  90                  95

Leu Pro Ala Ala Ala Val Gly Ala Met Gly Tyr Cys Tyr Met Trp Trp
            100                 105                 110

Lys Gly Leu Ser Leu Ser Asp Val Met Phe Val Thr Lys His Asn Met
        115                 120                 125

Ala Asn Ala Val Gln Ser Met Ser Lys Gln Leu Glu Gln Val Ser Ser
    130                 135                 140

Ala Leu Ala Ala Thr Lys Arg His Leu Thr Gln Arg Leu Glu Asn Leu
145                 150                 155                 160

Asp Gly Lys Met Asp Glu Gln Val Glu Val Ser Lys Ala Ile Arg Asn
                165                 170                 175

Glu Val Asn Asp Val Lys Asp Asp Leu Ser Gln Ile Gly Phe Asp Val
            180                 185                 190

Glu Ser Ile Gln Lys Met Val Ala Gly Leu Glu Gly Lys Ile Glu Leu
        195                 200                 205

Leu Glu Asn Lys Gln Asp Val Ala Asn Thr Gly Ile Trp Tyr Leu Cys
    210                 215                 220

Gln Val Ala Gly Gly Leu Lys Asp Gly Ile Asn Thr Arg Phe Phe Gln
225                 230                 235                 240

Glu Thr Ser Glu Lys Leu Lys Leu Ser His Ser Ala Gln Pro Glu Asn
                245                 250                 255

Lys Pro Val Lys Gly Leu Glu Phe Phe Ser Glu Ser Thr Met Glu Gln
            260                 265                 270

Lys Val Ala Asp Ser Lys Pro Ile Ala Val Thr Val Asp Ala Glu Lys
        275                 280                 285

Pro Glu Lys Thr Ala Ala Val Met Gly Thr Thr Val His Arg Ser Ile
    290                 295                 300

Arg Phe Ser Tyr Arg Lys Ala Gly Leu Ala Leu
305                 310                 315
```

<210> SEQ ID NO 9
<211> LENGTH: 3385
<212> TYPE: DNA
<213> ORGANISM: maize

<400> SEQUENCE: 9

```
taactctaca agctaagaat caacatgtat gcaattccat aataatcggg catcatctat      60

cactcattgc taacttcagc actgaacatg atttcaagag tttttagcag aactactatg     120

cgggtgatct cctttcagat gtagatggtt tagaagtgta cataagcttg caggggctta     180

aggaactgtt tatttaatct tctgtgagca cgaacatcca tagaagaact atctgaactg     240

aagctaaaga tttgcatgaa atggtaattt gtacacatta agtgcatcat gcaaacagaa     300

cgagtacaca gtgaaacgat acagacctcc cgagtcagat ttgccattca gtatggtaat     360

gggctttgac aatgtcaaat ctctgacttc ttgcgctaaa ttccgaatct aatatcaagc     420

acgagcatgc aaagttaagt agaaatgaat aattttaccg agatggaaag aagcaagaga     480

aacttctaag cagatgctga cactgagata gtgagatgta agatgtattc catatgagga     540

agagcatacc tgagcttgaa taagtgcaat gtcataggga cccgaagaag ttccttgatt     600

tacacccttc ataatctcct agaaacacaa aaggtacatc attgccttaa ataaacattt     660
```

```
actaggaagt ttcagagcat accatcaaaa tctgtatgat atgtatcagg aatcactaac    720
tagtgaagca taagttatgg tacgcaaaac ttccgagtgc caattgggcg ttgatgtaat    780
tttatcacat ggtgttaatc acatccacat atagacagaa tcaacgcttc tagtacccca    840
tcgccaagtc attcaaaaaa tatcaggtat cagctatctg acaacgctca actatccaaa    900
ccgtatgaaa gtgcgtgtaa tcaaaatgaa catatttttt tcggggttgg gtgtgggggg    960
tataccgacc tggagttctc ccaacacatc agataagcgg ccattccgca gcaggatcga   1020
gcccgtcatc cctgcgagga caccatttca ccacgtaagg tgtcgaaaca acagccgatt   1080
ggggaaaata gcatcaaatc cgagagagat ttgatggggg cgagaggtcg atggcggtga   1140
tgagaagagg acctgcaccg acgaggatga ggaccttgga ggtcgcgacc cccgtctgca   1200
tcgccatgcc tcaccgctct cgcgcttcac cggcacgcct ctggatgatt ctagaagggg   1260
cggcgagtag aacgaggagg aggaggcggt cggatgtcgg aagcttcagg aacaggaagg   1320
ggaaagctcc cgagcaaccg agcgagaagg gtgcctggac ccgggaccgg gacctgagaa   1380
tttcgtgtgt cacaaacaaa cagggtgaac cagttgtgaa atgggaccac gtgtcagtga   1440
agaggtgagt agtagtattt gtgagttgtg actcgagaaa tgccgctgcg ggctgcggcc   1500
tagccacagc cacgtcagca atgtcgaaag tcgaaaccaa ccccactcca cgtctccccc   1560
aggagaagcg accattcaaa gccgccggga gctcggcgtc accgccgcga gctcgacacc   1620
tcgacacctc gtgccgccgc agcgcttgct ttcgtccccc ttacgccact cccacttggc   1680
cacttcagcc accatctccc tgaagctagt ggctaacctc ctcaccgcca tgggcacccc   1740
tctcctcatc cccttctcg tcaccctcca gctgttcact acctcctccc ccgcggtcgc   1800
gtcgtcacac atctccgcca tcatctcgca gtcgggcctc gacttcgcca aggacctgct   1860
cgtatcccat gccgttgcga ccctcacgcc catgaacgtg ccggacatcg agaggaccat   1920
gagcataccc ctcgtgggca ccgtccgcat ggccgcatcc gggattgtgc tccacggcct   1980
cgccgtcacc aactccaccg tcgctgtggg ggacgcgggt gttgtcgtgg ccgcctcgtt   2040
ggccagcgcg aacctcacca tggagtggaa ctactcgtat gacgcctgga ttgtgaccat   2100
atccgacagc gggaatgctt cggtccaggt ataaatgagg ggaacatata ctgtgcagtc   2160
atattagtgc aaccgtgcaa ttaagcaatg atgcatcgat ccaatcaaaa tccaactatg   2220
attgctattt taggtggaac atggttagat gcaaaacagt cctgtttggt tgatattcga   2280
tattccatca gttatgttcc ccaaggcgtg gcttgctgat tggtggctgt taattgaatc   2340
ataagatact gcccgttttt ttaatatact gagtaggaga tatacgcatc ttttatgcta   2400
ttaagtatag actgatcgcg cgacacttga attttggaat atctattttc tgtcagatgt   2460
cagaagtaga atcaattatc ttagaagtgg gtgctaattc acacctatta ctatatttaa   2520
aatgggatta atataaacac tctatttttc tcgaaagcgc aagagagctg cgcgaaaata   2580
tattaagaag aagtaaaagg tccaaaagga ccccaagata cagataaggc cgacctacgg   2640
cggccaataa caagcataaa tgaaaccatc catgacaaaa acactgctac cagaacagca   2700
ctacatctat ctagctaaca ggtagacctg ggataggggc agtaagcaag gacagcttct   2760
ttgcaccagc cataacccaa agatcaatct ccaaaccaac acttctaata gcaacagcaa   2820
cactaggact cttattgtca aaaacgtagc cattgcgatg tttccaaagg gtccaaacac   2880
caagaatgac aagagaatta agaccatttc ttgcaatccc aggagtcttg gtgatcaagt   2940
cttgccacca atccataaaa acctcttcac aggactgatg ggccaagtgt tgtagattta   3000
```

caagaagaag cagcttgaac caaaattctc tagcaaaaac gcagcccagc agcatatgat 3060
ttaaggtttc ctgatcctga tcacataatg gacatctctc cggatgatcc atacctcttc 3120
tttgcaacct atcagctgtc cacaccttct tgtgagcgac caaccacatg aaaaatttag 3180
atttcggagg agcccaagtc ttccaaatta tatgaaaagg ctcaaactca attgacccaa 3240
taaagaaacc cctataagct tccttggaag aatattttcc attggcagca aggcgaaaga 3300
aatgcttgtc ttcaacatga ggtcttagct gaaccaaatc taataaatcc cacaagagga 3360
gatactcgtt gatacaccca ctgaa 3385

<210> SEQ ID NO 10
<211> LENGTH: 420
<212> TYPE: DNA
<213> ORGANISM: maize

<400> SEQUENCE: 10
cgactggagc acgaggacac tgacatggac tgaaggagta gaaaaactcc caaatccttc 60
gtttcgtcgt ctccacacgc aatagcatcc gagcaaagaa gccaaagagc aactgggagc 120
gaggacggga ggcaacaagc ggcggcggca tggaccggaa cctgagcggg tttctgatcg 180
ggtgcctggg cgccgccgtg acgctgctgg cgtaccagca gacggtggtg accagcacgc 240
agagcgtcgc ggcgggcttc gtcgtcatcc tcttcgccct cttcgtcaag gaaggattca 300
tttccctctg aatctctggt gcgcgtcagc cagccatgca tgaggaggcg tcatcgctcc 360
gctgcctgta tttctgctcg ctagttcagt cccgcagctg ccgctgtgct cgtcaggttc 420

<210> SEQ ID NO 11
<211> LENGTH: 53
<212> TYPE: PRT
<213> ORGANISM: maize

<400> SEQUENCE: 11

Met Asp Arg Asn Leu Ser Gly Phe Leu Ile Gly Cys Leu Gly Ala Ala
1 5 10 15

Val Thr Leu Leu Ala Tyr Gln Gln Thr Val Val Thr Ser Thr Gln Ser
20 25 30

Val Ala Ala Gly Phe Val Val Ile Leu Phe Ala Leu Phe Val Lys Glu
35 40 45

Gly Phe Ile Ser Leu
50

<210> SEQ ID NO 12
<211> LENGTH: 1736
<212> TYPE: DNA
<213> ORGANISM: maize

<400> SEQUENCE: 12
gatacgactc tcgctggtat ataaaatctg tttcgtagat aaacatgaaa ccagaatttt 60
tgatcaccat atacttgttt cagaagcaaa ttggggacac catatacttg ttgccttcaa 120
acgaccgtac aataagttca gactgaccat ctgaatgtca caagagctag tttagagcag 180
caagaaattg tcaagtgacc tagacatccc gaaccgacgc ttcccagact tagcccgacc 240
ttccgggtcc ttcataagct gactccgtgg cccctcacca gaccaacgcc gcagccgttg 300
accttgcggc tttttatccc catccggcca tccccaaccc aactcccaaa tccttcgttt 360
cgtcgtctcc acacgcaata gcatccgagc aaagaagcca aagagcaact gggagcgagg 420
acgggaggca acaagcggcg gcggcatgga ccggaacctg agcgggtttc tgatcgggtg 480

```
cctgggcgcc gccgtgacgc tgctggcgta ccagcagacg gtggtgacca gcacgcagag    540
cgtcgcggcg ggcttcgtcg tcatcctctt cgccctcttc gtcaaggaag gattcatttc    600
cctctgaatc tctggtgcgc gtcagccagc catgcatgag gaggcgtcat cgctccgctg    660
cctgtatttc tgctcgctag ttcagtcccg cagctgccgc tgtgctcgtc aggttcttgg    720
aaaaatactg taatagcgta gtgactttta tgtacgacac ggatggttgt tgctggctga    780
agggtctact ctgtcgaaat cgatgtatct tagtttatgc tacttgaaga acagcagact    840
gcagatcagc agagttcttg ccttcttacg ctaattaata attattggta cacgaatcct    900
gattgtgttg agccttcttg ccgttgctcc ttccctacta acatctcggc ttgccaattc    960
acctatgtat gtttgctttg tatattagtg caggtattaa tggccgcctg taagtgagtt   1020
tgttctccct tgttgaacta ataaaattgg catgaattca ccccaaaaag attgatgctg   1080
tttctcacta gttttcagcc tcagacgact atagatgtcc aaacagtgcg gaccgtccat   1140
ttgaaacttg acccgtcacg attttagtcc ggtccaagca tggccaagca gggttggtaa   1200
cggcacgacc tgtttagcgt gccgggtttg ggcagctaca gaggcccgcg tgttttggtc   1260
cgatccgaca cgagcaatgg gccgacacag cggcggccca tttttcatat ggcatatggt   1320
gccagcggcc acacgccccc ccaaccaggc cacacacccg aaccctatct ctaatcccct   1380
cacccccteg ggccctccgt ccccatctct agcgattcgg cgccgtcgtt ctcgcccgtt   1440
gcatcccgtc ggctcttgac ctcgacggcg gacgactctc catcgctgtc gtatgtggtg   1500
ctccgacctg cttggacttg gagttcctcc gtcctccctc gtcactccct ccgtctgcga   1560
ctggggactc cctaacccta acccctccgg tctccggatt cggtggttct agctcctcag   1620
ctgtgcaagg ttcgtttatc tcgtctaatc ccctccagat ttggtgtcta gctgatgtct   1680
ggtgctcgtc tgtggtgtct ggttgccgtt gccggtggtc gtcacctgtt gctcct       1736
```

<210> SEQ ID NO 13
<211> LENGTH: 791
<212> TYPE: DNA
<213> ORGANISM: maize

<400> SEQUENCE: 13

```
cgactggagc acgaggacac tgacatggac tgaaggagta gaaatcttgg atctggtggt     60
gggttcatcc ttggcccact tcttcttgag cttgggtgca taccgcaggt ggcaagtgca    120
acagcaacat tcgtgatgat gttctcctcc tccctctctg tggtggagtt ttacttcctg    180
cacagattcc ccctgccttt tgctggctac ctcatcttca tttccatatt ggctggattc    240
tggggccagt gtttggttag gaagatcgtg catgtgctca agagagcatc gcttattgtc    300
ttcatcctct cctctgttat cttcgtcagt gctcttacga tgggtgtcgt tggaacccag    360
aagagcattt cgatgatcaa caatcacgaa tatatggggt tcctcaactt ctgcgagtaa    420
ctcaaacacc atcagactgt cgatccgtcc gggagaatcc aggccaatgc ctaattgacc    480
tcatctccct caaaatctag aagaataaag tcgccgagta tgtgcacaag ttagctcctc    540
gccaacatgt gcgcatttag accgacagag tcgctgtagt gaattcagct cgtgttagct    600
cctggctaac gagctgacca tacggcttta gttttgtgaa gtgggcgcga tttcgtcatg    660
tcatgcatgt gttagctcct ggctaacctg caaatgcgtg tgttggtgca ggtttttgtc    720
acgtctgcgt cagctcctgg ctgaccagca gttgtttgtc gttcattctc tgcgtcagct    780
cctggctgac c                                                         791
```

-continued

<210> SEQ ID NO 14
<211> LENGTH: 94
<212> TYPE: PRT
<213> ORGANISM: maize

<400> SEQUENCE: 14

```
Met Met Phe Ser Ser Ser Leu Ser Val Val Glu Phe Tyr Phe Leu His
1               5                   10                  15

Arg Phe Pro Leu Pro Phe Ala Gly Tyr Leu Ile Phe Ile Ser Ile Leu
            20                  25                  30

Ala Gly Phe Trp Gly Gln Cys Leu Val Arg Lys Ile Val His Val Leu
        35                  40                  45

Lys Arg Ala Ser Leu Ile Val Phe Ile Leu Ser Ser Val Ile Phe Val
    50                  55                  60

Ser Ala Leu Thr Met Gly Val Val Gly Thr Gln Lys Ser Ile Ser Met
65                  70                  75                  80

Ile Asn Asn His Glu Tyr Met Gly Phe Leu Asn Phe Cys Glu
                85                  90
```

<210> SEQ ID NO 15
<211> LENGTH: 2189
<212> TYPE: DNA
<213> ORGANISM: maize

<400> SEQUENCE: 15

```
cttgggcggt agagcttttt attagctttt caaaaagttc aaggtcatca aggtcagagt     60
ttaaatctaa aagctatgcc taaaatataa aatgggtcat actgagcacc catacatatg    120
atgatcttgt ccagtaccac atctgataca cacagagcat tacggtgacc catgttccat    180
atcttaaggt aacgaaggtt tgtcctaagt taaagttttg aaactttgac aacaatatct    240
acaaaaataa ttatttttta cttaaagaaa ttatatattg tgctagatgt tttaataata    300
aatataatag ttttattttt atttagtcaa tgtttatgaa tattttgtta ttaatgataa    360
aagtttcaaa attttgactt agtataaact ttcgtgatct taagataggg aagagaggga    420
gtgagtaggt atcaattgca cccaggtaat gatcattttc aacggtcaaa ttactaaaaa    480
tagccgttac caaaaactca acagtgtaca tgatgtggag cgatccgggg ggagacaccc    540
acttacgttc aatgaaaatg ctagtccacg aaggagacgg aagcccaccc tggcctctct    600
ttgaggcgaa gccacgttcc ggccaatcgt ctcacagcct ctatgcaggc tggaatgtca    660
cccatgctgc acctcacctc aaccatcgta aatcttaagg accattcttc ttaattaact    720
catttgcaag ggtttgtagc gccgctttac cttagtacat gtgttacagt aaacaaacaa    780
ttgccagtgc tttatatgat ttcgatccat catattttag gtccaaaaca gcatcttcac    840
tcaaagagac agattaaagc tgtttggact gctttagcta taataaaaat actgtagaaa    900
aaacagaagt cggtggaagc cgcagcgaac atgttctgat tttcacggaa atacggcttg    960
aaacgcactc ggcttgcaca aacagaatgg gaattgactg atatttacaa tgttccatgc   1020
aacaaatatt tgcagttttg cagcctagcc tggtgctagc gcaagaatga acaacaaata   1080
actgctggtc agccaggagc tgacgcagag aatgaacgac aaacaactgc tggtcagcca   1140
ggagctgacg cagacgtgac aaaaaacctgc accaacacac gcatttgcag gttagccagg   1200
agctaacaca tgcatgacat gacgaaatcg cgcccacttc acaaaactaa agccgtatgg   1260
tcagctcgtt agccaggagc taacacgagc tgaattcact acagcgactc tgtcggtcta   1320
aatgcgcaca tgttggcgag gagctaactt gtgcacatac tcggcgactt tattcttcta   1380
```

-continued gattttgagg gagatgaggt caattaggca ttggcctgga ttctcccgga cggatcgaca 1440
gtctgatggt gtttgagtta ctcgcagaag ttgaggaacc ccatatattc gtgattgttg 1500
atcatcgaaa tgctcttctg ggttccaacg acacctgaaa ctcaccgaaa caagaggcca 1560
ttaggagaga agttaaaaat caaactagat tgatttagac gaaacaagta aaagagctaa 1620
tataatgcta catccgttct cgaatatttg tcgtccgtta gttcattttt taaaatgaac 1680
taaaacgtga caaataaaaa agaacggaga atggagtgag tattccttaa gattattttt 1740
ctcaaggatg catgctataa ttgcaaaatc aatttaagca acaccggtac gtttagttca 1800
atttaagcaa caccggtacg tttagttcaa ttcaacttgg agcggtatca ggttagcaat 1860
ttgccaagtt taaagctaag tagcaagtca atgagttatc aataggttca tacccatcgt 1920
aagagcactg acgaagataa cagaggagag gatgaagaca ataagcgatg ctctcttgag 1980
cacatgcacg atcttcctaa ccaaacactg gccccagaat ccagccaata tggaaatgaa 2040
gatgaggtag ccagctgcag atagagaaac agtgcaagtt attaactcgt taccatataa 2100
caatcacact tatgaaaacg tctacatttt gaggaattgg aatctaacta atagagtagg 2160
ttatttcttt agaacgtgac atttcataa 2189

<210> SEQ ID NO 16
<211> LENGTH: 839
<212> TYPE: DNA
<213> ORGANISM: maize

<400> SEQUENCE: 16
cgactggagc acgaggacac tgacatggac tgaaggagta gaaaaaagtg ctcccggaag 60
actccaagct gcagctaccg gccttcctct cccccattcc aattccgaga acaggggcgg 120
cggagtcaac caggtacgat gtgctcggta gcgaggctgg cgtttgtgct tgcactggcc 180
atagccgcct cgtcaattga ggttgcggag agcagagatt ttaatatctt tgctcagggc 240
agcttgcctg atgcaaccaa gggatcgtct ggtctagctg caaccagtgg aaagttgtgt 300
cagttatgcg agcagtactc atccgaggcg ctcctctatc tcacacaaaa cgagacccag 360
actgagattc ttagcattct acaccatgaa tgtgccagcc ttgcccctct caaacagcag 420
tgcatcacgc tggttgacta ctacgtaccc cttttcttct tggaggtctc catggttacc 480
cctgagaagt tctgcgagtc gatgcatctc tgcaagaagg ggatgaagat tagcctaccc 540
acccgggagg gtacttgtgg tttgtgccac catgttgttg ttgaaattct tatcatgctt 600
aaagacccca acatgcagct ggaagtaatc gacctactca ccaaaacatg cagcaaggcg 660
cagaactatg aacagtagtg caagcggctg gtcctcaagt atattccact tattctggtg 720
aagggccaga aattccttga gacaacggat gtctgctctg tgatacatgc atgcaaagca 780
ggcacacaag catcaatgga agccatgcct ctgtctgcca tgttgtgaag gtgatgcga 839

<210> SEQ ID NO 17
<211> LENGTH: 179
<212> TYPE: PRT
<213> ORGANISM: maize

<400> SEQUENCE: 17

Met Cys Ser Val Ala Arg Leu Ala Phe Val Leu Ala Leu Ala Ile Ala
1 5 10 15

Ala Ser Ser Ile Glu Val Ala Glu Ser Arg Asp Phe Asn Ile Phe Ala
20 25 30

```
Gln Gly Ser Leu Pro Asp Ala Thr Lys Gly Ser Ser Gly Leu Ala Ala
        35                  40                  45

Thr Ser Gly Lys Leu Cys Gln Leu Cys Glu Gln Tyr Ser Ser Glu Ala
    50                  55                  60

Leu Leu Tyr Leu Thr Gln Asn Glu Thr Gln Thr Glu Ile Leu Ser Ile
65                  70                  75                  80

Leu His His Glu Cys Ala Ser Leu Ala Pro Leu Lys Gln Gln Cys Ile
                85                  90                  95

Thr Leu Val Asp Tyr Tyr Val Pro Leu Phe Phe Leu Glu Val Ser Met
            100                 105                 110

Val Thr Pro Glu Lys Phe Cys Glu Ser Met His Leu Cys Lys Lys Gly
        115                 120                 125

Met Lys Ile Ser Leu Pro Thr Arg Glu Gly Thr Cys Gly Leu Cys His
    130                 135                 140

His Val Val Val Glu Ile Leu Ile Met Leu Lys Asp Pro Asn Met Gln
145                 150                 155                 160

Leu Glu Val Ile Asp Leu Leu Thr Lys Thr Cys Ser Lys Ala Gln Asn
                165                 170                 175

Tyr Glu Gln


<210> SEQ ID NO 18
<211> LENGTH: 1961
<212> TYPE: DNA
<213> ORGANISM: maize

<400> SEQUENCE: 18

gcactcatag cacatctgag gttccctttc ttgaacttag ctcacctact gttcatagtt      60

ctgcgccttg ctgcatgttt tggtgagtag gtcgattact tccagctgca agcttgcagc     120

aaacaaagaa aggcattaca gtatgtacag agtacagagc agtacaacac agaagaatgt     180

tggtgacaga tagtgaaaat atggttatta cctgcatgtt ggggtcttta agcatgataa     240

gaatttcaac aacaacatgg tggcacaaac cacaagtacc ctcccgggtg ggtaggctaa     300

tcttcatccc cttcttgcag agatgcatcg actcgcagaa cttctcaggg gtaaccatgg     360

agacctccaa gaagaaaagg ggtacgtagt agtcaaccag cgtgatgcac tgcagcaggg     420

tgaatcatca acacaacatt taacacagct gaaaacgtgg taccaatgga aggatcacaa     480

gttacctata cctgctgttt gagaggggca aggctggcac attcatggtg tagaatgcta     540

agaatctcag tctgggtctc gttttgtgtg agatagagga gcgcctcgga tgagtactgc     600

tcgcataact gacacaactt tccactggtt gcagctagac cagacgatcc cttggttgca     660

tcaggcaagc tgccctgagc tgaattgaag acagaagaaa ggattggcca gaaatgcaaa     720

acttcagaaa aacttgagtt cctgtgagga atagcagcta agctgaagct acgccctcta     780

cattgagtag aactgatggc ttagacgtaa ttgctttctt taacatgtca ccggactaaa     840

tgaagatacg aacttgtcaa acaaagaagg aatttagata aactaattga aactatcacg     900

agatctccat cgaaaagaaa ctatcactag acctgataat tcactgctat ggatcaacat     960

tcaacaaaga ataaagagag taaggagcaa aaatcagtag attgaaagct taccaaagat    1020

attaaaatct ctgctctccg caacctcaat tgacgaggcg gctatggcca gtgcaagcac    1080

aaacgccagc ctcgctaccg agcacatcgt acctgcttac cactaccagt tggtcagttg    1140

acaggaacaa aactactgct tgaagaaaac tatcgcagtg aaatcagctg tggctgatgg    1200

acgcagaaaa gctggcttgc tcaaagcttc tccataaagc caaaaggtaa ccaaaaaaaa    1260
```

-continued

```
aagagaaagg aaatgtatcc tagggccctc tctctacgtc atgtaacgga tcagtagaag   1320

tttcagattc attcagcccg acgtaactga agaattcagt tcgcttcaag atgtagccat   1380

cagattcacg tatttggagt caagccaaga tagtaccaat tggtccgcat ccacattcca   1440

ggcaacagat tcacgagatt cagctcgctc cacgccagca gagctgctac tattctggca   1500

ccactccaaa tacgcctttg cagcagatta gcaaagcatt ttacgctcgc ttttgcgctt   1560

tattttgccc ctcgtttcct ttccaggtag cttccggttc cgaagaatcg gaggtccttg   1620

gattcaggga caaggggtcg aactgggcag caaatcaaga accgagggga gacggtagta   1680

cagagagccc aggagaagct aacatatgaa tggggaatta aagacgcatc tcacctggtt   1740

gactccgccg cccctgttct cggaattgga atgggagaga ggaaggccgg tatctgcatc   1800

ttggactctt ccgggagcac tttgttttct taaagcttcg tgttacatta agaagatgca   1860

tgagcatgta gaacagtgtg tgtggccgtg tgtgtgagaa cctgagatat ttttgcttct   1920

ttggtggcca agatgtgtta gaaaggcata atcttttctt a                        1961


<210> SEQ ID NO 19
<211> LENGTH: 589
<212> TYPE: DNA
<213> ORGANISM: maize

<400> SEQUENCE: 19

cgactggagc acgaggacac tgacatggac tgaaggagta gaaatatagc cagaactctt     60

gcatcctggt gatggtaaac tgccgtgcca gtataaacgc gaaggcaggt cacacatact    120

cacaagtccg tcccatctca ggtcatccat ccatccatcc ctgcagcaat ggcgtctgca    180

gtgaccagca gcgacaagga gcaggccgtc cctaccatcg acgctgacga agcgcacgcg    240

ctgctgagct ccggccatgg ctacgtggat gtcaggatgc ggggggactt ccacaaggcg    300

catgcgcccg gtgctcggaa cgttccctac tacctgtccg tcacgccgca agggaaggag    360

aagaacccac actttgtaga ggaagtggct gccttctgtg ggaaggatga tgtcttcatt    420

gtgggttgca acacggggaa cagatccagg ttcgcgacgg cagaccttct gaacgcgggg    480

ttcaagaacg tgaggaacct gcaaggtggt taccgctcct ttcagcagcg agctcaacag    540

cagtagacat cacgtcctga aggtatgcca gggatgctgc agttgaacg                589


<210> SEQ ID NO 20
<211> LENGTH: 125
<212> TYPE: PRT
<213> ORGANISM: maize

<400> SEQUENCE: 20

Met Ala Ser Ala Val Thr Ser Ser Asp Lys Glu Gln Ala Val Pro Thr
1               5                   10                  15

Ile Asp Ala Asp Glu Ala His Ala Leu Leu Ser Ser Gly His Gly Tyr
            20                  25                  30

Val Asp Val Arg Met Arg Gly Asp Phe His Lys Ala His Ala Pro Gly
        35                  40                  45

Ala Arg Asn Val Pro Tyr Tyr Leu Ser Val Thr Pro Gln Gly Lys Glu
    50                  55                  60

Lys Asn Pro His Phe Val Glu Glu Val Ala Ala Phe Cys Gly Lys Asp
65                  70                  75                  80

Asp Val Phe Ile Val Gly Cys Asn Thr Gly Asn Arg Ser Arg Phe Ala
                85                  90                  95

Thr Ala Asp Leu Leu Asn Ala Gly Phe Lys Asn Val Arg Asn Leu Gln
```

-continued

```
            100                 105                 110

Gly Gly Tyr Arg Ser Phe Gln Gln Arg Ala Gln Gln Gln
        115                 120                 125
```

```
<210> SEQ ID NO 21
<211> LENGTH: 2277
<212> TYPE: DNA
<213> ORGANISM: maize

<400> SEQUENCE: 21

cgcactaaga aggcagggaa ttgtgtggca aatataggta catgctacac gtgtgatatt     60
tcccgatttg tcaatctggg acatgaagtt aacatcgcaa attataatgt tacaggaacc    120
aggtatggtg ctagcttgcg taagcaaatc aagaagatgg aggtatctca gcattccaag    180
tacttttgcg agttctgtgg gaaggtacat ttctgttagt taccctgttt ctgcatccaa    240
gttttctaat ctttgatcta ttgaactgcg agctgtcttt atgttgtact cgttatcatc    300
accactgctg ttatgaaatg taggctgcag tcagattgat tttgagcaca tgaaatcaat    360
tagttttcga tatatctgtt tgtcacaagc acatgaaatc aattagtctt cgatatatct    420
gtttgtcaca tttgaatgat ttataagatg tctgggcatg tccatcaatg tgtttctaag    480
atacatttga agacagacag catttgttcc gaatccaacc tttgctgtgc tgtgtttcca    540
gtttgctgtg aagaggaaag cagttggaat ttgggggtgc aaggactgtg ggaaggtgaa    600
ggctggtggt gcttacacca tgaagtaagt aattcttcgc ctgtccgaaa accacaattt    660
gttagccacg gctaaattct gttaatgtgt ttgcagcact gctagtgcgg tcaccgtcag    720
gagcacgatc cgccgcctga gggagcagac tgaagcatga tatagctctt tatattattg    780
gggtttcctg tagttgctct tgtcaggcat gttgtggggg ccttatctag tggaaatgtg    840
gaatcactgt actggctgtt ttgccgagac aatgctcctt atatttggtt tatgctctag    900
gatctcaaag ttgtgttaag atttgccctt ggttaccgtt ctgaatctga caagtgatat    960
ttcatcctat gccatcttga cgtcgaattt ggttgtggtt ttctatgcgc ttggctgtgt   1020
caatggtttg ctattctgtt cttgaaattc tacagatact gctgcgtctc tgctggttga   1080
gtctggttta gatagcaacc agtccttatt attggtcttt caagttcaag tcaactaaaa   1140
tgcgacaaat aaaaaaaaga atggagggag tatataactg ttcaagtcaa ccaatcctta   1200
ttacgcctgc acttgtgtcc aaaaagaaat gccccggagc tattattggt ctgttgccag   1260
ataagcagtg acgacgcagc atcgaaggtc agagacgact tttttgcgag aacgagcatc   1320
aagctgacgg aatggagcat tattccgata aaaaaaaggt atagccagaa ctcttgcatc   1380
ctggtgatgg taaactgccg tgccagtata aacgcgaagg caggtcacac atactcacaa   1440
gtccgtccca tctcaggtca tccatccatc catccctgca gcaatggcgt ctgcagtgac   1500
cagcaggtaa acatagcttc tgagtgcatc tgatgttgct tacagtaaca ttacatgcat   1560
agagcagaag atcggatgca tctggattaa ccagagtcag tcttgtcttg gtgtgcactg   1620
cagcgacaag gagcaggccg tccctaccat cgacgctgac gaagcgcacg cgctgctgag   1680
ctccggccat ggctacgtgg atgtcaggtg cgtagagctc agccagtcag ggacgcgcct   1740
atgcgtgtgc tggagcttcc agacgaactg acgctgacgg ggacgaggtg gttctccttc   1800
gtgcaggatg cggggggact tccacaaggc gcatgcgccc ggtgctcgga acgttcccta   1860
ctacctgtcc gtcacgccgc aaggtcagtt tcttgctcgc tggcgttggc gctggcactg   1920
gcattggggt tattgatttg agctgcctct gtccccgtgt agggaaggag aagaacccac   1980
```

-continued

```
actttgtaga ggaagtggct gccttctgtg ggaaggatga tgtcttcatt gtggtagcta   2040

ttcactcata taaataaata aataaatgta ctagtactct ataaatagat agatacgcct   2100

gtaatcaagg agttgtcgtg tagggttgca acacggggaa cagatccagg ttcgcgacgg   2160

cagaccttct gaacgcggta aacacagccc atccgagctt tagcatcaat ccagttagct   2220

gtatgtgtgt gtgtgtgtgt gtgtgtttaa ctgagggtca cactagtctg ctcgcat      2277


<210> SEQ ID NO 22
<211> LENGTH: 897
<212> TYPE: DNA
<213> ORGANISM: maize

<400> SEQUENCE: 22

aagatagctg caaaacaagc gagttactta caaccaaaca gaagggtaga aaccacctga     60

agccatgtgc attgctgcat ggatttggca ggctcaccct gtgcaccaac tcctcctgct    120

tctcaacaga gatgagttcc acagcaggcc tacaaaagca gtaggatggt ggggtgaagg    180

ctcaaagaag atccttggtg gcagggatgt gcttggtgga ggaacatgga tggggtgcac    240

caaggatgga aggcttgcct tcctgaccaa tgtgcttgaa ccagatgcca tgcccggtgc    300

acggactagg ggagatctgc ctctcaaatt cctgcagagc aacaagagcc cactcgaagt    360

tgcaactgaa gtggcagaag aagctgatga atacaatggc ttcaacctca tactagctga    420

tctaacaaca aatatcatgg tttatgtgtc aaaccggcct aagggtcagc ctgcaacaat    480

tcaactcgtg tcaccaggac tccatgtgct gtccaatgca aggctagata gcccttggca    540

gaaggcaatt ctcctcggta aaaacttcag ggagcttctt agggagcatg gtgctgatga    600

ggttgaagtg aaggatatag ttgagaggct aatgactgac accacaaagg ctgacaaaga    660

tagactgcca aacactggtt gtgatcccaa ctgggagcat ggtctgagct ccatcttcat    720

tgaggtgcaa actgaccaag ggccctatgg gacacggagc acagccgttt tatcagtgaa    780

ctatgatggc gaagctagct tgtacgagaa gtatcttgag agtggtatat ggaaggatca    840

cacagtgagt taccagatag agtagtaggc attgcacagg aaaagttggc gacctca       897


<210> SEQ ID NO 23
<211> LENGTH: 266
<212> TYPE: PRT
<213> ORGANISM: maize

<400> SEQUENCE: 23

Met Cys Ile Ala Ala Trp Ile Trp Gln Ala His Pro Val His Gln Leu
1               5                   10                  15

Leu Leu Leu Leu Asn Arg Asp Glu Phe His Ser Arg Pro Thr Lys Ala
            20                  25                  30

Val Gly Trp Trp Gly Glu Gly Ser Lys Lys Ile Leu Gly Gly Arg Asp
        35                  40                  45

Val Leu Gly Gly Gly Thr Trp Met Gly Cys Thr Lys Asp Gly Arg Leu
    50                  55                  60

Ala Phe Leu Thr Asn Val Leu Glu Pro Asp Ala Met Pro Gly Ala Arg
65                  70                  75                  80

Thr Arg Gly Asp Leu Pro Leu Lys Phe Leu Gln Ser Asn Lys Ser Pro
                85                  90                  95

Leu Glu Val Ala Thr Glu Val Ala Glu Glu Ala Asp Glu Tyr Asn Gly
            100                 105                 110

Phe Asn Leu Ile Leu Ala Asp Leu Thr Thr Asn Ile Met Val Tyr Val
        115                 120                 125
```

-continued

```
Ser Asn Arg Pro Lys Gly Gln Pro Ala Thr Ile Gln Leu Val Ser Pro
    130                 135                 140

Gly Leu His Val Leu Ser Asn Ala Arg Leu Asp Ser Pro Trp Gln Lys
145                 150                 155                 160

Ala Ile Leu Leu Gly Lys Asn Phe Arg Glu Leu Leu Arg Glu His Gly
                165                 170                 175

Ala Asp Glu Val Glu Val Lys Asp Ile Val Glu Arg Leu Met Thr Asp
            180                 185                 190

Thr Thr Lys Ala Asp Lys Asp Arg Leu Pro Asn Thr Gly Cys Asp Pro
        195                 200                 205

Asn Trp Glu His Gly Leu Ser Ser Ile Phe Ile Glu Val Gln Thr Asp
    210                 215                 220

Gln Gly Pro Tyr Gly Thr Arg Ser Thr Ala Val Leu Ser Val Asn Tyr
225                 230                 235                 240

Asp Gly Glu Ala Ser Leu Tyr Glu Lys Tyr Leu Glu Ser Gly Ile Trp
                245                 250                 255

Lys Asp His Thr Val Ser Tyr Gln Ile Glu
            260                 265


<210> SEQ ID NO 24
<211> LENGTH: 1351
<212> TYPE: DNA
<213> ORGANISM: maize

<400> SEQUENCE: 24

cgactggagc acgaggacac tgacatggac tgaaggagta gaaaatcagc cgcagtcgcg     60

tcgcgtcgcg tcgcgtccag tccaatcctc ggagcctcac acgggcggac gagcgggagc    120

ttctcccaat ctcccctgcc ctgccctgcc ctgccgccgc gcttagcttc gcatcttccc    180

ctcctcctcc tcctccttcc tcggccaagc gaggagcgag gcgcgggcgc gagcgcgtcg    240

ttgagatgga ttcggaggcg gtgcagcacg gccttctccc tctgtctgcc tgtcctccta    300

ccgccaacag ctgcgcgcat tacagccgtg ggtgcagcgt cgtggcgccc tgctgcggcc    360

aggccttcgg ctgccgccat tgccacaacg acgccaagaa ctcgctggag gtcgacccgc    420

gcgaccggca cgagatcccc cgccacgaaa taaagaaggt gatctgttct ctctgctcca    480

aggaacagga cgtgcaacag aactgctcca gctgtggggc ctgcatgggc aagtacttct    540

gtaaagtatg caagttcttc gatgatgatg cctcaaaggg ccagtaccac tgtgacggat    600

gtggaatatg tagaaccggc ggcgtggaga actttttcca ctgtgataaa tgtgggtgtt    660

gctacagcaa tgtcttgaag gattcccacc actgcgtcga aagagcaatg catcacaact    720

gccccgtctg ctttgagtat ctgttcgact ccacgaagga catcagcgtg ctgcaatgtg    780

ggcataccat ccatttggag tgcatgaacg agatgagagc acaccatcac ttctcatgcc    840

cagtgtgctc gaggtccgcc tgcgacatgt cggccacatg gcggaagctc gacgaggagg    900

tcgcggccac gccgatgcct gacatctacc agaagcacat ggtgtggatc ctgtgcaacg    960

actgcagcgc gacctcgagc gtgcggttcc acgtgctggg gcacaagtgc cccgcgtgca   1020

gctcgtacaa cacccgggag acgagggctg cgtgccccag gatctgaggc gaaccagagg   1080

ccatgtcaca aaatgccagg gagatgccgt ccaacgacca tctgtctgca ggacgttgct   1140

gcgcttaagg ttaaaggcta gcgcgagacc aggcctggta gtccagtctt gagtttggtg   1200

ctggagcatt tgtaatgttc cggtaaaatg taatgcgtcc atgagtgctg tccaggcagt   1260

aagcacacct gtggatcggg gccggcgcaa ggtccctagg caagctgcag gattagtggg   1320
```

gctattcatg tttagggcgc gaatgcaacg a 1351

<210> SEQ ID NO 25
<211> LENGTH: 273
<212> TYPE: PRT
<213> ORGANISM: maize

<400> SEQUENCE: 25

Met Asp Ser Glu Ala Val Gln His Gly Leu Leu Pro Leu Ser Ala Cys
1 5 10 15

Pro Pro Thr Ala Asn Ser Cys Ala His Tyr Ser Arg Gly Cys Ser Val
20 25 30

Val Ala Pro Cys Cys Gly Gln Ala Phe Gly Cys Arg His Cys His Asn
35 40 45

Asp Ala Lys Asn Ser Leu Glu Val Asp Pro Arg Asp Arg His Glu Ile
50 55 60

Pro Arg His Glu Ile Lys Lys Val Ile Cys Ser Leu Cys Ser Lys Glu
65 70 75 80

Gln Asp Val Gln Gln Asn Cys Ser Ser Cys Gly Ala Cys Met Gly Lys
85 90 95

Tyr Phe Cys Lys Val Cys Lys Phe Phe Asp Asp Asp Ala Ser Lys Gly
100 105 110

Gln Tyr His Cys Asp Gly Cys Gly Ile Cys Arg Thr Gly Gly Val Glu
115 120 125

Asn Phe Phe His Cys Asp Lys Cys Gly Cys Cys Tyr Ser Asn Val Leu
130 135 140

Lys Asp Ser His His Cys Val Glu Arg Ala Met His His Asn Cys Pro
145 150 155 160

Val Cys Phe Glu Tyr Leu Phe Asp Ser Thr Lys Asp Ile Ser Val Leu
165 170 175

Gln Cys Gly His Thr Ile His Leu Glu Cys Met Asn Glu Met Arg Ala
180 185 190

His His His Phe Ser Cys Pro Val Cys Ser Arg Ser Ala Cys Asp Met
195 200 205

Ser Ala Thr Trp Arg Lys Leu Asp Glu Glu Val Ala Ala Thr Pro Met
210 215 220

Pro Asp Ile Tyr Gln Lys His Met Val Trp Ile Leu Cys Asn Asp Cys
225 230 235 240

Ser Ala Thr Ser Ser Val Arg Phe His Val Leu Gly His Lys Cys Pro
245 250 255

Ala Cys Ser Ser Tyr Asn Thr Arg Glu Thr Arg Ala Ala Cys Pro Arg
260 265 270

Ile

<210> SEQ ID NO 26
<211> LENGTH: 7106
<212> TYPE: DNA
<213> ORGANISM: maize

<400> SEQUENCE: 26
ccttacaggt tatcacttac cgcctccgtt ttcgaatatt tatcgttcgc tagttaatct 60
taatttaaac ttaaatgagg caaataaacg tttaaactat tctcttgatc gtgtgtctga 120
ttgtcttgtt gtttaaaatg cctcctagat cgatcgtcgt agtgcaggtt gttttagaca 180
aagttgaact gcgatcagac cgagaccgga caaccattga gcagttattt tcctattcat 240

```
cgtggactaa ctggaagata ttttctgagc tccaaaaaat atccaaagga agggagaacg    300
tgaaggacga ggtcggaccg gacacgcctc ccctcgctaa tcattgaggc ggaggcggcg    360
gaggcgattt tgggaacact cgcaggtaga ttttgcgtga acttggacga gggtcatttt    420
cgctttggat gaatccacga ggtggtgtca ctgcacgcgc acggggccct caaaccgttt    480
gaaaaccaaa ccgaaggcaa caaaacgaga ctctcatctc atctgactct acggccagct    540
caagtgatct gctgctggtg gccgacctgg cggcgtgatc tcgctcccgt gcccgtctcc    600
tccatccgac gcgtacatgg cccgccatcc tcatccatcc gccctccaga ggaccagtcc    660
agaccaataa taaaagggaa ggtcgacgac gggctcgctc caatccggcg aaccgcgtcc    720
ccgtcagcct gtcatcccgt gggcgcgcgg ctgtcgacct gcgcatcagc ttctatgatt    780
agccaggagc aataatttat tactcctatt tgccaggcga cgttcgtcca attcgacccg    840
gcaggcagca ggcagcagct gtgctcctgt gggtgggtgg gtcatgggtg accacatgca    900
tcgatggagc cagggccgcc gtgtgcgcag ccaactctac ctatccccgc ccccgggatg    960
ggcgatggca actatcctat cgcaacaata tcctggggtg ggggctataa aacggagcgg   1020
cccgcgtggg gcgcgcctcc atcagccgca gtcgcgtcgc gtcgcgtcgc gtccagtcca   1080
atcctcggag cctcacacgg gcggacgagc gggagcttct cccaatctcc cctgccctgc   1140
cctgccctgc cgccgcgctt agcttcgcat cttcccctcc tcctcctcct ccttcctcgg   1200
ccaagcgagg agcgaggcgc gggcgcgagc gcgtcgttga gatggattcg gaggcggtgc   1260
agcacgggta agcaagcaaa gcaatccatg gatcgatcca ggacacaggg aggagctagg   1320
aagaggaaca atctcatgat ctcattcatc tgacacagcc ttctccctct gtctgcctgt   1380
cctcctaccg ccaacagctg cgcgcattac agccgtgggt gcagcgtcgt ggcgccctgc   1440
tgcggccagg ccttcggctg ccgccattgc cacaacgacg ccaaggttcg gtggtttccc   1500
tccttccgtt ttcgcttcgg ctccggttca gcagatgttc tgaaacaacc ctgtcccgtg   1560
ccccggcaga actcgctgga ggtcgacccg cgcgaccggc acgagatccc ccgccacgaa   1620
ataaagaagg tcagcgttcc ctccctctgc tcaaagagca atctcctgcc tgtttcaacc   1680
attgcctatc tcgtgttcgt ctttgttatt accgtgagca aagaaaggaa gaaacaaaca   1740
agagcgccgc cttctctctt ctccttctcc atgtaatgga gcatttgttc cgccgcgtag   1800
tcgagtgcaa gcagcggttt tcctcttttg gaaacccacc cccacgcacg gttccgttcc   1860
aatctcgccc ttccaattga ccaacacaaa cctttcctaa gatttcttgt cctccttacc   1920
cttctacaga caagtacgaa acgcaatcgc acaaggttat actactacta gcttttagtg   1980
ttctagcgac cttagatttt tttttttggt taggcatccc tgatttttct cacacttaaa   2040
agcttcttca gataaggcca tatcagctca gctcagtgct ctgggagccg ttctgcactt   2100
cacttgcgtg tcactaaaaa cttgactgct ttccgcgatg tgctccgcac caagtggccg   2160
gcactgcgtg gtccacagga tttttcaaga gaaagccggg gtcacgggtg ccacttgaag   2220
ccaaggacag gcgtctggga ttggagaata tatgagaaag ggataccgtc agaggcacat   2280
ctcaccgtca aactgaacag ggtctaactg cttccagctg atttgattga gtttgagtgc   2340
tgcatagttg aggacctgga tatagtgacg tgtcctgaca ggtgtctttg gacctattag   2400
cagtgaatct gacgtcgatc ggctaaagca atcatgttcg attcttatcc tttttttttt   2460
gagagtatat gcctgattcg ataaacgttc ctatcctgtt tcctgatgat gcatatatgt   2520
tgtttcgatt catatagaat cataccatcc atctattttg tttaaaaaaa aaatttctgg   2580
```

-continued

```
gtggccatgg gcacagcatg cctgttctta agataacgat tccagtaact gttcccttct   2640
gtcactgaac tcatatgaat cgagacttaa ctggagctgt tgcgcaggtg atctgttctc   2700
tctgctccaa ggaacaggac gtaagttgtc taccaaaacg tactcctaca acagtttttc   2760
aggagcacgc atcttttggc tgtactacta ctgctaactg catggaaact gctcattccc   2820
atcggcaggt gcaacagaac tgctccagct gtggggcctg catgggcaag tacttctgta   2880
aagtatgcaa gttcttcgat gatgatgtaa gcgtactcga atcccagacg atgaacaaag   2940
aaactgaact cgatgcgttg tttactgcgt ttcttttttc ccccttcttc ttcacgtaca   3000
tactgtactg ctcttggtcc aggtctcaaa gggccagtac cactgtgacg gatgtggaat   3060
atgtaggtaa gcaccaccac gctgatggct acgtctaaag acttgacgcg cagaagtgta   3120
aaacttctgt cagccgttca aaactgataa attcgggttc ctcgtcttct tgttgtttat   3180
gcagaaccgg cggcgtggag aactttttcc actgtgataa atgtggtgag tttctgcgcg   3240
gacttctttc tgctaagatt ctgtaaccat gctatgcagc aaagatttca ctcgcgccct   3300
tattggtgtc cttgttgccg tccgacaggg tgttgctaca gcaatgtctt gaaggattcc   3360
caccactgcg tcgaaagagc aatgcatcac aactgccccg tctgctttga ggtgagagac   3420
ctccgtttca acggaacatt cactctgaat gttccaatct cttgatattg agaaggtttc   3480
cctctgtttt ttttcacagt atctgttcga ctccacgaag gacatcagcg tgctgcaatg   3540
tgggcatacc atccatttgg agtgcatgaa cgagatgaga gcacaccatc agtaagcata   3600
tataccgttc tcttcggagc tgagaaacgg tgccacctca caacatcctc ttttagtcgc   3660
agtgacctta cagtctcagc cctgtttggt ctttggcagc ttctcatgcc cagtgtgctc   3720
gaggtccgcc tgcgacatgt cggccacatg gcggaagctc gacgaggagg tcgcggccac   3780
gccgatgcct gacatctacc agaagcacat ggtaagaagc cgaccgccca ctcgttcgtc   3840
gtcccgttac atcttttcca cagccatggc tcgctgtttg acgagctctg aacctgtccg   3900
gggtgccgat tgctggaact gaacggcaaa tgaacgctgt ggtgtgagtg caggtgtgga   3960
tcctgtgcaa cgactgcagc gcgacctcga gcgtgcggtt ccacgtgctg gggcacaagt   4020
gccccgcgtg cagctcgtac aacacccggg agacgagggc tgcgtgcccc aggatctgag   4080
gcgaaccaga ggccatgtca caaaatgcca gggagatgcc gtccaacgat catctgtctg   4140
caggacgttg ctgcgcttaa ggttaaaggc tagcgcgaga ccaggcctgg tagtccagtc   4200
ttgagtttgg tgctggagca tttgtaatgt tccggtaaaa tgtaatgcgt ccatgagtgc   4260
tgtccaggca gtaagcacac ctgtggatcg gggccggcgc aaggtcccta ggcaagctgc   4320
aggattagtg gggctattca tgtttagggc gcgaatgcaa cgaaattacc cgtgggccgt   4380
gggctcggta tgtaacagaa ccgattattt ctattacaat aataacatgc agttctattg   4440
ggccgagcct aatcaggcac cacgaatgtg aataattgca catggcgcat atatggcggg   4500
cagtagatac atataaaatg gagaaaatcc gtttattgcc atcaaaactt atactgatca   4560
ctacaatacc atctaaaatg atgtgctccc ttcaaaacca ttggtttata ttttctatcc   4620
tttcattgcc attgccgtta cataatggcg catgtggcat atatgggcgg cgtatgtagg   4680
ttcaggatgg tcacacgaca tatgacgaga ctacagagac atggtcaaga gaagttcagt   4740
ggattgtgac attctgatct aagacttctt aaaattggag ttaataagat cgataatact   4800
cgtaccaata atgcacatct tgctttttag aagcctgttt tgaaataacc ccaggattaa   4860
gcatgtttgg cccaaagaaa tttttgtgat ggtggtcgac cgagaagttt tcttgactgc   4920
atgccagtga ggacaaaaaa acacatatga aagaatcgtg ttggtctgtg agaatagatc   4980
```

-continued

```
aggaagtttt ctcgactgcg cgaccatgga tggttggggt gtttcatcaa ggatccgctt   5040
taaacacata cctttttgcc ttggtgatgg ataaggacat accggacata aaggggataa   5100
cccttggtgt gtgtttttt gcagacaatg taatgctagt tgatgaaagt cgggcatgag    5160
taaatggaaa actagagttg tggcaagaaa ctttataatc aaaaggtttt agacttagta   5220
gaactaaaat agaatatatt ggatgcgatt tcagcactac atatgaggaa tgagatctta   5280
gtttagaagg tctaggaagg acacctttag atatttagta tcagcctata gagagaccgg   5340
gatattaatg aagatgctag ccataaaatc aaagtagagt cagtgaagtg gagtcaagca   5400
tctggcattt tatatgacaa agtgggaatt gcaaaagcta aaaagaaagt tttaggacaa   5460
cgattagacc ttctatatta tatggaacat aattttagcc tacaaaaaga tgatatgttt   5520
agcagataaa tgttgcggta atacatatgt tacgttggat ttgtgaacat acaaaaaggg   5580
atcgagttta gaatgatgat atacatgata gactaggggt agcaccagtc gatcgatatg   5640
gtttgaatat atccaacgga gacctataga ggtgtcaata tgtcttagga cctgtttgaa   5700
agcatccagt ttttaagaaa ttggtttata gaaattaaag tggttccaaa catacaagtt   5760
tatgccccag tttatataaa ctggattatc aatttcttaa aaaccaagaa gctagtcttt   5820
gctagctaaa accaactttt gcttgtttaa ttacataatg cccttgttgg ttgcatggaa   5880
tttacatcta ttgtcgtcgc ttttaagata gaggaagggt atgttagtaa ttgtgtatca   5940
aaaaatagaa aatttgtttc ttagaactaa gttccaaaca ccctcaccta actttttat    6000
aaactagttt ctataaactg gagatagaaa ttggttttta ataaaccggt atgctttcaa   6060
acaatacctt aggattctaa gatgtgatac caatgagaaa aggaagagga agactgaagt   6120
tggtatggga ggtgataata aaatgagtct tgaaaaaatg agatatatct aaagatttag   6180
ccttgaatag aaatgcatga aaataactat ccatatgttt gaaccttgac tttgagtttt   6240
gttgaatttt taactctagc ctacgccaat ttgtttggga ctaaaaggtt atgttgttgt   6300
tattgccgct ataaatggtg ttcaacactt tcttcaagat tatgatattt tgttttctac   6360
accaacaata ttactgttgg ggtctccttc tctgccgaag gtcctcagga tgaagaaact   6420
gtctttggtt catcttggta agatacgtca aaaggaccga atgccgaagc tgtgacagac   6480
atgcagggaa tatagcagag cttcgataag agttaaagct tcggcttaag atgattatga   6540
aggtcataca agaaaccaag ccaccaatga aaagacctgt ttatccttaa aatttgtatt   6600
agaacaatgt atagatatca gggtcataaa tgtacttttg cttgggcggc gtcccgtgcc   6660
tataaataga tgaactgtac ccccgtactg ttgacacttt cattgaaagt cattctcgca   6720
ctctctcctt caagcaagac gaaggtacta atgtaatata atgtttgtaa tggttcatta   6780
gaatgttatc caaactatgt cattactttg atatagaaaa taaagtgaat tcataagata   6840
ataccacatt gtgatattat ctccatgaga aatgaagatc cgctcttctt caccttcgcc   6900
caaaaaccat tatctttgag agaagataat tgaaaggaaa ttgggttaac catttcctat   6960
aactaatttt ggtgggtgat gatcaacaca aacccatgga ctaactagtt tgtctagaat   7020
tcatggatta caggtgcata aggttcaaca caaaccaaga aagaaatccg gttagggaca   7080
caattaaaaa tggagcaaag acttga                                        7106
```

<210> SEQ ID NO 27
<211> LENGTH: 645
<212> TYPE: DNA
<213> ORGANISM: maize

<400> SEQUENCE: 27

```
cgactggagc acgaggacac tgacatggac tgaaggagta gaaagctgct attttcttct     60

tacattgtcc actgcgctag ctagctcgca tctacctgga aagctgaaag ctagccagag    120

cgctagctag cttcgttcct cgtcgccgcg cgccggccag atgactgctc accagacttg    180

ctgcgatgat gccgttgccg ccggcactgc accggctgcc aggaggaggc gcctcaaatt    240

gacgaggccg tcggcctcgc tcttgatggc gaggaagcta aggaagaagg ctgccggcag    300

caaacgccca agggcggcag cgtcgaggaa gcgcgcgatg gcgatcagga ggaagatgga    360

agcgctgagg ctgctcgtgc cactctgcgg ccgagacaac ggctcggtga ccggtggggc    420

ggtcgaacga ctggacgagc tcctcatgca cgccgccggg tacatcctgc gcctccagat    480

gcaggtcaga gtgatgcagc ttatggtcca tgcactaaat gaccggcccg aggattaatc    540

ttcttcccaa gaccatgtga tcttccttct ttaatttctt cttcatcttc ttcgcgtgcc    600

tgtgttgcac gaggcagctg tgcgtcggtg tctgggtgca aatca                    645
```

<210> SEQ ID NO 28
<211> LENGTH: 125
<212> TYPE: PRT
<213> ORGANISM: maize

<400> SEQUENCE: 28

```
Met Thr Ala His Gln Thr Cys Cys Asp Asp Ala Val Ala Ala Gly Thr
1               5                   10                  15

Ala Pro Ala Ala Arg Arg Arg Arg Leu Lys Leu Thr Arg Pro Ser Ala
            20                  25                  30

Ser Leu Leu Met Ala Arg Lys Leu Arg Lys Lys Ala Ala Gly Ser Lys
        35                  40                  45

Arg Pro Arg Ala Ala Ala Ser Arg Lys Arg Ala Met Ala Ile Arg Arg
    50                  55                  60

Lys Met Glu Ala Leu Arg Leu Leu Val Pro Leu Cys Gly Arg Asp Asn
65                  70                  75                  80

Gly Ser Val Thr Gly Gly Ala Val Glu Arg Leu Asp Glu Leu Leu Met
                85                  90                  95

His Ala Ala Gly Tyr Ile Leu Arg Leu Gln Met Gln Val Arg Val Met
            100                 105                 110

Gln Leu Met Val His Ala Leu Asn Asp Arg Pro Glu Asp
        115                 120                 125
```

<210> SEQ ID NO 29
<211> LENGTH: 2433
<212> TYPE: DNA
<213> ORGANISM: maize

<400> SEQUENCE: 29

```
taaatctgac ctccaaaatg tctctaatga aagtgtctgc gagaaacagt attgctcgac     60

cgaggaagaa aggtatttat aacacaccca tcacaaatgg ttggcttaat taaccgcaag    120

tgcagaatag atttgcactg ttggttcact taataaaact gcaagtgaaa atatactttt    180

tctactatcg gttttgttaa gtgaacctac cgattttgca ctggtgatta tttaagccaa    240

cctcatgtga taatatgaat gatttgcacg tggttttatt aagcgaacta acaatgtaaa    300

tgtgtttcca atggtggttt ttaagtcggg accgtcattt tactttaact ggcgcgcacc    360

gtgctgtttt atacttgact gatgaacctt cgtggtgagt ggaagcggtg tggagcgagg    420

gctagctcat gcggccagcc ggcgacattt ctcttgttcc gatcccccgg ccggccaacc    480
```

```
actcaattaa gtaggtgatc gattggcatg catgcatgga tgcatatcag caaatgcata    540
tcatatgcct cgctagctgg ctagtatata tagtggatgt ggatcggatc atgtgacggc    600
cgggcggtgg ctgcattgca ttggccctgc atatatgcac ggtgacacaa caacggggcc    660
caaataaagg acacgtcgaa ggtgcgcgcc ccagtggcgt ccgacagcgc gttttgacga    720
ggaaaagagg gtgcgggcac gcgcgcacgc atatgctcgc ggcatgcagc ctcagtggcc    780
gatgacgagt ggcgtgtggt gtggccggcg gccggccggc cgggtgcctg cgtggtgcat    840
gttgcttgcc atgcctgcgt gaaatgagcc gtcagcgagc gagctgaggg cgggcatgtg    900
gctgcatgtg gccactagtt tggagaacat gcggcatatg ccccggacct tcctgggcgc    960
tcaagcaaac accgctctcg tgctcgctct cttgggaaat cgcagatgca tgctacccaa   1020
cgtgacctgg atctctttta cgtacgcaca ccctagcgtg ctgctctcct gtgtccccgc   1080
ctcctgctag ctgttcacaa tatccacgcg atttaacaaa cagatatgtg tgcatgctac   1140
tgcttgtttt cctattcaat atagtaatct gctttattta gagtaccgta cctgtgccgt   1200
cagtgccccc aaccccaacg taactacgca cgcacatggc atctaatcta tataagcatc   1260
agaccttgct cccttaatct cgcgctgcta ttttcttctt acattgtcca ctgcgctagc   1320
tagctcgcat ctacctggaa agctgaaagc tagccagagc gctagctagc ttcgttcctc   1380
gtcgccgcgc gccggccaga tgactgctca ccagacttgc tgcgatgatg ccgttgccgc   1440
cggcactgca ccggctgcca ggaggaggcg cctcaaattg acgaggccgt cggcctcgct   1500
cttgatggcg aggaagctaa ggaagaaggc tgccggcagc aaacgcccaa gggcggcagc   1560
gtcgaggaag cgcgcgatgg cgatcaggag gaagatggaa gcgctgaggc tgctcgtgcc   1620
actctgcggc cgagacaacg gctcggtgac cggtggggcg gtcgaacgac tggacgagct   1680
cctcatgcac gccgccgggt acatcctgcg cctccagatg caggtcagag tgatgcagct   1740
tatggtccat gcactaaatg accggcccga ggattaatct tcttcccaag accatgtgat   1800
cttccttctt taatttcttc ttcatcttct tcgcgtgcct gtgttgcacg aggcagctgt   1860
gcgtcggtgt ctgggtgcaa atcattggct gagtgtgtta ttggtgatat tatttgttcg   1920
tatatacaga atatatactc atgcatgcat actgtatgag atgatagagt aaatctagac   1980
atatatagtt caaggaaacc tacagccaac agttgtatgc atgtgagggg ggttccttgt   2040
ctgtatgtac gcaattgtct attgtgtgac ggttgaaatt gaaatttcgt caatcatcat   2100
ttcttcgtct agataacgtg tgtacaaacg gcgagtgttt aaatgaacta gagctaataa   2160
ttagtggcta aaattagctg gagacatcca aacaccctaa ctaataattt aactattagt   2220
tatttttagt aaattagtca atacttagct agctatttgt tagctagcta attctactag   2280
catttttag ctaactagct attagctcta gtacattcaa acacctttt agggactaat    2340
ttttagtctc tccattttat ttcattttag tcactaaatt accaaatacg aaaattaaag   2400
ctctatttta gtttccggta tttgacaatt tag                                2433
```

<210> SEQ ID NO 30
<211> LENGTH: 1146
<212> TYPE: DNA
<213> ORGANISM: maize

<400> SEQUENCE: 30

```
ggacactgac atggactgaa ggagtagaaa atccatccat tcccctcgcc aagccgccac     60
ggcctgactt tccctcccgc acacccgcga ccatacaggc aagtcaggca tacaccaaca    120
```

-continued

```
acgctcgtcg tgcacctcgc gcctcaggtc accccaccaa attcctcttg atacgccgaa    180

tttcttttgc taattctgct acctcctgtc gctaagccac catattcagt ctaacccctg    240

ctctgagctc acctgattgg cggctccgtt cggcctctgg gcctgggtgt accgactacc    300

gagggctctt tcgaaatgtc aattgggtcg agtttggtgg gctacgtgaa gcatggatga    360

atttcccggc tggaagcggg aggcggcagc agcatccggg gccggagcac ctgtcgccga    420

tgacgccgct cccgctggcg cggtaggggt cggtctactc gctcacgttc gacgagttcc    480

agagctcgct cggtggggcc accaaggact tcggatccat gaacatggac gagctcctcc    540

gcaacatctg gtcggcggag gagacacaca gcgtcacagc tgcggaccat gccgcgcggg    600

cgccgtacgt ccagtgccag ggctcgctca ccctcccctg cacgctcagc cagaagaccg    660

tcgacgaggt ctagcgtgac ctcgtgtgca acggtggagg accctccgac gaggctgtgg    720

cgccgcccca ccggcccaac ggcagccgac gctcggggag atcatgctgg aggagttcct    780

cgtccgcgcc ggcgtggtga gggaggacat gatggcggcg gcgcccgtac caccagcgcc    840

gggttgccca ccacctcatc tgcaaccgcc aatgctgttt ccacatggca atgtgtttgc    900

tcccttagtg cctccgctcc aattcgggaa tgggtttgtg tcgggggctc tcagtcagca    960

gcagggaggt gttcttgagg ccccggcggt atcgccgcgg ccggtgacgg caagcgggtt   1020

cgggaagatg gaaggagacg acttgtcgca tctgtcgcca tcaccggtgt cgtacgtttt   1080

tttgtgctgg tttgaggggga aggaagccac cagctgtgga caaggtggtt gagaggaggc   1140

aacgcc                                                              1146
```

<210> SEQ ID NO 31
<211> LENGTH: 108
<212> TYPE: PRT
<213> ORGANISM: maize

<400> SEQUENCE: 31

```
Met Asp Glu Phe Pro Gly Trp Lys Arg Glu Ala Ala Ala Ala Ser Gly
1               5                   10                  15

Ala Gly Ala Pro Val Ala Asp Asp Ala Ala Pro Ala Gly Ala Val Gly
            20                  25                  30

Val Gly Leu Leu Ala His Val Arg Arg Val Pro Glu Leu Ala Arg Trp
        35                  40                  45

Gly His Gln Gly Leu Arg Ile His Glu His Gly Arg Ala Pro Pro Gln
    50                  55                  60

His Leu Val Gly Gly Gly Asp Thr Gln Arg His Ser Cys Gly Pro Cys
65                  70                  75                  80

Arg Ala Gly Ala Val Arg Pro Val Pro Gly Leu Ala His Pro Pro Leu
                85                  90                  95

His Ala Gln Pro Glu Asp Arg Arg Arg Gly Leu Ala
            100                 105
```

<210> SEQ ID NO 32
<211> LENGTH: 122
<212> TYPE: PRT
<213> ORGANISM: maize

<400> SEQUENCE: 32

```
Met Leu Glu Glu Phe Leu Val Arg Ala Gly Val Val Arg Glu Asp Met
1               5                   10                  15

Met Ala Ala Ala Pro Val Pro Pro Ala Pro Gly Cys Pro Pro Pro His
            20                  25                  30
```

```
Leu Gln Pro Pro Met Leu Phe Pro His Gly Asn Val Phe Ala Pro Leu
        35                  40                  45

Val Pro Pro Leu Gln Phe Gly Asn Gly Phe Val Ser Gly Ala Leu Ser
    50                  55                  60

Gln Gln Gln Gly Gly Val Leu Glu Ala Pro Ala Val Ser Pro Arg Pro
65                  70                  75                  80

Val Thr Ala Ser Gly Phe Gly Lys Met Glu Gly Asp Asp Leu Ser His
                85                  90                  95

Leu Ser Pro Ser Pro Val Ser Tyr Val Phe Leu Cys Trp Phe Glu Gly
            100                 105                 110

Lys Glu Ala Thr Ser Cys Gly Gln Gly Gly
        115                 120


<210> SEQ ID NO 33
<211> LENGTH: 1376
<212> TYPE: DNA
<213> ORGANISM: maize

<400> SEQUENCE: 33

tagaatagcc agcatcgaca aattacttac aaatagaaac attacctgtt tcctcccacg     60

cgacctcgcg gccaactccc ggttcttgat catccggcgt tgcctcctct caaccacctt    120

ctccacagct ggtggcttcc ttcccctcaa accagcacaa aaaaacgtac gacaccggtg    180

atggcgacag atgcgacaag tcgtctcctt ccatcttccc gaacccgctt gccgtcaccg    240

gccgcggcga taccgccggg gcctcaagaa cacctccctg ctgctgactg agagcccccg    300

acacaaaccc attcccgaat tggagcggag gcactaaggg agcaaacaca ttgccatgtg    360

gaaacagcat tggcggttgc agatgaggtg gtgggcaacc cggcgctggt ggtacgggcg    420

ccgccgccat catgtcctcc ctcaccacgc cggcgcggac gaggaactcc tccagcatga    480

tctccccgag cgtcggctgc cgttgggccg gtggggcggc gccacagcct cgtcggaggg    540

tcctccaccg ttgcacacga ggtcacgcta gacctcgtcg acggtcttct ggctgagcgt    600

gcaggggagg gtgagcgagc cctggcactg gacgtacggc gcccgcgcgg catggtccgc    660

agctgtgacg ctgtgtgtct cctccgccga ccagatgttg cggaggagct cgtccatgtt    720

catggatccg aagtccttgg tggccccacc gagcgagctc tggaactcgt cgaacgtgag    780

cgagtagacc gacccctacc gcgccagcgg gagcggcgtc atcggcgaca ggtgctccgg    840

ccccggatgc tgctgccgcc tcccgcttcc agccgggaaa ttcatccatg cttcacgtag    900

cccaccaaac tcgacccaat tgacatttcg aaagagccct cggtagtcgg tacacccagg    960

cccagaggcc gaacggagcc gccaatcagg tgagctcaga gcaggggtta gactgaatat   1020

ggtggcttag cgacaggagg tagcagaatt agcaaaagaa attcggcgta tcaagaggaa   1080

tttggtgggg tgacctgagg cgcgaggtgc acgacgagcg ttgttggtgt atgcctgact   1140

tgcctgtatg gtcgcgggtg tgcgggaggg aaagtcaggc cgtggcggct tggcgagggg   1200

aatggatgga tatgtgtcgc caccaaggag tcgtgtgggg gagtttaaaa cgtcgccagg   1260

ctcgaggtcg cacatggtgt tgggtttggg tgcgtgctgg gtcataaaag ctgaaaggga   1320

attaggctta cacctatttc ctaaatgatt ttggtggttg aattgtccaa cacaaa       1376


<210> SEQ ID NO 34
<211> LENGTH: 686
<212> TYPE: DNA
<213> ORGANISM: maize

<400> SEQUENCE: 34
```

attcccgtct tacctagcgc tagggttagt acgcgtccac ggcgacgacc tctgcgcgga 60
gtgtgctccg attggctggc ctcctcgatc ctccttcccg cgaacgcacg cgcgcgcgag 120
ggagaggttg agacttgaga gatagacgaa agacgaaaca agggaaggag acgccgtgct 180
cgcctattgg ccgccgcctc cgctccttcg cgcccaatgg cttctgcagc atatcaatat 240
catgcagcat agcagtactc agacccttac tacgcaggcg ttgttgctcc ctatggaagt 300
caagatgtgt gtccgaggag cctgtctatg tgaacgccaa gcagtaccgc ggcattctaa 360
gacggcggca gtcacgtgcc aaggccgagc ttgagagaaa gcgctggtca agcaagaaag 420
ccgtatcttc acgagtcccc gtcatcagca cgcgatgacg aggagggcga gagggaacgg 480
tggacgcttc ctaaacacga agaagagtga ccgtgtccct cctgatgact tgatacagct 540
acgacgacac aacgaggctt gaagaggtag cggtctggct ggcatcctag agcagcggtt 600
tctgtccaca ggcacgtgca tctgagaccg gatccgtagc tccactccac agcatatgcg 660
cagcccatcc atctcgtgca cacttg 686

<210> SEQ ID NO 35
<211> LENGTH: 50
<212> TYPE: PRT
<213> ORGANISM: maize

<400> SEQUENCE: 35

Met Gln His Ser Ser Thr Gln Thr Leu Thr Thr Gln Ala Leu Leu Leu
1               5                   10                  15

Pro Met Glu Val Lys Met Cys Val Arg Gly Ala Cys Leu Cys Glu Arg
            20                  25                  30

Gln Ala Val Pro Arg His Ser Lys Thr Ala Ala Val Thr Cys Gln Gly
        35                  40                  45

Arg Ala
    50

<210> SEQ ID NO 36
<211> LENGTH: 922
<212> TYPE: DNA
<213> ORGANISM: maize

<400> SEQUENCE: 36
cgactggagc acgaggacac tgacatggac tgaaggagta gaaaaaaaac ccaaatcaaa 60
tttcgccttc gtcgtcgtct tatcgtctca gatttgactc catgtcggcg gcgctcgcgg 120
tgacggacga ggtggccctg ccgatccggg cggtggggga tctagcggcc gccgccgagg 180
tctcgcggga ggaggtcgcc gtcatcaccc agtgcgcggc gctcggtggg aagttgcctt 240
ttgaagatgc atcagttggt gcggttcttg cagtcattaa aaacgtggaa agcttgaggg 300
agcaattggt tgctgaaatc aggcgggtgc tgaaagctgg tggaagagta ttggtgcaga 360
gccctgcacc ctcatccagt cagaagccga acactgatat tgagcgcaag ttactgatgg 420
gtggatttgc tgaagtgcaa tcttctgctg caagctcgca ggatagcgtg caatctgtta 480
cagttaaggc aaagaaggct agctggagca tgggctcttc ttttcccctt aagaaaacaa 540
caaaagccct tcccaagatt caaattgacg acgactctga tctgattgat gaagacagtc 600
tcttgactga ggaggacctg aagaaaccac aacttccagt tgttggggac tgtgaggtgg 660
gggcagcaaa gaaagcatgc aagaactgta cttgtggcag ggctgaggcc gaggagaagg 720
ttgggaagct ggagctcact gcggagcaga tcaataaccc tcagtcagct tgtggcagtt 780

```
gtgggttggg tgatgccttc cgctgtggaa cctgtcccta cagaggtctt ccaccattca    840

agcctggcga gaaggtttcc ttgtctggca acttccttgc tgctgacata tgatggcatc    900

gccaacatcg gcaaaacaag ga                                              922
```

<210> SEQ ID NO 37
<211> LENGTH: 263
<212> TYPE: PRT
<213> ORGANISM: maize

<400> SEQUENCE: 37

```
Met Ser Ala Ala Leu Ala Val Thr Asp Glu Val Ala Leu Pro Ile Arg
1               5                   10                  15

Ala Val Gly Asp Leu Ala Ala Ala Ala Glu Val Ser Arg Glu Glu Val
            20                  25                  30

Ala Val Ile Thr Gln Cys Ala Ala Leu Gly Gly Lys Leu Pro Phe Glu
        35                  40                  45

Asp Ala Ser Val Gly Ala Val Leu Ala Val Ile Lys Asn Val Glu Ser
    50                  55                  60

Leu Arg Glu Gln Leu Val Ala Glu Ile Arg Arg Val Leu Lys Ala Gly
65                  70                  75                  80

Gly Arg Val Leu Val Gln Ser Pro Ala Pro Ser Ser Ser Gln Lys Pro
                85                  90                  95

Asn Thr Asp Ile Glu Arg Lys Leu Leu Met Gly Gly Phe Ala Glu Val
            100                 105                 110

Gln Ser Ser Ala Ala Ser Ser Gln Asp Ser Val Gln Ser Val Thr Val
        115                 120                 125

Lys Ala Lys Lys Ala Ser Trp Ser Met Gly Ser Ser Phe Pro Leu Lys
    130                 135                 140

Lys Thr Thr Lys Ala Leu Pro Lys Ile Gln Ile Asp Asp Asp Ser Asp
145                 150                 155                 160

Leu Ile Asp Glu Asp Ser Leu Leu Thr Glu Glu Asp Leu Lys Lys Pro
                165                 170                 175

Gln Leu Pro Val Val Gly Asp Cys Glu Val Gly Ala Ala Lys Lys Ala
            180                 185                 190

Cys Lys Asn Cys Thr Cys Gly Arg Ala Glu Ala Glu Glu Lys Val Gly
        195                 200                 205

Lys Leu Glu Leu Thr Ala Glu Gln Ile Asn Asn Pro Gln Ser Ala Cys
    210                 215                 220

Gly Ser Cys Gly Leu Gly Asp Ala Phe Arg Cys Gly Thr Cys Pro Tyr
225                 230                 235                 240

Arg Gly Leu Pro Pro Phe Lys Pro Gly Glu Lys Val Ser Leu Ser Gly
                245                 250                 255

Asn Phe Leu Ala Ala Asp Ile
            260
```

<210> SEQ ID NO 38
<211> LENGTH: 5083
<212> TYPE: DNA
<213> ORGANISM: maize

<400> SEQUENCE: 38

```
gctgtaccag ttgaggtact ccttgacgtc ctcgtacatg gtgggcgcca gcgggtgcca     60

gatgccggag tcgaggtaga gcacggggtc gtcgtacttg atgccggcgc ccctaagcac    120

cggcaagtag gatccggcga tcatcttgag gaagttctgg aggttgtccg ccgagccgcc    180
```

-continued

```
gagccagaac tggaggctga ggatgtacag ccaggcgtcc tgcgccttgt cggagggcag    240
gtacttgagc accttgggca gcgtgcgcac gagcttgagc atgctgtcgg cgaagttgct    300
ggagttggac ttgctgcgct tgaagagctg gaagaagggg ctcttggact gccccagctg    360
cgacatgctg aaggagccga gcttgttgag gcgcatgacc tcgggcatgg aggggaagac    420
aaggacggcg tccatgcggt cgcgctcctt ctcggccgcg gccttgacct tgagcgccag    480
ctcctcgacg aagatgaggg agccgatgaa gacgttgacg tcggcgaggt cggcgcggaa    540
ggtagcccac gacctcgaac gacgcggcgc ggcgcgggtc agcgttgagc tgctgcacgg    600
cggccgtgac ggacgactgg tactgcgcct ccagcacgac gtagacgacc ttgacccgag    660
gcaggccccg cgggtcggcc ggcaccacgc gccgcacctc gggcttggtc tgcgtgaaca    720
agccgttgcc gccggcgacc gcgcaccgga tggcgccggc gcgccgcggc tgctggcgac    780
ggctgctcag gaggaacgag tgcagcggca cgggcgccgc caggagctgc ttctgcgccg    840
cggcggcgaa tggggtggac actagcgacg acgacatggc gcctgctcac aggacggagc    900
cggcgggcgg agaaacgcgc gcctggacac tgacgcgacg ctcgagcgca gtaagtaaaa    960
aaaaatctac actagactac tagagtaagg cgcctgttct tggctcgtgg ctggacaatt   1020
gttcttggcg gccgccgtcc ctcggaaaca gagcagggaa aggagaagaa gcgagcaggg   1080
gagcgcggga ggcgggaaaa tgtataggtt gtccgtgtcc acgtccttcg tctcaattaa   1140
gaagaggcat ccaggctcac aaaatcaatc tgaaaacaca tgcactgatg cacacttgtg   1200
tttgtgtaga ggcgcttata tatcatccaa aagacaagtc actcacacgc aaattcgcat   1260
tggctaacag aagctatttg gaatgcagtt cagtcgacta acaacgtagg taccccccgtc  1320
tccttgtttt gccgatgttg gcgatgccat catatgtcag cagcaaggaa gttgccagac   1380
aaggaaacct gccaatcgga gaagcagcag cagtgaacgt tcaagatcca gagtacaatc   1440
gacagacata ttttgatctc ctcgagaatt ctatcagggg aggagacgag tagaactgtt   1500
ttaccttctc gccaggcttg aatggtggaa gacctctgta gggacaggtt ccacagcgga   1560
aggcatcacc caacccacac tgcaaagaaa aatcaaggat catttacaga tatcaccaga   1620
cgtgataggt aacctagtcc gagtgaacgt atgaaatttc acgagggggc acaagtgcca   1680
cctgtaagca atacttacac tgccacaagc tgactgaggg ttattgatct gctccgcagt   1740
gagctccagc ttcccaacct tctcctcggc ctcagccctg ccacaagtac agttcttgca   1800
tgctttcttt gctgccccca cctcacagtc cccaactggt gaaaacatca gtgaaaacat   1860
cacttaactg tttaggatcc aaacctaaac tggctattgc ttacggagtt gaactaagtt   1920
gacgggtttt gttgctctac caactggaag ttgtggtttc ttcaggtcct cctcagtcaa   1980
gagactgtct tcatcaatca gatcagagtc gtcgtcaatt tgaatcttgg gaagggcttt   2040
tgttgttttc ttaaggggaa aagaagagcc catgctccag ctagccttct ttgccttaac   2100
ctacaagtgg ttcaaattag cacaaaaact aaagcctgca cagcaaaact aacatactat   2160
aacacatgat cttagaccac tcactgtaac agattgcacg ctatcctgcg agcttgcagc   2220
agaagattgc acttcagcaa atccacccat cagtaacttg cgctcaatat cagtgttcgg   2280
ctaacggaga caatcataaa aaaattaaga actttaaatc gacattgcaa gagaaacgag   2340
acaacaaaga cagattctga taagttaata ccttctgact ggatgagggt gcagggctct   2400
gcaccaatac tcttccacca gctttcagca cccgcctgat ttcagcaacc aattgctccc   2460
tcaagctttc cacgttttta atgactgcaa gaaccgcacc aactgatgca tcttcaaaag   2520
gcaacttccc acctgatgca tggcagaaca atagtttggt cacggttttg tgataacaca   2580
```

-continued

```
cacacacaca cacacacaca cacacacaca cacacacaca cacacacggc atagcactag   2640
caaagcataa cacaaattaa aaatcgaaca ttattgttta atagaggctc ccaaaatcag   2700
gaatgctagc acttggctta ttcataaaca cacacatcca taatcaggaa gcatacatta   2760
ctgaaccatt aaatttaata ataaaaattc agatgttgaa tccatggctg aaattttctg   2820
ttccttttga aagtataatc ctaactttca tctccggctg acctggtaat atcttctagc   2880
tccttttacc ttatattttt ttcagttgct tgagaaatag cggtaggaaa attgacacat   2940
gtcattcgta aatccatggg acttagagca actccaagag cttcctaaga aattgttccc   3000
caaaacatca tatagggggc tgctgaaaaa aatccactaa gagcaactcc aaatgagtgc   3060
tagaaaattt ccccaaaaaa tgattattgg ggatatgtta aaaaatttta ggggtgaatt   3120
atcatgtata ctccaacgat tccgttaaac aaatgcgact caatctcagc cacagtctga   3180
gtcttacaga cacacacaaa acctaacatg ccggtggcag ccacattatc acacaccgga   3240
acaaataact ttgaggcaaa aacacattat gcaagcagag aaacaccaga acagactccc   3300
agctgttgaa gtgcaaatgt gttttctata tttgagttac ttgctggtaa atcccgatcg   3360
ggaatgtaat aatcggggag ttgcattagc acttttgcag caagctaagc caactggttg   3420
ggaatgtcaa gcattcttga gcaggagtac tagtcaagtt aacaggcttc agatcccatc   3480
caatcattgt cacatttgaa tataacttga gcgggtagaa aaaatatcat aacaaaggca   3540
tcatggactg aatcctaaac atcataacga aggcatcatg gactgaatag cgatcatcat   3600
aacaacggca ggaaacagac tcccaactga atcatggtta acatggactg aattgtggtg   3660
gcactgcatg cagtgcgaga tgcatcatat ccaggtcaat tcaggttagc aaatgcaagg   3720
ccacaggagt tgccgccagg gaggaggctc taggcgaggt cacgggagtt gcggtggaag   3780
ttgctgcgga ttggggaaga cctttgctcg ccaatatttg agggagagtg gagctcggat   3840
gcgggacgct gataatttgg gggaaggaaa ggggaactat tgggtggaga attttttgtt   3900
tttcacccca aaacatgttt ttgggttggt tttagcgttc ttctggagat gctcttaagc   3960
aactagcaca tgagacatgg catagatatc aagaactgca aggagaggtt caagttcaaa   4020
tctgaagaag tctgcaaggg catgtccaca gattcagcgg ttttggagtt gggaaataac   4080
ttcagctttc ttttcttttt gttgttgaga cgttcttttc tttttctttt ttttttgttg   4140
ttgttgaggc gtcagctcga cgttttcatt ctacacatta gaaagtggca gtagcgcaag   4200
agataccaca gggccaaaac tactagtggt actgaaagtt ttcattcgaa gaatcagtaa   4260
gtggcactat cacaggaaga aacattgcaa ggccaaactt ggcgtccact gactgcgctt   4320
caatattact tgagcaactt gctagcctcc cgatcccgga aggatggttt gataaactaa   4380
ttctctaatt gaagtgggaa cccttaagaa ccaaacgtcc actactccaa atttgattgc   4440
aaaagaaaaa agaatctagc ccattccgcg gaatcacgcc agaaggctcg ctaattgaag   4500
catgcaagca aggcagcaaa gagaacagca cgcatcgacg ggttcctgca tccacaagca   4560
cgaacttggc aacttgccat ggtcgcctcg agggaaagaa atagaagaaa aaatggaaag   4620
agggcaagac gggggcgaaa ccagctaagc tcaccgagcg ccgcgcactg ggtgatgacg   4680
gcgacctcct cccgcgagac ctcggcggcg gccgctagat cccccaccgc ccggatcggc   4740
agggccacct cgtccgtcac cgcgagcgcc gccgacatgg agtcaaatct gcacacgagc   4800
acacgccgag aaccagaaga gactcggtga aaggagtatc cccgaagaga aaaggaatta   4860
gggttaatcg agggagggtt ttatctgcac gcccccggat tcatcacgcg actgctacct   4920
```

gagacgataa gacgacgacg aaggcgaaat ttgatttggg ttttgcctgg cctcctctcc 4980
tctcgaagct tcacaacacg ccgagttatt tgatattgta acaatctcgt cgcgcggctt 5040
caccagttat tactccgtag ttatacttcg ctagtttagt att 5083

<210> SEQ ID NO 39
<211> LENGTH: 819
<212> TYPE: DNA
<213> ORGANISM: maize

<400> SEQUENCE: 39
catccatcca tccatccatt tccaatccca atcccaatcc caccagtgtc cagtgctcgg 60
ggaaccgaca cagctcctca gcagagtagc cagcacgaca agcccgatca gcagacagca 120
ggcatggcac tcgcggaggc cgacgacggc gcggtggtct tcggcgagga gcaggaggcg 180
ctggtgctca agtcgtgggc cgtcatgaag aaggacgccg ccaacctggg cctccgcttc 240
tttctcaagg tcttcgagat cgcgccgtcg gcgaagcaga tgttctcgtt cctgcgcgac 300
tccgacgtgc cgctggagaa gaaccccaag ctcaagacgc acgccatgtc cgtcttcgtc 360
atgacctgcg aggcggcggc gcagcttcgc aaggccggga aggtcaccgt gagggagacc 420
acgctcaaga ggctgggcgc cacgcacttg aggtacggcg tcgcagatgg acacttcgag 480
gtgacggggt tcgcgctgct tgagacgatc aaggaggcgc tccccgctga catgtggagc 540
ctcgagatga agaaagcctg ggccgaggcc tacagccagc tggtggcggc catcaagcgg 600
gagatgaagc ccgatgccta gtagtggcga ttgcgaccag tgtttaaccc atgacgcagc 660
gccgtcacag atgtcccgtg tggtcttgcg ctttagcaat ttctctctgg agggagcgtg 720
tattgttatc ttgtgatcga gagcctgtgt gctgcctttg cttcttgtga ttatatagct 780
actgaataaa gatgtagcgt tcttcaaaaa aaaaaaaaa 819

<210> SEQ ID NO 40
<211> LENGTH: 165
<212> TYPE: PRT
<213> ORGANISM: maize

<400> SEQUENCE: 40

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
            165

<210> SEQ ID NO 41
<211> LENGTH: 917
<212> TYPE: DNA
<213> ORGANISM: maize

<400> SEQUENCE: 41

```
cgttgtcgga acgtcccgtc gatgttcgga aacgagcacg acccgtcgac tcctgcttct      60
tggcggagaa gaaaggggac gacgagcgag cgttttgact ttgatttcct cgctaaaacc     120
ggccgctgtt tttgctttcc gcgcgagccg cccacgttat tgactgacgc tggtgcgaga     180
gcgctgctgc ctctgcggtt gccgtctgcg ctccagtggt agccgagaat attgttaggt     240
ccgtaggatc agatttgcta cgtactaaaa aaattcctta aactttaatt gtgtattttt     300
tttaaaaaaa attatagcat ttatcagcaa caaaactcta aaaacatgtt tagttcgctg     360
cttaatttat cacatattgt ctaaatttta tatataaatt atttaattcg aacgactaac     420
cagaacccag acctacaata aatttgcccc cgctgctgcg ctccccagct ccccaagtcc     480
ctaacccgcc ctcgctttgt cgccgcggca cacggttttg gccgtggaca ggacagttgc     540
accctagccc cattggccga ttccgagcta ggaaggagta tatgcgtatc ggtagtaacc     600
gaggagcaac gcaacatgtc cacagcccgc gcgctggtaa cgggtccatg cgtcttggct     660
catcaggtgc cccaagggac gccctcgccc ggtctgaccc acctatataa acttaaaact     720
tgtgccccaa catcatcagt tcgtatcaca cccaacctcc cactgtaaaa aagagcagcg     780
gaacgtgcgt gcatccatcc atccatccat ttccaatccc aatcccaatc ccaccagtgt     840
ccagtgctcg gggaaccgac acagctcctc agcagagtag ccagcacgac aagcccgatc     900
agcagacagc aggcatg                                                    917
```

<210> SEQ ID NO 42
<211> LENGTH: 384
<212> TYPE: DNA
<213> ORGANISM: maize

<400> SEQUENCE: 42

```
tcgactggag cacgaggaca ctgacatgga ctgaaggagt agaaaatcac ctagctagaa      60
aggagagcac cgagcgctgc accactactg ctgatatgag cacctgaacc ttctgggcaa     120
ccacatccgg tccctgcccc tgatcatccg cagcagccat ggcgcagcag caggagaaga     180
agcagcagca gagggggaag ctgcagaggg tgctaaggga gcagaaggct cggctctaca     240
tcatccgccg atgcgtcgtc atgctcctct gctggagtga ctgatccatc tcaagcatgc     300
atgataaacc tgtgctcttt ttttttcctt ctgttttttc ccctcttttt cccatccttt     360
tcaccttgcc actttggtgg gcga                                            384
```

<210> SEQ ID NO 43
<211> LENGTH: 41
<212> TYPE: PRT
<213> ORGANISM: maize

<400> SEQUENCE: 43

Met Ala Gln Gln Gln Glu Lys Lys Gln Gln Gln Arg Gly Lys Leu Gln
1               5                  10                  15

Arg Val Leu Arg Glu Gln Lys Ala Arg Leu Tyr Ile Ile Arg Arg Cys
            20                  25                  30

```
Val Val Met Leu Leu Cys Trp Ser Asp
        35                  40


<210> SEQ ID NO 44
<211> LENGTH: 788
<212> TYPE: DNA
<213> ORGANISM: maize

<400> SEQUENCE: 44

cgactggagc acgaggacac tgacatggac tgaaggagta gaaaaactaa cacttcacgt      60

gcccccatcc ttttccgcct caagtcaagt gttcacggtc catcctctcg agagtctagg     120

cccttctccc gaagccgcag acgcagaaaa cggctctgca tatggaggcg aagaagaagc     180

cgtcggcccc cgccgccgtc ggagccgcgc cgccgccgcc gggtaacggg tacttcagca     240

ccgtcttctc cgcgccgact gcgggaagcg caagtgacgc aaagcatgcg gacttgtaca     300

cgatgctgaa caagcagagc tccagagggc agaatggcag agatggcaaa tcccacagcc     360

gccctactta caaggatggc aaacatgctc atccaaatga gccatcagaa tctccttact     420

ttggctcatc cgtgcattac ggtggtcggg agttctacag cagcgtttta cggaagcaac     480

cagccaatga accccatacg gattacaagg gggacaaccc ggatggctct gctaccagag     540

gtgattggtg gcaaggttca ctttattact gaataatctg ctgggacctc tcccttttgt     600

gaacaaggaa taaaaggggt agagctgaga atggtttgtt gtagtgttgg aagtgttgac     660

gcgagccgtc aagcatcgat caatagtaat agttgtaata gttgaaagct gcgtcgtgac     720

tacaagcatc ctgttggtgg aggcagtatt ttagatccat catcacgcct ggacagatgt     780

gggtgtcc                                                              788


<210> SEQ ID NO 45
<211> LENGTH: 136
<212> TYPE: PRT
<213> ORGANISM: maize

<400> SEQUENCE: 45

Met Glu Ala Lys Lys Lys Pro Ser Ala Pro Ala Ala Val Gly Ala Ala
1               5                   10                  15

Pro Pro Pro Pro Gly Asn Gly Tyr Phe Ser Thr Val Phe Ser Ala Pro
            20                  25                  30

Thr Ala Gly Ser Ala Ser Asp Ala Lys His Ala Asp Leu Tyr Thr Met
        35                  40                  45

Leu Asn Lys Gln Ser Ser Arg Gly Gln Asn Gly Arg Asp Gly Lys Ser
    50                  55                  60

His Ser Arg Pro Thr Tyr Lys Asp Gly Lys His Ala His Pro Asn Glu
65                  70                  75                  80

Pro Ser Glu Ser Pro Tyr Phe Gly Ser Ser Val His Tyr Gly Gly Arg
                85                  90                  95

Glu Phe Tyr Ser Ser Val Leu Arg Lys Gln Pro Ala Asn Glu Pro His
            100                 105                 110

Thr Asp Tyr Lys Gly Asp Asn Pro Asp Gly Ser Ala Thr Arg Gly Asp
        115                 120                 125

Trp Trp Gln Gly Ser Leu Tyr Tyr
    130                 135


<210> SEQ ID NO 46
<211> LENGTH: 2631
<212> TYPE: DNA
```

<213> ORGANISM: maize

<400> SEQUENCE: 46

```
aaagcttaca cttcataaga gattcatagt tttatcttac agccatcgtt gtcaacctca     60
actaccatgc aatccgtttg ggattcaact agcaagtaag gggatgtttg tttgggttta    120
taatctgtct ggattatata atctaacaac ttttgaacta acacttagtt caagaattgt    180
tggattatat aatctaggca gattataatc ccaaacaaac acttcctaag tcttgtacag    240
gctatagaga ttatttttcc agaatggagg agggataatg acaagaccta aaagaaagtt    300
atgtttatgg aaaacaaaaa aatggagcca ggataatgac acaaaagaaa ggtatgtttt    360
ctggaataaa aaaaattaaa tatatatttt gaacttccta agactggaac atgataccta    420
agctggacag atgatcaagg acagttttac ccctggagac agaaaaactt ataagactta    480
gctttctaca tcatatcctg ttttgtatgt ctcataatta ggttccttgt attaagacga    540
ccaacctatc atttgttata caaaattcga acgactgctg aagtctcgaa gtatatagtc    600
taggctgatt aaaatgtaag tatgggttaa agtgctgctg gtaacaaact aaatacaact    660
gtatgatgtt gttgacaaca agacataact caaaatggga gcaccaacaa agtgactggc    720
accggtgatg caagcataac ctaaacacaa ctaatggaaa acgcgaattg gaaactatga    780
aagtgtccca tatatggtat accttgttca caaaagggag aggtcccagc agattattca    840
gtaataaagt gaacctgaaa gtgaagtcta gcaagtcagt gtatgagcgt ccatgtatat    900
actgaagata atacacaaat tgatgcaatg ataccttgcc accaatcacc tctggtagca    960
gagccatccg ggttgtcccc cttgtactgg atttaaaatt caaaataaac attagactta   1020
agcgctccaa atgatctgta ctacgtatat ataaaaaggt tctacgtaca tccgtatggg   1080
gttcattggc tggttgcttc cgtaaaacgc tgctgtagaa ctcccgacca ccgtaatgca   1140
cggatgagcc aaagtaagga gattctgatg gctcatttgg atgagcatgt ttgccatcct   1200
tgtaagtagg gcggctgtgg gatttgccat ctgagcacga atttaaactt ccatagttaa   1260
aatcagtgct ccagattaat tctaagctaa gatggtgaga aaaggtttta agtatcgttg   1320
tgcttatgaa cgcgacctaa atcgaagaga aacgtcaaat tgacaagagt acccagaact   1380
acctctgcca ttctgccctc tggagctctg cttgttcagc atcgtgtaca agtccgcatg   1440
ctttgcgtca cttgcgcttc ccttgaatgc aaaacaaagt caaaatgtca acgtcatatc   1500
caaatagatt ttgcataatc ctataggtcc tctattatca aaatcacccc tcatcagaat   1560
taaattggga aaccgttgaa gtccctccac aaatcgcaac atagtaacgg actctttcat   1620
caaatcgcac cagctcacta atcatgcaaa aaaattacta agaccccagg aatctgagag   1680
caaaatatca gaacgatggc gtgaagagac ggcccgtacc gcagtcggcg cggagaagac   1740
ggtgctgaag tacccgttac ccggcggcgg cggcgcggct ccgacggcgg cgggggccga   1800
cggcttcttc ttcgcctcca tatgcagagc cgttttctgc gtctgcggct tcgggagaag   1860
ggcctagact ctcgagagga tggaccgtga acacttgact tgaggcggaa aaggatgggg   1920
gcacgtgaag tgttagttgt aggcggcggc ggccggcggg gaaggaagca gttggttgtt   1980
cgcctcgtgg cgtcctgctt cggccaacat ctgtgccggc atttaaaggc ctcgacggag   2040
cgactcggtt tcgctatttc ggagatctta aggggctgaa tggagaaaat tgtgtttagc   2100
tttcatccac atccatccaa cctgcagtga gacttgcaga gtgcagactc ccgtattaca   2160
gggacggtcc tgaataagtt agtagtttta tttcagagat tcaacgatgt tagtatacga   2220
attatttaga cacgtttgga atcatccagt tttttagcaa tctgatttat aaaaagtcaa   2280
```

-continued

```
gtgcttccaa acatatcaga ttatgcttcg gttcttaaaa atcggactgc ctcttccata   2340

actaaaatta gtttttaact tggtagaaat tagtgattgt aaccgctctt aggtctatgc   2400

atgtgattcc ctcgatgtct ttatcccatt tgaatattta attattattt aaaaatttta   2460

gattaaaaat attaattcaa tctatattta aaattggcaa caaagaaaaa caaagagaat   2520

aatagaatca attacttttg gaatagagta aggattgaat ttgtctttgt gtataacaaa   2580

gctagaagtt ggtttccaag aactagcctc taacacgcac acctattttt t            2631
```